(12) United States Patent
Roberts et al.

(10) Patent No.: US 7,183,440 B2
(45) Date of Patent: Feb. 27, 2007

(54) PHARMACEUTICALLY USEFUL COMPOUNDS

(75) Inventors: Stanley Michael Roberts, Kirsbrook (GB); Maria Gabriella Santoro, Avellino (IT); Vasudev Jadhav, Chapel-en-le-Frith (GB); Alan Michael Happe, Canterbury (GB); Jérôme Dauvergne, Kingsdown (GB)

(73) Assignee: Charterhouse Therapeutics Ltd (GB)

( * ) Notice: Subject to any disclaimer, the term of this patent is extended or adjusted under 35 U.S.C. 154(b) by 0 days.

(21) Appl. No.: 11/059,086

(22) Filed: Feb. 7, 2005

(65) Prior Publication Data

US 2006/0040869 A1 Feb. 23, 2006

(51) Int. Cl.
*C07C 315/00* (2006.01)
*C07C 49/00* (2006.01)
*A61K 31/12* (2006.01)
*A61K 31/095* (2006.01)

(52) U.S. Cl. .......................... 568/18; 568/63; 568/379; 514/690; 514/706

(58) Field of Classification Search .................... None
See application file for complete search history.

(56) References Cited

FOREIGN PATENT DOCUMENTS

WO WO 0056341 * 9/2000
WO WO 0144254 * 6/2001

OTHER PUBLICATIONS

Ramesh et al. Enantioselective Synthesis of 4-Aminocyclopent-2-ene-1-one from Tricyclo[5.2.1.0] decenyl Enaminones.☐☐Tetrahedron Letters, 1998, vol. 39, p. 1429-1432.*
Noyori et al. Photochemistry of 2,6-Cycloheptadienones in Strong Acid. Journal of the American Chemical Society, 1972, vol. 94, (12), p. 5105-5106.*
Asami et al. An Asymmetric Synthesis of (1S, 4R)-4-Amino-2-cyclopentenol Derivatives. Tetrahedron Letters, 1999, vol. 40, p. 1563-1564.*

* cited by examiner

Primary Examiner—Sikarl A. Witherspoon

(74) Attorney, Agent, or Firm—Jones Day

(57) ABSTRACT

A compound of formula (I) or (II): wherein A is hydrogen or $CR^1R^2$; Y and Z are each, independently, hydrogen or a halogen; X is $-NR^4R^5$, or $R^7$; $R^1$ is hydrogen, or a substituted or unsubstituted alkyl or alkenyl group containing 1–4 carbon atoms; when X is $-NR^4R^5$, $R^2$ is a substituted or unsubstituted alkyl, alkenyl, alkynyl, aryl, aralkyl aralkenyl, or aralkynyl group, that optionally includes at least one heteroatom in its carbon skeleton and contains 1–12 carbon atoms; when X is $R^7$, $R^2$ is an unsubstituted alkyl, alkenyl or alkynyl group, or a substituted or unsubstituted aryl, aralkyl aralkenyl, or aralkynyl group, that optionally includes at least one heteroatom in its carbon skeleton and contains 1–12 carbon atoms; $R^3$ is a substituted or unsubstituted alkyl, alkenyl, alkynyl, aryl, aralkyl aralkenyl, or aralkynyl group, that optionally includes at least one heteroatom in its carbon skeleton and contains 1–12 carbon atoms; $R^4$ is hydrogen, a substituted or unsubstituted alkyl, alkenyl, alkynyl, aryl, aralkyl aralkenyl, or aralkynyl group, that optionally includes at least one heteroatom in its carbon skeleton and contains 1–12 carbon atoms, $-COOR^8$, or $-COR^8$; $R^5$ is hydrogen, or a substituted or unsubstituted alkyl or alkenyl group containing 1–5 carbon atoms; $R^7$ is an unsubstituted alkyl, alkenyl, or alkynyl group, that contains 1–4 carbon atoms; and, $R^8$ is an unsubstituted or halo-substituted alkyl, aryl, or aralkyl group, that contains 1–12 carbon atoms

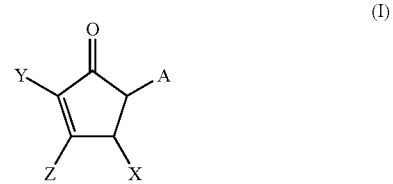

(I)

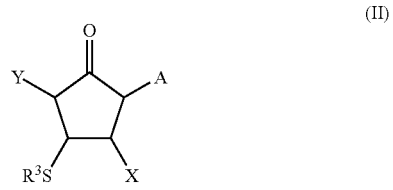

(II)

39 Claims, No Drawings

US 7,183,440 B2

PHARMACEUTICALLY USEFUL COMPOUNDS

This application is entitled to and claims priority benefit to International Application No. PCT/GB2003/003413, filed Aug. 6, 2003, and Great Britain Application No. 0218261.6, filed Aug. 6, 2002, the entire contents of each of which is incorporated herein by reference.

DESCRIPTION

The present invention relates to certain cyclopentanone and cyclopentenone derivatives. It also relates to the preparation of such derivatives, and to their use in medicine and other fields. The invention further relates to certain cyclopentanone derivatives with enhanced water solubility, lipophilicity and/or therapeutic indices, and to methods of enhancing the water solubility, lipophilicity and/or therapeutic indices of pharmaceutically active cyclopentenone derivatives.

Various compounds comprising the cyclopentenone ring structure (also known as the cyclopentenone nucleus) are capable of inducing the heat shock response. The heat shock response is a finely regulated and highly conserved mechanism to protect cells against different types of injury, including extreme temperatures, oxidative stress, exposure to toxins and viral infection (1). In human cells, triggering of the heat shock response requires activation of a transregulatory protein, the heat shock transcription factor type 1 (HSF 1), which controls the expression of cytoprotective heat shock proteins (HSPs) (1). Whereas HSP induction was at first interpreted as a signal for detection of physiological stress, it is now accepted that HSPs are utilised by cells as molecular chaperones in the repair process following different types of injury to prevent damage resulting from the accumulation and aggregation of non-native proteins (1). In particular, a cytoprotective role of the heat shock protein HSP70 has now been described in a wide variety of human diseases, including ischemia, inflammation and viral infection (2–5). For these reasons HSF 1 is considered a novel, attractive target for cytoprotective and antiviral drugs. In the case of viral infection, Santoro et al. have shown that a class of prostaglandins (PGs) with potent antiviral activity function as HSP70 inducers via HSF1 activation (6,7).

The ability of prostaglandins of the A type (PGAs) to inhibit viral replication and prevent the establishment of persistent infections was first reported in 1980 (8). It is now well established that PG containing an α, β-unsaturated carbonyl group in the cyclopentane ring structure (cyclopentenone PG, cyPG) possess activity against a wide variety of DNA and RNA viruses, including herpes viruses, paramyxo viruses, orthomyxo viruses and retroviruses in in vitro and in vivo experimental models (9). The mechanism of the antiviral activity is distinct from any other known antiviral agent and is thought to involve the induction of heat shock proteins and the inhibition of the transcription factor NF-κB (nuclear factor-κB) in the infected cell.

NF-κB is an inducible eukaryotic transcription factor which has a critical role in promoting inflammation and viral replication (11). In most cells, NF-κB exists in an inactive cytoplasmic complex, whose predominant form is a heterodimer composed of p50 and p65 subunits, bound to inhibitory proteins of the IκB family, usually IκBα, and is activated in response to primary (viruses, bacteria, UV) or secondary (inflammatory cytokines) pathogenic stimuli (12). Stimulation triggers rapid phosphorylation and degradation of IκBα, resulting in NF-κB translocation to the nucleus, where the factor binds to DNA at specific κB-sites, inducing a variety of genes encoding signalling proteins. Target genes include those coding for inflammatory and chemotactic cytokines, cytokine receptors and viral proteins. NF-κB is involved in many pathological events including progression of AIDS by enhancing HIV-1 transcription and is considered an attractive therapeutic target for novel antiviral and anti-inflammatory drugs (12). Santoro et al. have shown that cyclopentenone prostaglandins inhibit NF-κB activation and NF-κB dependent HIV-1 transcription in human cells, by preventing IκBα phosphorylation and degradation, and that this effect is strictly associated with HSF1 activation (11).

Santoro et al. have identified the molecular structure of natural prostaglandins responsible for HSF activation and NF-κB inhibition (13). One component of the PGA molecule, cyclopent-2-en-1-one (also known as 2-cyclopenten-1-one), at a concentration of 125–500 μM, has been shown to be able to activate HSF1 and to rapidly and selectively trigger the synthesis of cytoprotective HSP70. At the same concentration, cyclopent-2-en-1-one has been shown to be able to block NF-κB activation by chemical or physiological inducers. These effects are associated with antiviral activity during infection with rhabdoviruses (13).

A family of pharmaceutically active cyclopent-2-en-1-one derivatives is described in International patent application no. PCT/GB00/01086, published as WO00/56341. The experimental results set out in this document show members of this family of compounds to be potent activators of HSF and inhibitors of NF-κB activity. They also show such compounds to be potent inhibitors of HSV-1 and Sendai virus replication. All of the compounds disclosed in this reference include a group—OX bound to the carbon atom in the 4 or 5 position in the cyclopentenone ring, in which X can be an alkyl, aryl or aralkyl group, or an alkyl, aryl or aralkyl substituted silyl group. A further family of pharmaceutically active cyclopentenone derivatives is described in International application no. PCT/GB00/04868, published as WO01/44254. Members of this family also comprise a cyclopent-2-en-1-one ring with a similarly defined group—OX bound to the carbon atom in the 4 position in the ring. They also include a double bond to the carbon atom in the 5 position in the ring, α to the carbonyl carbon.

There is no suggestion in the literature that any cyclopentenone derivatives, other than the natural prostaglandins and those substituted in either or both of the 4 and 5 positions in the cyclopentenone ring with an oxy moiety, have a capacity to exhibit biological activity of the above discussed nature.

Surprisingly, it has now been found that certain cyclopentenone derivatives, in which neither of the carbon atoms in the 4 and 5 positions are bound to an oxygen atom and which do not include prostaglandin like side chains, are pharmaceutically active in at least one of the aforementioned ways.

According to the present invention, there is provided a compound of formula I or II:

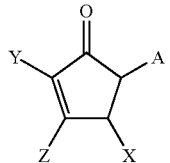

I

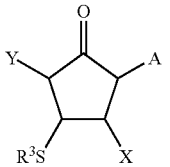

II wherein:
A is hydrogen or =CR$^1$R$^2$;
Y and Z are each, independently, hydrogen or a halogen;
X is —NR$^4$R$^5$, or R$^7$;
R$^1$ is hydrogen, or a substituted or unsubstituted alkyl or alkenyl group containing 1–4 carbon atoms;
when X is —NR$^4$R$^5$, R$^2$ is a substituted or unsubstituted alkyl, alkenyl, alkynyl, aryl aralkyl aralkenyl, or aralkynyl group, that optionally includes at least one heteroatom in its carbon skeleton and contains 1–12 carbon atoms;
when X is R$^7$, R$^2$ is an unsubstituted alkyl, alkenyl or alkynyl group, or a substituted or unsubstituted aryl, aralkyl aralkenyl, or aralkynyl group, that optionally includes at least one heteroatom in its carbon skeleton and contains 1–12 carbon atoms;
R$^3$ is a substituted or unsubstituted alkyl, alkenyl, alkynyl, aryl, aralkyl aralkenyl, or aralkynyl group, that optionally includes at least one heteroatom in its carbon skeleton and contains 1–12 carbon atoms;
R$^4$ is hydrogen, a substituted or unsubstituted alkyl, alkenyl, alkynyl, aryl, aralkyl aralkenyl, or aralkynyl group, that optionally includes at least one heteroatom in its carbon skeleton and contains 1–12 carbon atoms, —COOR$^8$, or —COR$^8$;
R$^5$ is hydrogen, or a substituted or unsubstituted alkyl or alkenyl group containing 1–5 carbon atoms;
R$^7$ is an unsubstituted alkyl, alkenyl, or alkynyl group, that contains 1–4 carbon atoms; and,
R$^8$ is an unsubstituted or halo-substituted alkyl, aryl, or aralkyl group, that contains 1–12 carbon atoms.

When, in preferred embodiments A is =CR$^1$R$^2$, the inventive compound are of the formulae Ia and IIa:

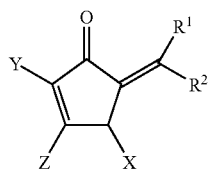

Ia

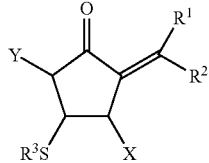

IIa

R$^1$ is preferably hydrogen or an alkyl group containing 1, 2, 3 or 4 carbon atoms, and, more preferably, is hydrogen. R$^2$ preferably contains 1, 2, 3, 4, 5, 6, 7, 8, 9, 10 or 11 carbon atoms and, more preferably, is an unsubstituted alkyl, or a substituted or unsubstituted aryl or aralkyl group. In preferred embodiments, R$^2$ is an alkyl group containing 3, 4, 5, or 6 carbon atoms or an, optionally substituted, phenyl group. When R$^2$ is a substituted phenyl group, it can be halo-, nitro-, alkyl- or alkoxy-substituted. In more preferred embodiments R$^2$ is an isopropyl, cyclopropyl, 1,2-dimethylethyl, n-pentanyl, n-hexanyl, phenyl, 4-methoxyphenyl, 4-flourophenyl, 4-chlorophenyl, 2,4,6-trimethylphenyl, 2,5-dimethoxyphenyl or 4-nitrophenyl group. R$^2$ is most preferably an isopropyl or a phenyl group.

R$^3$ can be an R$^x$CH$_2$— group, such that the group —SR$^3$ is an —SCH$_2$R$^x$ group, wherein R$^x$ is hydrogen or a substituted or unsubstituted alkyl, alkenyl, alkynyl, aryl, aralkyl aralkenyl, or aralkynyl group, that optionally includes at least one heteroatom in its carbon skeleton. R$^3$, preferably, contains 1–12 carbon atoms.

The group R$^3$ or R$^x$, preferably, includes at least one hydrophilic group. Said hydrophilic group can be or include a hydroxyl, carbonyl, carboxyl, amino, amido, quaternary ammonium or thiolyl group. R$^3$ or R$^x$, therefore, can provide the functionality of an amine, amide, peptide, ester, carboxylic acid, carboxylic acid salt, alcohol, aldehyde, ketone or thiol to an inventive compound. In preferred such compounds the group —SR$^3$ is an S-cysteinyl or a hydrophilic substituted S-cysteinyl group. Preferred substituted S-cysteinyl groups include di- and tri-peptide groups that include an S-cysteinyl moiety, such as an S-glutathionyl group.

Alternatively, the group R$^3$ or R$^x$ can include at least one lipophilic group and/or is lipophilic. Such lipophilic groups include substituted and unsubstituted alkyl, alkenyl, alkynyl, aryl, aralkyl, aralkenyl, or aralkynyl groups that, optionally, include at least one heteroatom in their carbon skeletons, but which do not carry any substituents that render them hydrophilic. Preferred such groups include substituted and unsubstituted phenyl and napthyl groups and N-tert-butoxycarbonyl S-cysteinyl ester (e.g. methyl and ethyl) groups.

In preferred embodiments, the group —SR$^3$ is an S-cysteinyl or a substituted S-cysteinyl group. Preferred substituted S-cysteinyl groups include di- and tri-peptide groups that include an S-cysteinyl moiety, such as S-glutathionyl, S-cysteinyl ester and other like groups, including N-tert-butoxycarbonyl S-cysteinyl and N-tert-butoxycarbonyl S-cysteinyl ester (e.g. methyl and ethyl) groups.

Y and Z are preferably chlorine or hydrogen and, more preferably, hydrogen.

X is preferably —NR$^4$R$^5$.

R$^4$ is preferably a phenyl group, —COOR$^8$ or —COR$^8$. R$^5$ is preferably hydrogen or a COO-alkyl group, wherein the alkyl group contains 1–4 carbon atoms, but is more preferably hydrogen.

R$^7$ is preferably an alkyl group containing 1, 2, 3, 4 or 5 carbon atoms. R$^7$ is more preferably a methyl or n-butyl group. $R^8$, preferably, is an optionally halo-substituted alkyl group containing 1, 2, 3, 4 or 5 carbon atoms, or an aryl group. In further preferred embodiments, $R^8$ is a t-butyl group, wherein $R^4$ is a t-butoxycarbonyl group, a phenyl group, wherein $R^4$ is a benzyl group, a chloromethyl or an ethyl group.

Certain compounds in accordance with the invention can exist in the form of a least two enantiomers and all such enantiomers, unequal mixtures thereof and racemates are encompassed by the present invention. Both R- and S-enantiomers of these compounds are useful. They can each be provided in a form substantially free of the other enantiomer (e.g. at least 75%, 85%, 90%, 95% or 99% free (w/w)). Mixtures of enantiomers (e.g. racemic mixtures) may however also be used.

Compounds in accordance with the invention exist in both E and Z forms, i.e. with $R^1$ or $R^2$ being cis- or trans to the carbonyl carbon in the cyclopentenone ring. The present invention encompasses all such individual isomers and mixtures thereof.

Preferred compounds in accordance with the present invention include the following:

CTC-121
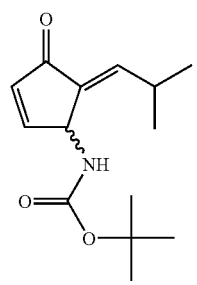

CTC-122
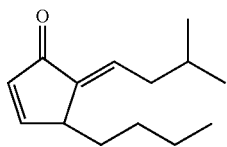

CTC-145
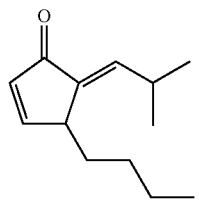

CTC-150
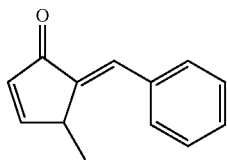

CTC-154
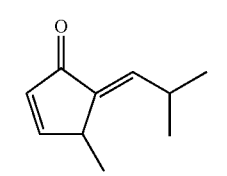

-continued

CTC-162
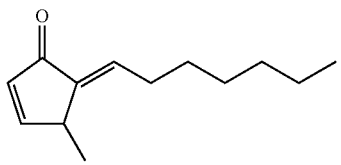

CTC-164
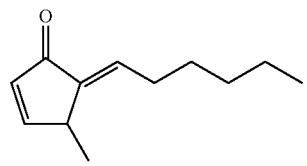

CTC-172
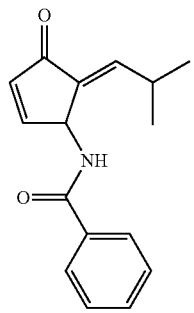

CTC-177
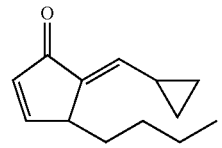

CTC-191
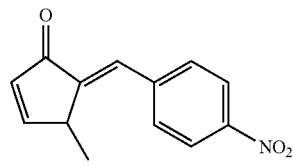

CTC-195
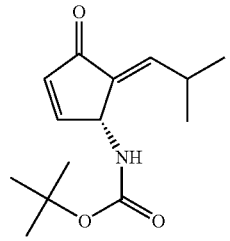

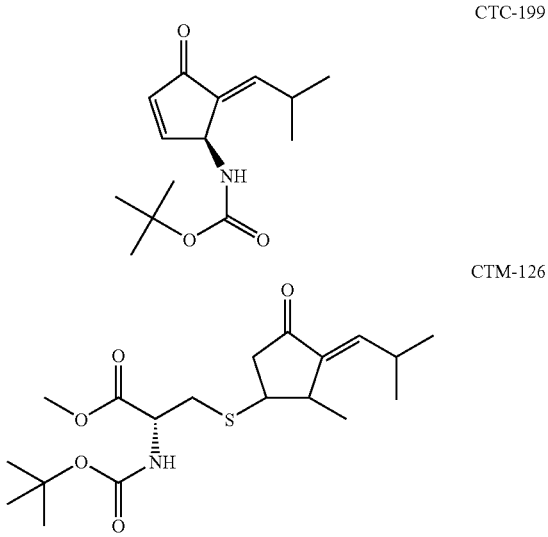

CTC-199

CTM-126

Further preferred compounds in accordance with the present invention are described in Examples 1, 4, 5, 8, 9, 12, 13, 16, 17, and 21–32. The most preferred compound in accordance with the invention is (2R)-3-((1R,2R)-(E)-3-Benzylidene-2-tert-butoxycarbonylamino-4-oxocyclopentylsulfanyl)-2-tert-butoxycarbonylaminopropionic acid (CTM-228), but all forms of 3-Benzylidene-2-tert-butoxycarbonylamino-4-oxocyclopentylsulfanyl)-2-ter-butoxycarbonylaminopropionic acid are within the scope of the present invention.

Although many cyclopentenone derivatives are biologically and pharmaceutically active, many such compounds are also poorly soluble in water or highly lipophilic. As such, these latter compounds are less suited to being administered to patients orally than by other routes of systemic administration, that are generally less favoured by patients, such as by parenteral injection. Moreover, such compounds are often biologically active in a manner that suggest usefulness in the topical treatment of skin conditions such as, for example, psoriasis and skin cancers. However, many are insufficiently lipophilic to penetrate the skin to the degree required to be therapeutic effective in such treatments.

The therapeutic index of a drug or pharmaceutically active compound is indicated by the ratio of its median lethal dose, or $LD_{50}$, to its medium effective dose, or $ED_{50}$. Because its use would generally involve a lower risk of causing toxic side effects in individual patients given a therapeutically effective dose, a compound with a larger therapeutic index would normally be preferred over an alternative with a smaller therapeutic index. Accordingly, if the therapeutic index of a particular pharmaceutically active compound could be increased without ill effect, this would be an attractive result.

Preferred compounds of formula II are either:

(a) more soluble in water at a temperature of 20–40° C.;

(b) less lipophilic; and/or, (c) have a greater therapeutic index;

or;

(d) less soluble in water at a temperature of 20–40° C.;

(e) more lipophilic; and/or, (f) have a greater therapeutic index;

than equivalent compounds of formula I. An equivalent compound of formula I to a preferred compound of formula II is a compound with, excepting the absent —$SR^3$ group and an additional hydrogen atom in the 2 position in the five membered ring, the same substitution pattern as the preferred compound of formula II.

Where a preferred compound in accordance with the invention is required to be less lipophilic than an "equivalent" compound, this means that the ratio of n-octanol to aqueous solubility (i.e. the n-octanol/water partition coefficient) for the preferred compound is lower than it is for the "equivalent" compound. Similarly, where a preferred compound in accordance with the invention is required to be more lipophilic than an "equivalent" compound, this means that the ratio of n-octanol to aqueous solubility (i.e. the n-octanol/water partition coefficient) for the preferred compound is higher than it is for the "equivalent" compound. The ratio of n-octanol to aqueous solubility is usually expressed in terms of its base ten logarithm, "logP", and a compound with a logP value of 1 will be 10 times more soluble in n-octanol than it is in water, a compound with a logP value of 2 will be 100 times more soluble in n-octanol than it is in water and so on. LogP values can be measured by experiment, or calculated using one of several available computer programs or algorithms. Examples of these include the Pomona College Medicinal Chemistry program, the MacLogP application from BioByte Corp. (Claremont USA), and the method described by Moriguchi et al. (20). Thus, it is preferred that compounds, required in this specification to be less lipophilic (or have greater water solubility) than equivalent compounds, will have lower logP values than such equivalents, and that compounds, required in this specification to be more lipophilic (or be less water soluble) than equivalent compounds, will have higher logP values than such equivalents. In this context, the logP values are preferably calculated values derived from applying one of the aforementioned programs or algorithms.

For each compound of formula I, there are many compounds of formula II that differ from each other solely by the nature of their —$SR^3$ substituents. The useful biological and pharmacological properties of equivalent compounds of formula I are often retained and sometimes even enhanced in the related —$SR^3$ substituted compounds of formula II. It has also been found that the lipophilicity and water solubility of compounds of formula II is highly dependent upon the nature of the —$SR^3$ group which they carry. In essence, increasing the lipophilicity of the group $R^3$ (in the —$SR^3$ substituent) will result in a compound of formula II that is more lipophilic and less water soluble, and vice versa, and the degree to which the lipophilicity or water solubility of an equivalent compound of formula I can be manipulated in this way is sufficient for many such compounds to be "adaptable" for both topical and oral use. Thus, compounds of formula II provide those skilled in the art with the means to adapt the physical properties of any given equivalent compound of formula I to suit a particular mode of delivery, e.g. oral or topical, without prejudicing its pharmacological properties. This represents a highly significant and surprising advantage of the present invention.

Where a preferred compound in accordance with the invention is required to have a greater therapeutic index than an "equivalent", this relationship must hold true for at least one therapeutic application. For the purposes of this specification, the existence of such a relationship can be established either by observation of in vivo effects, or via in vitro tests or assays of the type conventionally employed by persons skilled in the art for the purpose of predicting the therapeutic indices of putative drug substances. For example, an assay for one of the properties discussed below could be used in combination with a toxicity assay, to provide the required information for a particular pair of inventive compound and equivalent. Examples of appropriate assays are set out in Examples 35–38 below.

Certain preferred compounds of formula II have calculated or measured logP values that are at least 0.25, 0.5, 0.75, 1 or 1.25 higher or lower than the logP values for their equivalents of formula I, wherein the logP values for each compound of formula II and its equivalent of formula I are calculated or measured using the same technique. In embodiments, compounds of formula II have a logP value of 5 or less, and preferably of no more than 4.15, 4, 3, 2, or 1, when calculated by the method described by Moriguchi et al. (20). Compounds with logP values in these latter preferred ranges are generally more readily absorbed from the gastrointestinal tract and, therefore, are more suited to oral administration. See Lipinski et al. (21). In alternative embodiments, compounds of formula II can have a logP value of at least 3.5, 4.2, or 5 and preferably of up to 6 or 7 and such compounds are suitable, therefore, for use in topical formulations for application to the skin.

Compounds in accordance with the invention can include an —$SR^3$ group bound to a substituent, itself bound to the cyclopentanone or cyclopentenone ring, or an —$SR^3$ group forming a part or all of at least one of the groups $R^1$ and $R^2$. Compounds in accordance with the invention can also include a plurality of —$SR^3$ groups. Certain such compounds are of formula II and include a second —$SR^3$ group bound to a substituent, itself bound to the cyclopentanone or cyclopentenone ring, or a second —$SR^3$ group forming a part or all of at least one of the groups $R^1$ and $R^2$. Thus, in preferred embodiments of compounds of formula II, compounds in accordance with the invention can comprise an additional group —$SR^3$ bound to the first carbon atom in a side chain carried by the ring carbon atom adjacent ($\alpha$) to the carbonyl ring carbon atom.

As noted, $R^3$ can be an $R^xCH_2$— group, such that the group —$SR^3$ is an —$SCH_2R^x$ group, wherein $R^x$ is hydrogen or a substituted or unsubstituted alkyl, alkenyl, alkynyl, aryl, aralkyl aralkenyl, or aralkynyl group, that optionally includes at least one heteroatom in its carbon skeleton. $R^3$, preferably, contains 1–12 carbon atoms.

In those compounds of formula II which are more water soluble and/or less lipophilic than the equivalent compounds of formula I, the group $R^3$ or $R^x$, preferably, includes at least one hydrophilic group. Said hydrophilic group can be or include a hydroxyl, carbonyl, carboxyl, amino, amido, quaternary ammonium or thiolyl group. In such compounds, therefore, $R^3$ or $R^x$ can provide the functionality of an amine, amide, peptide, ester, carboxylic acid, carboxylic acid salt, alcohol, aldehyde, ketone or thiol to an inventive compound. In preferred such compounds the group —$SR^3$ is an S-cysteinyl or a hydrophilic substituted S-cysteinyl group. Preferred substituted S-cysteinyl groups include di- and tripeptide groups that include an S-cysteinyl moiety, such as an S-glutathionyl group.

In those compounds of formula II which are less water soluble and/or more lipophilic than the equivalent compounds of formula I, the group $R^3$ or $R^x$, preferably, includes at least one lipophilic group and/or is lipophilic. Such lipophilic groups include substituted and unsubstituted alkyl, alkenyl, alkynyl, aryl, aralkyl, aralkenyl, or aralkynyl groups that, optionally, include at least one heteroatom in their carbon skeletons, but which do not carry any substituents that render them hydrophilic. Preferred such groups include substituted and unsubstituted phenyl and napthyl groups and N-tert-butoxycarbonyl S-cysteinyl ester (e.g. methyl and ethyl) groups.

As has been noted, an advantage of certain compounds of formula II is that, because they are less lipophilic and/or more soluble in water at around room temperature and/or body temperature than are analogous compounds of formula I that do not include an —$SR^3$ substituent, they are more suited to use in orally administered pharmaceutical compositions. Thus, in a further preferred aspect, the present invention provides pharmaceutical compositions for oral administration, comprising a compound of formula II that is more soluble in water at a temperature of 20–40° C. and/or less lipophilic than an equivalent compound of formula I in which a hydrogen atom replaces said —$SR^3$ group. Such compositions can include one or more pharmaceutically acceptable diluent, carrier and/or other excipient suitable for use in compositions for oral administration.

As has also been noted, an advantage of certain other compounds of formula II is that, because they are more lipophilic and/or less soluble in water at around room temperature and/or body temperature than are analogous compounds of formula I that do not include an —$SR^3$ substituent, they are more suited to use in pharmaceutical compositions for topical administration, particularly to the skin. Thus, in a yet further preferred aspect, the present invention provides pharmaceutical compositions for topical administration, preferably to the skin, comprising a compound of formula II that is less soluble in water at a temperature of 20–40° C. and/or more lipophilic than an equivalent compound of formula I in which a hydrogen atom replaces said —$SR^3$ group. Such compositions can include one or more pharmaceutically acceptable diluent, carrier and/or other excipient suitable for use in compositions for topical administration.

Moreover, because the pharmaceutically active compounds of formula II can also have a greater therapeutic index than their equivalents without an —$SR^3$ substituent, they are potentially more useful in a therapeutic context.

In the pharmaceutical industry, a major problem with any potential drug is that it may be very biologically active but somewhat toxic. For example, an anti-tumour drug must be toxic towards certain groups of cells but not potentially harmful to other cells.

Cyclopentenone compounds are known to undergo Michael reactions with glutathione in the cell. Glutathione is found throughout the body and plays crucial roles in protecting cells from oxidative damage (maintaining redox balance). In this regard, work by Uchida et al. (22) and others has suggested a role for glutathione in protecting cells from oxidative stress as a radical scavenger. Uchida's work showed that cells with depleted glutathione retain higher concentration of radical oxygen species. It also demonstrated that, when such cells were treated with N-acetylcysteine and cell viability was measured, an increase in cell life and a decrease in the production of radical oxygen species was observed. Uchida et al. came to the conclusion that species capable of reducing glutathione levels in the cell, also reduce the cell's anti-oxidant defences and increase the induction of radical oxygen species. They also showed that cyclopentenone mediated production of radical oxygen species was well correlated with cytotoxicity and, thus, demonstrated a potentially important mode of cytotoxicity or induction of cell death by cyclopentenone compounds.

Glutathione is also known to protect cells from dangerous electrophilic species. For example, morphine type compounds undergo a Michael reaction with glutathione that results in complete deactivation of the drug (23). If large amounts of paracetamol (acetaminophen) are taken then glutathione in the liver is depleted [in 1999 there were 150 deaths in the UK from paracetamol poisoning]. If N-acetyl cysteine is taken intravenously or orally less than 15 h after the overdose it effectively removes the offending electrophilic paracetamol metabolite (24).

Other studies have shown that a reduction of intracellular thiol content can increase the sensitivity of tumour cells to radiation treatment. Moreover, cells exhibiting depleted levels of glutathione have been shown to be more susceptible to radiation, chemotherapeutic agents and oxygen radical species that otherwise would have been destroyed via radical reaction with glutathione (25).

A glutathione group cannot be added to a saturated moiety, such as a cyclopentanone group, via a Michael reaction. Thus, unless they are metabolised into the equivalent unsaturated cyclopent-2-en-1-ones, compounds in accordance with the invention that comprise a cyclopentanone group may be less likely to react with glutathione in vivo than are these unsaturated equivalents. Such saturated compounds, therefore, may be less likely to deplete the levels of glutathione in a patient's cells, and thereby compromise their anti-oxidant defences, than the equivalent cyclopent-2-en-1-one derivatives. Without wishing to be bound by theory, this may explain why some compounds in accordance with the invention that include one or more —SR$^3$ group have significantly enhanced therapeutic indices, in addition to enhanced or reduced water solubility and reduced or enhanced lipophilicity.

Without again wishing to be bound by theory, it is considered that compounds in accordance with the present invention, wherein the carbon atom in the 3 position in their cyclopentanone rings carries an —SR$^3$ group, enjoy their enhanced properties partially because they can act as pro-drugs for the equivalent cyclopent-2-en-1-ones, in the sense that it is thought that they are converted into the latter in vivo. In this regard, it is considered that, before it is cleaved, the group —SR$^3$ renders these compounds in accordance with the invention more suited to a chosen mode of administration (e.g., oral or topical to the skin) and that in vivo cleavage of the —SR$^3$ group releases, via a reverse Michael reaction, the more potent cyclopent-2-en-1-one equivalent.

Thus, in embodiments, compounds of formula II in accordance with the invention are transformable into equivalent cyclohex-2-en-1-one derivatives of formula I by a reverse Michael reaction, or are pro-drugs for such equivalents.

In further preferred embodiments, the group —SR$^3$ is an S-cysteinyl or a substituted S-cysteinyl group. In the context of this application, a substituted or unsubstituted S-cysteinyl group comprises a cysteinyl moiety that is bound to the ring via its sulphur atom, with the ring replacing the hydrogen atom that is bound to the equivalent sulphur atom in cysteine. Preferred substituted S-cysteinyl groups include di- and tri-peptide groups that include an S-cysteinyl moiety, such as S-glutathionyl, S-cysteinyl ester and other like groups, including N-tert-butoxycarbonyl S-cysteinyl and N-tert-butoxycarbonyl S-cysteinyl ester (e.g. methyl and ethyl) groups.

Without once again wishing to be bound by theory, it is considered that compounds in accordance with these latter embodiments of the invention are also capable of providing a secondary therapeutic effect resulting from their incorporation of a substituted or unsubstituted cysteinyl moiety. For example, when acting as pro-drugs in the aforementioned manner, such compounds may be capable of delivering both the equivalent cyclopent-2-en-1-one derivative and the reduced form of the substituted or unsubstituted cysteinyl moiety to target cells in a patient's body, where both may exert their therapeutic effects. The therapeutic effect exerted by the reduced form of the substituted or unsubstituted cysteinyl moiety can be the prevention of glutathione depletion, especially when the reduced moiety is glutathione, an analogue or precursor. For example, the reduced, substituted or unsubstituted cysteinyl moiety may compete with native glutathione, to reduce the amount of the latter that is bound by the cyclopent-2-en-1-one derivative (formed after in vivo cleavage) or a metabolite, or it may replace or lead to the replacement of glutathione bound by the derivative or a metabolite. Such activity is thought to contribute significantly to the reducing the toxicity of the inventive compounds and, hence, to the increased therapeutic indices enjoyed by these compounds, in comparison to the equivalent cyclopent-2-en-1-one.

Compounds in accordance with the invention preferably are capable of one or more of the following:
a) activating HSF
b) inhibiting NF-κB
c) inhibiting the replication of HSV-1
d) inhibiting the replication of Sendai virus.

A skilled person can readily assay for the above activities and examples of suitable assays are set out in Examples 35 and 36 below.

Compounds that have greater activity in at least one of the foregoing respects than cyclopent-2-en-1-one (at least at certain concentrations) represent preferred embodiments of the invention; those that enjoy such activity at a concentration within the range of 1–200 µM, or over the whole or a part of said range, being particularly preferred. Preferably, compounds in accordance with the invention have a level of activity in at least one of the foregoing respects that is at least twice the level of cyclopent-2-en-1-one. More preferably, it is at least 10 times that of cyclopent-2-en-1-one.

Activity in one of the above respects is indicative of a compound's capacity to be pharmaceutically active. Accordingly, in a yet further aspect, the present invention provides a compound in accordance with the invention for use in medicine (including veterinary medicine). Preferred such uses include the treatment of the human or animal body by therapy and diagnostic methods practised upon the human or animal body. The treatment may be prophylactic or may be in respect of an existing condition. Therapeutic (including prophylactic) and diagnostic methods, involving the use of a compound in accordance with the invention, are also within the remit of the invention.

The use of such compounds for the manufacture of medicament for use in therapeutic or diagnostic methods to be practised on the human or animal body, lie within the scope of a further aspect of the invention.

The preferred uses for compounds in accordance with the invention include the treatment of disorders which can be treated in a host by the activation of a heat shock transcription factor (e.g. HSF1), by the induction of heat shock proteins (e.g. hsp70) and/or by the inhibition of NF-κB. Certain preferred compounds in accordance with the invention can be used in therapeutic applications that involve activating HSF and inhibiting the activity of NF-κB.

Thus, in accordance with the invention, compounds in accordance with the invention can be used to treat diseases or conditions in which such activity is indicated or can be of advantage. They can also be used in the manufacture of medicaments for use in such treatments. The preferred therapeutic and diagnostic applications for the inventive compounds are discussed in detail below.

In a further embodiment of the present invention, there is provided a method of changing the lipophilicity, water solubility and/or the therapeutic index of a pharmaceutically active compound of formula I, as defined above, said method comprising forming an adduct of said compound of formula I and a thiol of the formula $HSR^3$, wherein $R^3$ is as herein before defined and the adduct is a compound of formula II, as defined above. In an embodiment, this method involves decreasing the lipophilicity and/or increasing the water solubility and/or the therapeutic index of the pharmaceutically active compound of formula I. In an alterative embodiment, the method involves decreasing the water solubility and/or increasing the lipophilicity and/or the therapeutic index of the pharmaceutically active compound of formula I.

The adduct may act as a pro-drug in the manner discussed above, or it may be pharmaceutically active in its own right.

In preferred embodiments of the inventive method, the adduct is formed via a Michael reaction between the unsaturated second compound and the thiol. Preferred methods of forming the adduct are described in the examples that follow.

A further —$SR^3$ group can, optionally, be added into a side chain bound to the cyclopentanone ring of compounds of formula II.

In a further aspect, the present invention provides an adduct as herein before defined, prepared or preparable by a method in accordance with the invention.

For the avoidance of doubt, it is confirmed that the term "alkenyl" denotes a group with one or more double bonds in its carbon skeleton and the term "alkynyl" denotes a group with one or more triple bonds in its carbon skeleton. It should also be understood that, for the purposes of this specification, alkynyl groups may include both double and single bonds in their carbon skeletons. Unless otherwise specified, groups referred to in this specification as alkyl, alkenyl or alkynyl groups can be straight chained or branched, or be or include cyclic groups. However, unless the contrary is indicated, they are preferably straight chained or branched.

Medical Uses for Compounds in Accordance with the Invention

The preferred uses for compounds in accordance with the invention include the treatment of disorders which can be treated in a host by the activation of a heat shock transcription factor (e.g. HSF1), by the induction of heat shock proteins (e.g. hsp70) and/or by the inhibition of NF-κB.

Certain preferred compounds in accordance with the invention can be used in therapeutic applications that involve activating HSF and inhibiting the activity of NF-κB. Thus, in accordance with the invention, such compounds can be used to treat diseases or conditions in which such activity is indicated or can be of advantage. They can also be used in the manufacture of medicaments for use in such treatments. Preferred therapeutic and diagnostic applications for such compounds are discussed below.

It should be appreciated that certain compounds in accordance with the invention do not exhibit activity in all of the respects discussed above. Such compounds, therefore, may only find use in those of the therapeutic and diagnostic applications detailed below where their properties are indicative of potential usefulness.

It should be appreciated that certain disorders, e.g. cancers, may be mediated by viruses and by non-viral factors. In the absence of any indication to the contrary, treatment of any given disorder is covered whether or not the disorder is mediated by viruses. It should also be appreciated that there is some overlap between the various categories of treatment discussed, i.e. the categories are not intended to be mutually exclusive.

1. Treatment of Viral-mediated Disorders

NF-κB is implicated in the pathogenesis of certain viral infections. It is known that heat shock proteins (e.g. HSP70) can offer protection against the pathogenesis of viral infection. Compounds in accordance with the invention may be active in reducing the replication of viruses.

Compounds in accordance with the invention may be useful in treating viral-mediated disorders. These include disorders mediated by RNA viruses, as well as disorders mediated by DNA viruses.

Examples of viral disorders that may be treated using compounds in accordance with the invention include the following.

Diseases caused by or associated with members of the Adenoviridae family, including (but not limited to): diarrhea or intussusception caused by or associated with enteric adenoviruses, upper or lower respiratory tract infections (including the common cold or pneumonia) caused by or associated with respiratory adenoviruses; conjunctivitis, keratitis or trachoma caused by or associated with adenovirus infection of the eye; tonsillar or kidney infections caused by or associated with adenoviruses Diseases caused by or associated with members of the Arenaviridae family, including (but not limited to): Lassa fever caused by Lassa fever virus; meningitis caused by or associated with lymphocytic choriomeningitis virus; hemorrhagic fevers including (but not limited to) those caused by Machupo virus, Junin virus, Sabia virus, Guanarito virus or Tacaribe virus.

Diseases caused by or associated with members of the Astroviridae family, including (but not limited to): diarrhea caused by or associated with astroviruses.

Diseases caused by or associated with members of the Bunyaviridae family, including (but not limited to): hemorrhagic fever with renal syndrome, hantavirus pulmonary syndrome, or other diseases caused by or associated with hantaviruses including (but not limited to) Hantaan virus, Puumala virus, Seoul virus, Dobrava virus, Sin Nombre virus, bayou virus, Black Creek canal virus, New York 1 virus, Monogahela virus, Andes virus, Laguna Negra virus; arbovirus infections including (but not limited to) La Crosse encephalitis, California encephalitis, or other bunyavirus infections; Rift Valley fever, sandfly fever, Uukuniemi or other arbovirus infections associated with phleboviruses; Crimean-Congo hemorrhagic fever or other infections caused by Nairoviruses Diseases caused by or associated with members of the Caliciviridae family or related agents, including (but not limited to): hepatitis caused by or associated with hepatitis E virus, diarrhea caused by or associated with caliciviruses or small round structured viruses Diseases caused by or associated with members of the Coronaviridae family, including (but not limited to): lower or upper respiratory tract infections (including the common cold) caused by or associated with coronaviruses; diarrhea, enterocolitis or gastroenteritis caused by or associated with coronaviruses or toroviruses.

Diseases caused by or associated with members of the Filoviridae family, including (but not limited to): hemorrhagic fevers caused by Ebola or Marburg viruses Diseases caused by or associated with members of the Flaviviridae family, including (but not limited to): arbovirus infections, fevers or encephalitides including (but not limited to) yellow fever, Kyansur Forest disease, Omsk hemorrhagic fever, other tick-borne encephalitis infections, Rocio, Japanese encephalitis, St. Louis encephalitis, West Nile virus infection, Murray Valley encephalitis, Dengue fever, or Dengue hemorrhagic fever caused by or associated with flaviviruses; hepatitis caused by or associated with hepatitis C virus Diseases caused by or associated with members of the Hepadnaviridae family, including (but not limited to): hepatitis caused by or associated with hepatitis B virus Diseases caused by or associated with members of the Herpesviridae family, including (but not limited to): orolabial herpes, genital herpes, herpetic dermatitis, herpetic whitlow, zosteriform herpes simplex, ocular disease, encephalitis or neonatal herpes caused by or associated with herpes simplex viruses types 1 or 2; chickenpox, shingles, zoster-associated pain, pneumonia, encephalitis, fetal infection or retinal necrosis caused by or associated with varicella-zoster virus; transplant rejection, congenital infection, infectious mononucleosis, retinitis or other diseases of the immunocompromised caused by or associated with cytomegalovirus; infectious mononucleosis, lymphomas, carcinomas or other cancers caused by or associated with Epstein-Barr virus; exanthem subitum, roseola infantum, pneumonitis or hepatitis caused by or associated with human herpesviruses 6 or 7; Kaposi's sarcoma or other neoplastic disease caused by or associated with human herpesvirus 8 (KSV).

Diseases caused by or associated with members of the Orthomyxoviridae family, including (but not limited to): influenza, pneumonia, other respiratory infections, myositis, myoglobinuria, or Reye's syndrome caused by or associated with influenza viruses A, B or C.

Diseases caused by or associated with members of the Papovaviridae family, including (but not limited to): papillomas, comdylomas, neoplasias and carcinomas caused by or associated with papillomaviruses; diseases caused by BKV or JCV viruses; progressive multifocal leukoencephalopathy caused by polyomaviruses.

Diseases caused by or associated with members of the Parvoviridae family, including (but not limited to): anemia, fever, fetal infection or hepatitis caused by or associated with parvorvirus B19.

Diseases caused by or associated with members of the Paramyxoviridae family, including (but not limited to): pneumonia, bronchiolitis, tracheobronchitis or croup caused by or associated with parainfluenza viruses; bronchiolitis or pneumonia caused by or associated with respiratory syncytial virus; encephalitis, measles or complications of measles including (but not limited to) pneumonia or sub-acute sclerosing panencephalitis (SSPE) caused by or associated with measles virus; mumps or complications of mumps including (but not limited to) orchitis or pancreatitis caused by or associated with mumps virus Diseases caused by or associated with members of the Picornaviridae family, including (but not limited to): hepatitis caused by or associated with hepatitis A virus; upper respiratory tract infections (including the common cold) caused by or associated with rhinoviruses or other respiratory picornaviruses; poliomyelitis caused by polioviruses; Bornholm disease, encephalitis, meningitis, herpangina, myocarditis, neonatal disease, pancreatitis, fever, conjunctivitis, chronic fatigue syndrome (ME) or hand, foot and mouth disease caused by coxsackieviruses or enteroviruses Diseases caused by or associated with members of the Poxviridae family, including (but not limited to): smallpox caused by smallpox virus; human forms of monkeypox or cowpox virus infections; infections with vaccinia virus including (but not limited to) complications of vaccination; orf or paravaccinia caused by parapoxviruses; molluscum contagiosum caused by molluscipoxviruses; infections with Tanapox virus.

Diseases caused by or associated with members of the Reoviridae family, including (but not limited to): diarrhea caused by or associated with rotaviruses Diseases caused by or associated with members of the Retroviridae family, including (but not limited to): acquired immune deficiency syndrome and associated disorders caused by or associated with human immunodeficiency virus (HIV); leukaemias, lymphomas, or myelopathies caused by or associated with HTLV viruses.

Diseases caused by or associated with members of the Rhabdoviridae family, including (but not limited to): rabies caused by rabies virus; other lyssavirus diseases including (but not limited to) those caused by Duvenhage or Mokola viruses.

Diseases caused by or associated with members of the Togaviridae family, including (but not limited to): rubella or congenital rubella syndrome caused by rubella virus; fever or encephalitis caused by eastern equine encephalitis virus, Venezuelan equine encephalitis virus, western equine encephalitis virus, Everglades virus or Semliki Forest virus; fever, rash, polyarthritis, myalgia or arthralgia caused by Sindbis virus, Ockelbo virus, Ross River virus, Barmah Forest virus, Chikungunya virus, O'nyong-nyong virus, Mayaro virus or Igo Ora virus.

Diseases caused by or associated with viroid-like agents, including (but not limited to): hepatitis caused by or associated with the delta agent (HDV).

Diseases caused by or associated with prions, including (but not limited to): Creutzfeld-Jakob disease (CJD), new variant CJD, GSS, and fatal familial insomnia.

Compounds of the present invention may be particularly useful in treating vital and other disorders affecting aquatic organisms (e.g. fish, crustaceans, etc.). Such disorders include disorders mediated by the snout ulcer virus, by the iridovirus, by the lymphocystis disease virus, etc.

Compounds in accordance with the invention may therefore be used in aquaculture. They may be used in food for aquatic organisms. Such food is within the scope of the present invention. It will generally be sold in sealed containers and labelled appropriately (e.g. as fish food, food for crustaceans, food for aquatic organisms, etc.). Alternatively, compounds in accordance with the invention may be used for water treatment or for direct application to aquatic organisms. Such compounds do not therefore need to be present in foodstuffs in order to be useful in aquaculture.

2. Treatment of Bacterial-mediated Disorders

NF-κB is activated in response to bacterial infections.

Compounds in accordance with the invention can be useful in treating disorders arising from such infections, e.g. in treating NF-κB stimulated inflammation. Most commonly this will arise due to infection with gram negative bacteria. However it may also arise due to infection with gram positive bacteria (e.g. *S. aureus*).

3. Treatment of Disorders Mediated by Radiation

NF-κB is activated in response to radiation (e.g. UV-radiation).

Compounds in accordance with the invention can be useful in treating disorders mediated by radiation. Such disorders include cell and tissue trauma, cell and tissue ageing and cancer (e.g. skin cancer).

4. Treatment of Inflammation and of Disorders of the Immune System

NF-κB is activated in response to inflammatory cytokines. It is believed to be an early mediator of the immune and inflammatory responses.

Compounds in accordance with the invention can be useful in treating immune disorders (e.g. auto-immune disorders) and in treating inflammatory disorders. Examples of specific inflammatory disorders and disorders of the immune system that may be treated with such compounds include psoriasis, rheumatoid arthritis, multiple sclerosis, adult respiratory distress syndrome, hepatitis and/or cirrhosis, vascular inflammation (including lupus erythematosis disseminate), and inflammatory disorders of the gastro-intestinal tract (e.g. ulcers). Preferred amongst these uses is the treatment of psoriasis, particularly by the topical application of a compound in accordance with the invention formulated in a suitable composition, such as a cream, ointment or the like.

5. Treatment of Ischemia and Arteriosclerosis

NF-κB has been implicated in the pathogenesis of ischemia and anteriosclerosis. Compounds in accordance with the invention are therefore useful in treating such disorders, including reperfusion damage (e.g. in the heart or brain) and cardiac hypertrophy.

6. Treatment of Disorders Involving Cell Proliferation

NF-κB is implicated in cell proliferation.

Compounds in accordance with the invention can be useful as anti-proliferatives. They are therefore useful in treating inflammatory granulomas, neointimal proliferation in arterial and venous restenosis, and cancers (including lymphomas, leukemias, sarcomas, carcinomas and melanomas).

7. Treatment of Disorders Involving Damage to or Killing of Cells

Heat shock proteins are known to provide a cytoprotective effect.

Compounds in accordance with the invention can be useful in treating disorders involving damage to or killing of cells.

These disorders include chemical toxicity (e.g. due to ingestion of toxins, such as paraquat, or to overdosing with medicaments, such as paracetamol), oxidative cell damage, cell and tissue ageing trauma, hepatitis diabetes and the effect of burns. The inventive compounds, also, can be used to combat the effects of ageing in a human or animal, and to promote wound healing.

Other conditions of this general nature, that can be treated using compounds of the present invention, include oxidative stress and degenerative diseases, especially neuro-degenerative diseases such as BSE, new variant CJD and Alzheimer's disease.

8. Other Treatments

Cyclopentenone prostaglandins are of known utility in stimulating peroxisome proliferator activated receptors (PPARs). Compounds in accordance with the invention, thus, can be useful in treating diabetes (including complications arising therefrom). Such compounds can also be used in the treatment of disorders in which calcium loss or deficiency is implicated or involved (including bone disorders, skeletal disorders, dental disorders, developmental disorders, etc.).

Routes of Administration for Compounds in Accordance with the Invention

A medicament will usually be supplied as part of a pharmaceutical composition, which may include a pharmaceutically acceptable carrier. This pharmaceutical composition will generally be provided in a sterile form. It may be provided in unit dosage form. It will generally be provided in a sealed container, and can be provided as part of a kit. Such a kit is within the scope of the present invention. It would normally (although not necessarily) include instructions for use. A plurality of unit dosage forms may be provided.

Pharmaceutical compositions within the scope of the present invention may include one or more of the following: preserving agents, solubilising agents, stabilising agents, wetting agents, emulsifiers, sweeteners, colourants, odourants, salts (compounds of the present invention may themselves be provided in the form of a pharmaceutically acceptable salt, as explained in greater detail below), buffers, coating agents or antioxidants. They may also contain other therapeutically active agents in addition to a compound of the present invention.

Compounds of the present invention may themselves be provided in any suitable form, i.e. they may be used as such or may be used in the form of a pharmaceutically effective derivative. For example they may be used in the form of a pharmaceutically acceptable salt or hydrate. Pharmaceutically acceptable salts include alkali metal salts (e.g. sodium or potassium salts), alkaline earth metal salts (e.g. calcium or magnesium salts) aluminium salts, zinc salts, ammonium salts (e.g. tetra-alkyl ammonium salts), etc. Inorganic acid addition salts (e.g. hydrochlorides, sulphates, or phosphates) or organic acid addition salts (e.g. citrates, maleates, fumarates, succinates, lactates, propionates or tartrates) may be used.

Pharmaceutical compositions of the present invention may be provided in controlled release form. This can be achieved by providing a pharmaceutically active agent in association with a substance that degrades under physiological conditions in a predetermined manner. Degradation may be enzymatic or may be pH-dependent.

Pharmaceutical compositions may be designed to pass across the blood brain barrier (BBB). For example, a carrier such as a fatty acid, inositol or cholestrol may be selected that is able to penetrate the BBB. The carrier may be a substance that enters the brain through a specific transport system in brain endothelial cells, such as insulin-like growth factor I or II. The carrier may be coupled to the active agent or may contain/be in admixture with the active agent. Liposomes can be used to cross the BBB. WO91/04014 describes a liposome delivery system in which an active agent can be encapsulated/embedded and in which molecules that are normally transported across the BBB (e.g. insulin or insulin-like growth factor I or II) are present on the liposome outer surface. Liposome delivery systems are also discussed in U.S. Pat. No. 4,704,355.

A pharmaceutical composition within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) routes. Such a composition may be prepared by any method known in the art of pharmacy, for example by admixing one or more active ingredients with a suitable carrier. In preferred embodiments, compounds in accordance with the invention are formulated into oral dosage forms and, therefore, are preferably provided in tablet or capsule form.

Different drug delivery systems can be used to administer pharmaceutical compositions of the present invention, depending upon the desired route of administration. Drug delivery systems are described, for example, by Langer (Science 249, 1527–1533 (1991)) and Illum and Davis (Current Opinions in Biotechnology 2m 254–259 (1991)). Different routes of administration for drug delivery will now be considered in greater detail.

(i) Oral Administration

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, maize starch or derivatives thereof, stearic acid or salts thereof. Soft gelatine capsules may comprise vegetable oils, waxes, fats, semi-solid, or liquid polyols etc. Solutions and syrups may comprise water, polyols and sugars. For the preparation of suspensions, oils (e.g. vegetable oils) may be used to provide oil-in-water or water-in-oil suspensions.

An active agent intended for oral administration may be coated with or admixed with a material that delays integration and/or absorption of the active agent in the gastrointestinal tract (e.g. glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

(ii) Transdermal Administration

Pharmaceutical compositions adapted for transdermal administration may be provided as discrete patches intended to remain in intimate contact with the epidermis of the recipient for a prolonged period of time. For example, the active ingredient may be delivered from the patch by iontophoresis. (Iontophoresis is described in *Pharmaceutical Research,* 3(6):318 (1986).

(iii) Topical Administration

Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. Here the active ingredient can be dissolved or suspended in a suitable carrier, e.g. in an aqueous solvent. Pharmaceutical compositions adapted for topical administration in the mouth include lozenges, pastilles and mouthwashes.

(iv) Rectal Administration

Pharmaceutical compositions adapted for rectal administration may be provided as suppositories or enemas.

(v) Nasal Administration

This includes not only administration to the nasal cavity, but also administration via the nasal cavity to another location, e.g. to the lungs.

Pharmaceutical compositions adapted for nasal administration may use solid carriers, e.g. powders (preferably having a particle size in the range of 20 to 500 microns). Powders can be administered in the manner in which snuff is taken, i.e. by rapid inhalation through the nose from a container of powder held close to the nose. Compositions adopted for nasal administration may alternatively use liquid carriers, e.g. include nasal sprays or nasal drops. These may comprise aqueous or oil solutions of the active ingredient.

Compositions for administration by inhalation may be supplied in specially adapted devices, e.g. in pressurised aerosols, nebulizers or insufflators. These devices can be constructed so as to provide predetermined dosages of the active ingredient.

(vi) Vaginal Administration

Pharmaceutical compositions adapted for vaginal administration may be provided as pessaries, tampons, creams, gels, pastes, foams or spray formulations.

(vii) Parenteral Administration

Pharmaceutical compositions adapted for parenteral administration include aqueous and non-aqueous sterile injectable solutions or suspensions. These may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampoules and vials, and may be stored in a freeze-dried (lyophilised) condition requiring only the addition of a sterile liquid carrier, e.g. sterile water for injections, immediately prior to use. Extemporaneous injection solutions and suspensions may be prepared from sterile powders, granules and tablets.

From the above description it will be appreciated that compositions of the present invention can be formulated in many different ways.

Dosages

Dosages of a compound of the present invention can vary between wide limits, depending upon the nature of the treatment, the age and condition of the individual to be treated, etc. and physician will ultimately determine appropriate dosages to be used.

However, without being bound by any particular dosages, a daily dosage of a compound of the present invention of from 10 µg to 100 mg/kg body weight may be suitable.

More preferably the dosage is from 5 to 50 mg/kg body weight/day. The dosage may be repeated as often as appropriate. If side effects develop, the amount and/or frequency of the dosage can be reduced, in accordance with good clinical practice.

Research Uses

Compounds of the present invention are useful in research. For example, they can be used as research tools for the analysis of one or more of the following: HSF, NF-κB, the heat shock response, viral replication, viral-mediated disorders, bacterial-mediated disorders, disorders mediated by radiation (e.g. by UV-radiation), inflammatory disorders, disorders of the immune system, ischemia, arteriosclerosis, disorders involving cell proliferation (e.g. cancers), disorders involving damage to, or killing of cells (e.g. oxidative cell damage), and diabetes.

Other Uses

Compounds of the present invention can also be useful in treating plant viral disorders. Given that the basic mechanism of the heat shock response are believed to operate in a similar fashion in plants and animals and that it is reasonable to expect that direct antiviral effects will be produced by the compounds of invention in a similar fashion in plants and animals, the use of compounds of the present invention in treating viral infections of plants is within the scope of the present invention. These infections include, but are not limited to, infections by plants of geminiviruses, rhabdoviruses, caulimoviruses, bromoviruses, tobramoviruses, potyviruses and potexviruses. The use of compounds of the present invention in treating infections by viroids (including, but not limited to, potato spindle tumour viroid, hop stunt viroid, and coconut cadang-cadang viroid) is also within the scope of the invention.

Compounds of the present invention may be particularly useful in treating viral and other disorders affecting aquatic organisms (e.g. fish, crustaceans, etc.). Such disorders include disorders mediated by the snout ulcer virus, iridovirus, lymphocystis disease virus, infectious salmon anaemia, nodaviruses etc.

Compounds of the present invention may therefore be used in aquaculture. They may be used in food for aquatic organisms. Such food is within the scope of the present invention. It will generally be sold in sealed containers and labelled appropriately (e.g. as fish food, food for crustaceans, food for aquatic organisms, etc.). Alternatively, compounds of the present invention may be used for water treatment or for direct application to aquatic organisms. Such compounds do not therefore need to be present in foodstuffs in order to be useful in aquaculture.

EXAMPLES

Example 1

(a) Synthesis of Compounds According to the Invention—the Tandem Pauson-Khand, Peterson Routes to Dienones

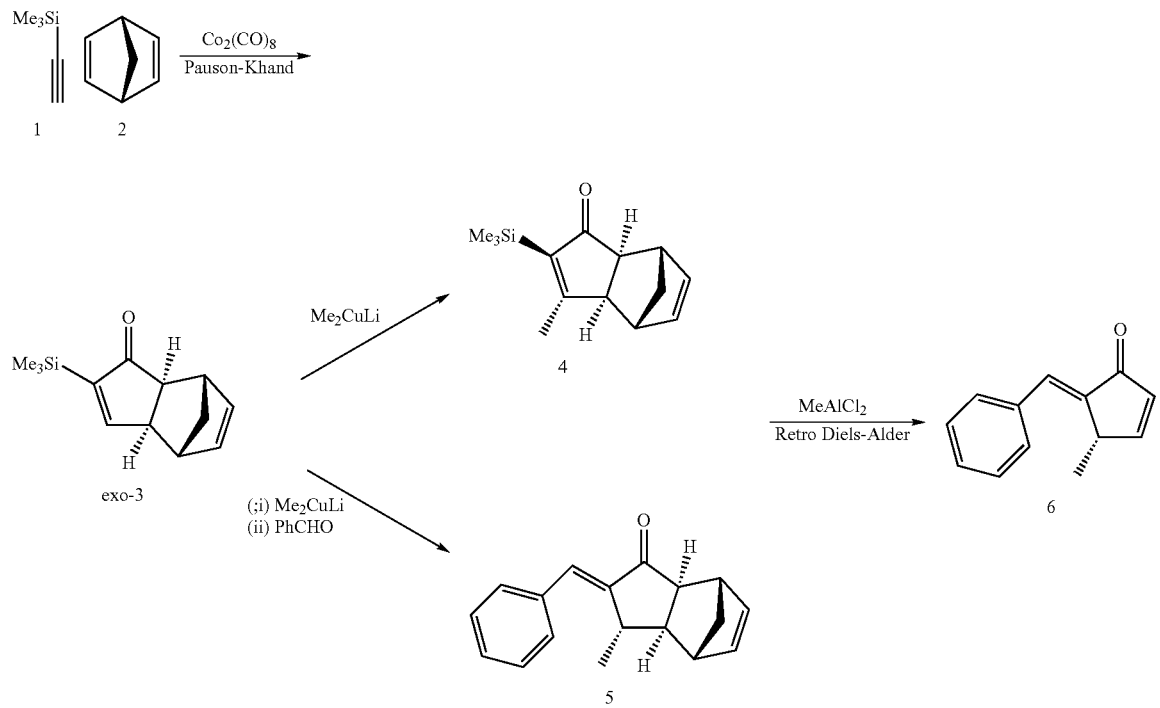

Pauson-Khand Reaction (1+2→3):

Synthesis of exo-2-trimethylsilanyl-3a,4,7,7a-tetrahydro-4,7-methano-inde-1-one 3: Under nitrogen at room temperature a solution of trimethylsilanylacetylene 1 (1.44 cm$^3$, 10.19 mmol, 1 eq.) in DCM (40 cm$^3$) was treated with Co$_2$(CO)$_8$ (3.50 g, 10.24 mmol, 1 eq.). Stirring was continued for 24 hours. TLC analysis (Hexane) indicated formation of the corresponding cobalt complex. Norbornadiene (1.2 cm$^3$, 11.12 mmol, 1.1 eq.) was added and the reaction was cooled to 0° C. and NMO (11.93 g 101.84 mmol, 10 eq.) was added in five portions. Stirring was continued for 3 days before silica (ca. 25 g) was added and the solvent was removed under reduced pressure. Purification by flash column chromatography (Hex-Et$_2$O; 19:1) afforded initially exo-3 (1.20 g, 54%) followed by endo-3 (0.130 g, 6%) [exo-3:endo-3; 9:1]. $R_f$=0.25 (Hex-Et$_2$O; 19:1) [endo-3; $R_f$=0.15 (Hex-Et$_2$O; 19:1)]; $\delta_H$ (400 MHz, CDCl$_3$) −0.17 (9H, s, CH$_3$), 1.05 (1H, d, J 11.25 Hz, CH$_2$), 1.22 (1H, d, J 11.25 Hz, CH$_2$), 2.01 (1H, d, J 6.25 Hz, CH), 2.52 (1H, s, CH), 2.72–2.74 (1H, m, CH), 2.80 (1H, s, CH), 6.11–6.18 (1H, m, CH), 6.21–6.30 (1H, m, CH), 7.65 (1H, d, J 2.5 Hz, CH); $\delta_C$ (100 MHz, CDCl$_3$) −2.1, 41.1, 42.8, 43.7, 51.9, 53.2, 137.2, 138.1, 152.0, 172.7, 213.0; m/z (CI) 219 (MH$^+$, 100%); Found C, 71.50; H, 8.31%, C$_{13}$H$_{18}$SiO requires C, 71.60; H, 8.30%.

Tandem Conjugate-Addition Peterson Olefination (3→5):

3-Methyl-2-[1-phenyl-meth-(E)-ylidene]-2,3,3a,4,7,
7a-hexahydro-4,7-methano-inden-1-one 5

At −78° C. under nitrogen a slurry of CuI (636 mg, 3.34 mmol, 1.5 eq.) in Et$_2$O (25 cm$^3$) was treated dropwise with a 1.6 M solution of MeLi in hexane (4.2 cm$^3$, 6.72 mmol, 3.0 eq.). The reaction was warmed to −10° C. over a period of 2 h. This solution was cooled to −20° C. before a cooled (−20° C.) solution of the enone 3 (485 mg, 2.23 mmol, 1 eq.) in Et$_2$O (25 cm$^3$) was added dropwise. The flask containing 3 was washed, Et$_2$O (5 cm$^3$) and this was transferred to the reaction mixture. Stirring was continued for 1.5 h during which time the temperature rose to 10° C. Upon cooling to −78° C., benzaldehyde (0.35 cm$^3$, 3.44 mmol, 1.5 eq.) was added. The reaction was stirred for 3 h and warmed from −78° C. to 10° C. NH$_4$Cl (25 cm$^3$) was added and the resultant aqueous phase was further extracted with Et$_2$O (3×25 cm$^3$). The combined organic extracts were dried over MgSO$_4$, filtered and the solvent removed in vacuo. The crude product was purified by flash column chromatography (Hex-Et$_2$O; 19:1) affording 5 as a colourless solid (520 g, 93%). Recrystallisation from hexane gave crystals of 5 suitable for X-ray crystallography. R$_f$=0.15 (Hex-Et$_2$O; 19:1); δ$_H$(400 MHz, CDCl$_3$) 1.25 (3H, d, J 7.0 Hz, CH$_3$), 1.28 (1H, dt, J 1.5, 9.5 Hz, CH$_2$), 1.36 (1H, d, J 9.5 Hz, CH$_2$), 1.93 (1H, d, J 7.5 Hz, CH), 2.48 (1H, d, J 7.5 Hz, CH), 2.86 (1H, s, CH), 3.12 (1H, s, CH), 3.19 (1H, q, J 7.0 Hz, CH), 6.18–6.26 (2H, m, CH), 7.28 (1H, d, J 2.0 Hz, CH), 7.34–7.44 (3H, m, ArH), 7.57 (2H, d, J 7.5 Hz, ArH); δ$_C$ (100 MHz, CDCl$_3$) 21.2, 38.9, 43.2, 48.5, 49.2, 49.5, 53.3, 128.8, 129.4, 130.7, 133.4, 135.9, 137.6, 139.0, 145.1, 209.0; m/z (EI) 250 (M$^+$, 25%), 183 (100%), 156 (50%), 141 (50%), 128 (40%), 115 (70%), 91 (50%), 66 (90%; Found C, 85.95; H, 7.42%, C$_{18}$H$_{18}$O requires C, 86.36; H, 7.25%.

Retro-Diels/Alder (5→6):

4-Methyl-5-[1-phenyl-meth-(E)-ylidene]-cyclopent-
2-enone 6 (CTC-150)

Under nitrogen a solution of 5 (250 mg, 1 mmol, 1 eq.) and maleic anhydride (490 mg, 5 mmol, 5 eq.) in DCM (10 cm$^3$) was treated with a 1.0 M solution of MeAlCl$_2$ in hexane (1.1 cm$^3$, 1.1 mmol, 1.1 eq.). This mixture was heated to reflux for 5 h. Silica (ca. 2.5 g) was added and the solvent was removed under reduced pressure. Flash column chromatography (Hex-EtOAc; 3:1) gave the title compound 6 (138 mg, 75%) as a colourless solid. R$_f$=0.5 (Hex-EtOAc; 3:1); δ$_H$ (400 MHz, CDCl$_3$) 1.22 (3H, d, J 7.0 Hz, CH$_3$), 3.84–4.00 (1H, m, CH), 6.40 (1H, dd, J 1.75, 5.75 Hz, CH), 7.39–7.44 (4H, ArH), 7.54 (2H, d, J 7.0 Hz, ArH), 7.60 (1H, ddd, J 1.0, 2.5, 5.75 Hz, CH); δ$_C$(100 MHz, CDCl$_3$) 16.3, 38.8, 128.7, 129.3, 130.6, 131.7, 133.6, 134.8, 138.3, 163.9, 197.4; Found C, 84.66; H, 6.60%, C$_{13}$H$_{12}$O requires C, 84.78; H, 6.57%.

(b) Synthesis of Compound CTC-191 (8) Using the Method Described in Example 1 (a)

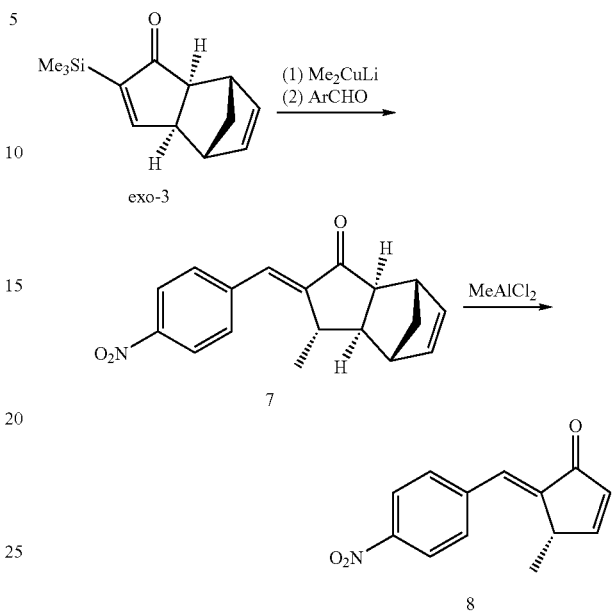

Preparation of 4-nitrobenzaldehyde Derivative (7) from (3); Steps 3→7:

Following the procedure described above, 3 (485 mg, 2.22 mmol, 1 eq.), prepared in the manner described above, in Et$_2$O (10 cm$^3$) was treated with a solution of Me$_2$CuLi in Et$_2$O (25 cm$^3$) generated from CuI (636 mg, 3.34 mmol, 1.5 eq.) and a 1.6 M solution of MeLi in Et$_2$O (4.2 cm$^3$, 6.72 mmol, 3 eq.). After TLC indicated formation of the conjugate adduct 4-nitrobenzaldehyde (504 mg, 3.33 mmol, 1.5 eq.) in benzene (5 cm$^3$) [washed with THF (5 cm$^3$)]. Standard work-up as above followed by flash column chromatography (Hex-EtOAc; 3:1) afforded adduct 7 (600 mg, 92%) as a yellow crystalline solid. Analytically pure 7 was obtained on recrystallisation from EtOAc. R$_f$=0.35 (Hex-EtOAc; 3:1); δ$_H$ (400 MHz, CDCl$_3$) 1.24 (3H, d, J 7.0 Hz, CH$_3$), 1.30–1.35 (2H, m, CH$_2$), 2.01 (1H, d, J 7.5 Hz, CH), 2.54 (1H, d, J 7.5 Hz, CH), 2.92 (1H, s(br), CH), 3.14 (1H, s (br), CH), 3.22 (1H, q, J 7.0 Hz, CH), 6.23 (1H, dd, J 2.5, 5.5 Hz, CH), 6.28 (1H, dd, J 3.0, 5.5 Hz, CH), 7.28 (1H, d, J 2.25 Hz, CH), 7.72 (2H, d, J 8.5 Hz, ArH), 8.27 (2H, d, J 8.5 Hz, ArH); δ$_C$ (100 MHz, CDCl$_3$) 21.1, 38.9, 43.5, 48.6, 49.2, 49.4, 53.3, 123.9, 130.2, 130.9, 137.5, 139.0, 141.3, 147.5, 148.8, 208.6; m/z (CI) 313 (MNH$_4^+$, 80%), 296 (MH$^+$, 35%), 266 (90%), 247 (65%), 230 (MH-C$_5$H$_6^+$, 100%); Found 296.12835, C$_{18}$H$_{18}$NO$_3$ requires 296.12866; Found C, 72.73; H, 5.75; N, 4.52%, C$_{18}$H$_{17}$NO$_3$ requires C, 73.21; H, 5.80; N, 4.74%.

Preparation of CTC-191 (8) from Compound (7)

Following the general procedure described adduct 7 (220 mg, 0.746 mmol, 1 eq.) and maleic anhydride (365 mg, 3.72 mmol, 5 eq.) in DCM (20 cm$^3$) was treated with a 1.0 M solution of MeAlCl$_2$ in hexane (0.75 cm$^3$, 0.75 mmol, 1 eq.) and heated to reflux for 3.5 h. The reaction was cooled before Et$_2$O (50 cm$^3$) and 0.5 M NaOH (50 cm$^3$) were added. The resultant aqueous layer was extracted with Et$_2$O (2×50 cm$^3$) and the combined organic extracts were dried over MgSO$_4$. Filtration, pre-absorption onto silica (ca. 5 g)

and purification by flash column chromatography (Hex-EtOAc; 3:1) afforded the cyclopentenone 8 (145 mg, 85%) as a pale yellow solid. $R_f$=0.30 (Hex-EtOAc; 3:1); $\delta_H$(400 MHz, CDCl$_3$) 1.20 (3H, d, J 7.5 Hz, CH$_3$), 3.93–4.01 (1H, m, CH), 6.47 (1H, dd, J 1.75, 6.0 Hz, CH), 7.42 (1H, s, CH), 7.66 (1H, dd, J 2.5, 6.0 Hz, CH), 7.68 (2H, d, J 8.5 Hz, ArH), 8.28 (2H, d, J 8.5 Hz, ArH); $\delta_C$(100 MHz, CDCl$_3$) 16.4, 38.6, 123.9, 128.8, 130.8, 131.2, 133.6, 141.2, 141.6, 164.3, 196.6; m/z (CI) 247 (MNH$_4^+$, 5%), 230 (MH$^+$, 10%), 200 (100%); Found 230.08171, C$_{13}$H$_{12}$NO$_3$ requires 230.08164, (−0.3 ppm); Found C, 67.93; H, 4.85; N, 6.10%, C$_{13}$H$_{11}$NO$_3$ requires C, 69.09; H, 4.84; N, 6.11%.

(c) Synthesis of Enone (10) Using the Method Described in Example 1 (a)

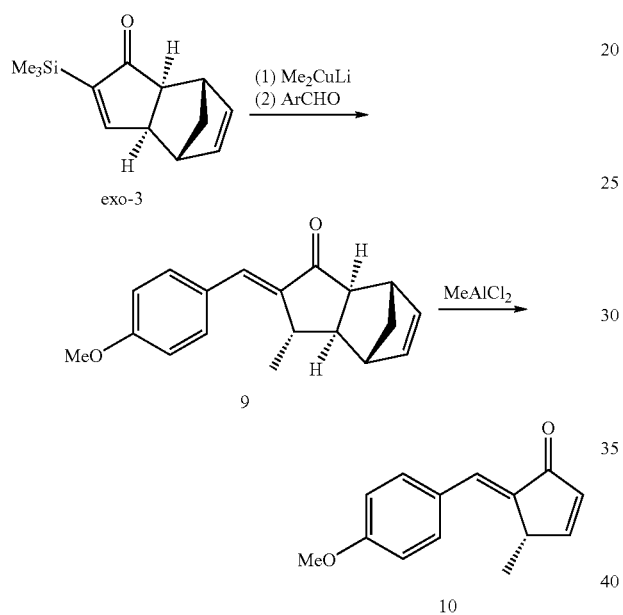

Preparation of p-methoxybenzaldehyde Derivative (9) from Compound 3

Following the general procedure outlined above a solution of Me$_2$CuLi in Et$_2$O (25 cm$^3$); prepared from CuI (636 mg, 3.33 mmol, 1.5 eq.) and a 1.6 M solution of MeLi in hexanes (4.2 cm$^3$, 6.72 mmol, 3.0 eq.), was treated with 3 (485 mg, 2.22 mmol, 1 eq.), prepared in the manner described above. On formation of the conjugate adduct (judged by TLC analysis) p-methoxybenzaldehyde (455 mg, 3.34 mmol, 1.5 eq.). Following standard work-up described above and purification by flash column chromatography (Hex-EtOAc; 3:1) the adduct 9 (281 mg, 45%) was isolated as a colourless solid. $R_f$=0.35 (Hex-EtOAc; 3:1); $\delta_H$ (400 MHz, CDCl$_3$) 1.25 (3H, d, J 7.25 Hz, CH$_3$), 1.23–1.28 (1H, m, CH$_2$), 1.94 (1H, d, J 7.5 Hz, CH), 7.48 (1H, d, J 7.5 Hz, CH), 2.85 (1H, s, CH), 3.09–3.18 (2H, m, CH), 3.86 (3H, s, CH$_3$), 6.20 (1H, dd, J 3.0, 5.5 Hz, CH), 6.23 (1H, dd, J 3.0, 5.5 Hz, ArH), 6.95 (2H, d, J 8.5 Hz, ArH), 7.28 (1H, s, CH), 7.54 (2H, d, J 8.5 Hz, ArH); m/z (CI) 281 (MNH$_4^+$, 70%), 215 (MH-C$_5$H$_6^+$, 100%); Found 281.15390, C$_{19}$H$_{21}$O$_2$ requires 281.15414, (−0.9 ppm); Found C, 81.60; H, 7.31%, C$_{19}$H$_{20}$O$_2$ requires C, 81.43; H, 7.14%.

Preparation of Enone (10) from p-methoxybenzaldehyde Derivative (9)

Following the standard retro-Diels-Alder procedure described 9 (350 mg, 1.25 mmol, 1 eq.) and maleic anhydride (613 mg, 6.26 mmol, 5 eq.) in DCM (25 cm$^3$) was treated with a 1.0 M solution of MeAlCl$_2$ in hexane (1.25 cm$^3$, 1.25 mmol, 1 eq.) and heated to reflux for 35 h. Et$_2$O (50 cm$^3$) and 0.5 M NaOH (50 cm$^3$) were added. The resultant aqueous layer was extracted with Et$_2$O (2×50 cm$^3$) and the combined organic extracts were dried over MgSO$_4$. Filtration, pre-absorption onto silica (ca. 5 g) and purification by flash column chromatography (Hex-EtOAc; 3:1) afforded 10 (182 mg, 68%) as a colourless solid. $R_f$=0.25 (Hex-EtOAc; 3:1); $\delta_H$ (400 MHz, CDCl$_3$) 1.21 (3H, d, J 7.5 Hz, CH$_3$), 3.83–3.92 (1H, m, CH), 3.85 (3H, s, CH$_3$), 6.38 (1H, dd, J 2.0, 6.0 Hz, CH), 6.90 (2H, d, J 8.5 Hz, ArH), 7.34 (1H, s, CH), 7.49 (2H, d, J 8.5 Hz, ArH), 7.57 (1H, ddd, J 1.0, 2.5, 6.0 Hz, ArH); $\delta_C$ (100 MHz, CDCl$_3$) 16.3, 38.8, 55.3, 114.2, 127.1, 131.4, 133.5, 136.1, 160.5, 163.4, 197.5; m/z (CI) 214 (MH$^+$, 100%), 186 (75%), 171 (100%); Found 214.09934, C$_{14}$H$_{14}$O$_2$ requires 214.09937, (−0.1 ppm).

Example 2

Preparation of 2-Oxa-3-azabicyclo[2.2.1]hept-5-ene-3-carboxylic acid tert-butyl ester (2)

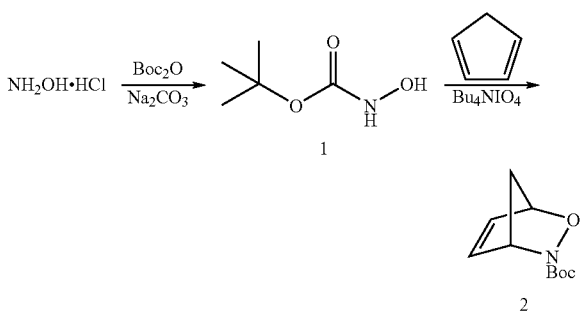

Water (5 cm$^3$) and sodium carbonate (23.9 g, 0.23 mol) were added to a suspension of hydroxylamine hydrochloride (24.0 g, 0.35 mol) in diethyl ether (150 cm$^3$). The suspension was stirred at room temperature for 1 hour, then cooled to 0° C. Subsequently, a solution of di-tert-butyl dicarbonate (50.2 g, 0.23 mol) in diethyl ether (50 cm$^3$) was added dropwise over 30 minutes and the suspension was allowed to warm up to room temperature, then stirred for 3 hours. Upon completion of reaction, the mixture was filtered and washed with ether (2×100 cm$^3$). The filtrate was evaporated to dryness to yield a colourless oil. Upon addition of cyclohexane, compound 1 was crystallised as colourless needles (27.2 g, 0.20 mol, 89%, 2 crops). Tetra-n-butylammonium periodate (2.0 g, 4.67 mmol) was added to a solution of freshly cracked cyclopentadiene (0.46 g, 6.97 mmol) in dichloromethane (15 cm$^3$) tert-Butyl-N-hydroxycarbamate 1 (0.62 g, 4.67 mmol, 1 eq.) was then added portionwise over 5 minutes and the solution was stirred for 1 hour at room temperature. Upon completion of reaction, the organic solution was washed successively with sodium thiosulfate (10% aq. soln., 2×50 cm$^3$) and sodium hydrogen carbonate (sat'd. aq., 80 cm$^3$), then dried over anhydrous magnesium sulfate, filtered and concentrated to give a crude black oil. Flash chromatography (SiO$_2$, 20% ethyl acetate in petrol) gave the bicyclic adduct 2 (0.73 g, 3.71 mmol, 79%) as a yellow oil, which solidified upon standing in the freezer; $\delta_H$ (400 MHz, CDCl$_3$) 6.41 (2H, m, CH=CH), 5.20 (1H, m, CHNBoc), 4.98 (1H, m, CHON), 1.98 (1H, dt, J 8.5 & 1.9 Hz, CHH), 1.73 (1H, m, CHH), 1.46 (9H, s, CO$_2$C(CH$_3$)$_3$); $\delta_C$ (100 MHz, CDCl$_3$) 158.6 (s), 134.1 (d), 132.9 (d), 83.5 (d), 81.8 (s), 65.0 (d), 48.1 (t), 28.2 (q).

J 5.7 & 0.7 Hz, CH=CHC=O), 4.94 (2H, m, NH+CHNH), 2.83 (1H, m, CHH), 2.17 (1H, m, CHH), 1.45 (9H, s, CO$_2$C(CH$_3$)$_3$); $\delta_C$ (100 MHz, CDCl$_3$) 206.9 (s), 162.6 (d), 155.5 (s), 135.5 (d), 80.6 (s), 51.5 (d), 42.7 (t), 28.7 (q); m/z (EI) Found [M]$^+$ 197.1057 ([M]$^+$C$_{10}$H$_{15}$NO$_3$ requires 197.1052).

Example 3

Preparation of (4-Hydroxycyclopent-2-enyl)-carbamic acid tert-butyl ester (3)

Example 5

Preparation of (5-iso-Butylidene-4-oxocyclopent-2-enyl)-carbamic acid tert-butyl ester (5) (CTC-121)

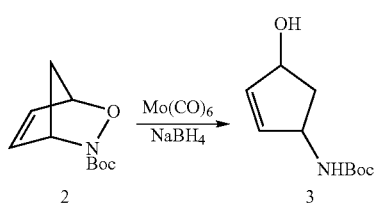

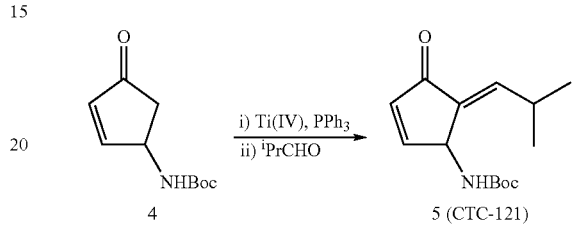

Molybdenum hexacarbonyl (1.46 g, 5.53 mmol) was added to a solution of the bicycle 2 (0.70 g, 3.55 mmol) in a 7:1 mature of acetonitrile and water (24 cm$^3$). The suspension was stirred for 10 minutes at room temperature, then sodium borohydride (0.07 g, 1.85 mmol) was added and the suspension was heated under reflux for 3 hours. Upon completion of reaction, the mixture was allowed to cool to room temperature, filtered through a celite plug, and evaporated to dryness to give a dark oil. Flash chromatography (SiO$_2$, 50% ethyl acetate in petrol) gave the alcohol 3 (0.46 g, 2.31 mmol, 65%) as a colourless oil; $\delta_H$ (200 MHz, CDCl$_3$) 5.97 (1H, m, CH=CH), 5.85 (1H, dt, J 5.8 & 1.8 Hz, CH=CH), 4.80 (1H, m), 4.69 (1H, m), 4.42 (1H, m), 2.74 (2H, dt, J 14.3 & 7.1 Hz, CH$_2$), 1.55 (1H, m, OH), 1.44 (9H, s, CO$_2$C(CH$_3$)$_3$); m/z (CI) Found [MH]$^+$ 200.1285 ([MH]$^+$ C$_{10}$H$_{18}$NO$_3$ requires 200.1287).

Triphenylphosphine (262 mg, 1.00 mmol) was added to a solution of the enone 4 (197 mg, 1.00 mmol) in anhydrous dichloromethane (3 cm$^3$). The solution was cooled to −50° C., then titanium (IV) isopropoxide (148 □L, 0.50 mmol) and titanium (IV) chloride (55 µL, 0.50 mmol) were successively added to the mixture. After 15 minutes stirring at −50° C., isobutyraldehyde (0.27 cm$^3$, 3.00 mmol) was added and the mixture was allowed to warm up to room temperature, then stirred for 17 hours at room temperature. Upon completion of reaction, the mixture was quenched with potassium carbonate (10% aq. soln., 10 cm$^3$) and extracted with diethyl ether (3×10 cm$^3$). The combined organic layers were dried over anhydrous magnesium sulfate, filtered and evaporated to dryness to give a yellow oil. Flash chromatography (SiO$_2$, 20% ethyl acetate in petrol) gave the dieneone 5 (20 mg, 0.08 mmol, 8%) as a white solid; δH (400 MHz, CDCl$_3$) 7.40 (1H, ddd, J 6.0, 2.5 & 0.8 Hz, CH=CHC=O), 6.49 (1H, d, J 10.7 Hz, C=CH), 6.38 (1H, dd, J 6.0 & 1.7 Hz, CH=CHC=O), 5.46 (1H, m, NM), 4.56 (1H, m, CHNH), 2.75 (1H, m, CH(CH$_3$)$_2$), 1.47 (9H, s, CO$_2$C(CH$_3$)$_3$), 1.06 (6H, m, CH(CH$_3$)$_2$); m/z (CI) Found [MH]$^+$ 252.1596 ([H]$^+$ C$_{14}$H$_{22}$NO$_3$ requires 252.1600).

Example 4

Preparation of (4-Oxocyclopent-2-enyl)-carbamic acid tert-butyl ester (4) (CTC-132)

Example 6

Preparation of (2S,4R)-Acetic acid 4-tert-butoxycarbonylaminocyclopent-2-enyl ester 6 and (2S,4R)-(4-Hydroxycyclopent-2-enyl)-carbamic acid tert-butyl ester ((−)-3)

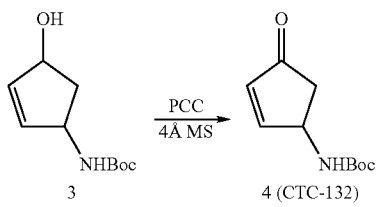

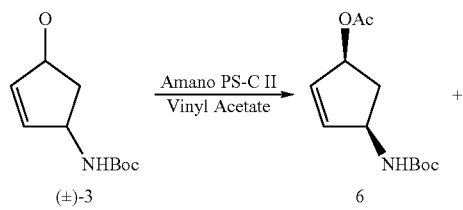

4 Å powdered, activated, molecular sieves (0.5 g) and pyridinium chlorochromate (0.60 g, 2.8 mmol) were successively added to a solution of the alcohol 3 (0.46 g, 2.31 mmol) in anhydrous dichloromethane (20 cm$^3$). The suspension was stirred for 2 hours at room temperature. Upon completion of reaction, the mixture was filtered over a short silica gel column (50% ethyl acetate in petrol) to give the ketone 4 (0.38 g, 1.93 mmol, 83%) as a white solid; $\delta_H$ (400 MHz, CDCl$_3$) 7.51 (1H, m, CH=CHC=O), 6.21 (1H, dd, -continued

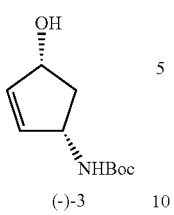

(-)-3

Vinyl acetate (7.0 cm³, 76 mmol) and PS Amano lipase (1.51 g) were successively added to a solution of the racemic alcohol (±)-3 (1.51 g, 7.59 mmol) in anhydrous dichloromethane (40 cm³) and the slurry was stirred for 72 hours at 35° C. The mixture was filtered and evaporated to dryness to give a yellow oil. Flash chromatography (SiO₂, 50% ethyl acetate in petrol) gave the optically active acetate 6 (0.76 g, 3.15 mmol, 42%) and the optically enriched alcohol (−)-3 (0.82 g, 4.12 mmol, 55% recovery). Crystallisation from petroleum ether afforded the optically active acetate 6 (0.64 g) as white orthorombic crystals, whose stereochemistry was shown by obtaining an X-ray structure.

Example 7

Preparation of (2R,4S)-(4-Hydroxycyclopent-2-enyl)-carbamic acid tert-butyl ester ((+)-3)

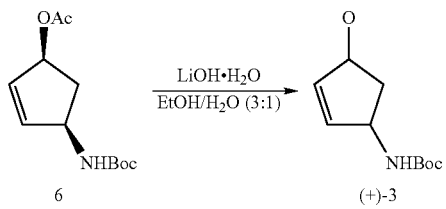

Lithium hydroxide monohydrate (0.17 g, 4.05 mmol) was added to a solution of the optically active acetate 6 (0.64 g, 2.66 mmol) in 75% aqueous ethanol (40 cm³). The solution was stirred for 4 hours at room temperature. Upon completion of reaction, the mixture was partitioned between water (40 cm³) and ethyl acetate (40 cm³), and the aqueous layer was further extracted with ethyl acetate (2×30 cm³). The combined organic layers were washed successively with sodium hydrogen carbonate (sat'd. aq., 40 cm³), water (40 cm³) and brine (40 cm³), then dried over anhydrous magnesium sulfate and evaporated to give the optically active alcohol (+)-3 (0.50 g, 2.51 mmol, 95%) as a light yellow oil, which solidified upon standing at room temperature; $[\alpha]_D$=+64.0 (c 1.0, CHCl₃); $\delta_H$ (200 MHz, CDCl₃) 5.97 (1H, m, CH=CH), 5.84 (1H, dt, J 5.8 & 1.8 Hz, CH=CH), 5.11 (1H, m), 4.66 (1H, m), 4.45 (1H, m), 2.72 (2H, dt, J 14.3 & 7.1 Hz, CH₂), 1.53 (1H, m, OH), 1.44 (9H, s, CO₂C(CH₃)₃); m/z (CI) Found [MH]⁺ 200.1285 ([MH]⁺ C₁₀H₁₈NO₃ requires 200.1287).

Example 8

Preparation of (2R)-(4-Oxocyclopent-2-enyl)-carbamic acid tert-butyl ester ((+)-4)

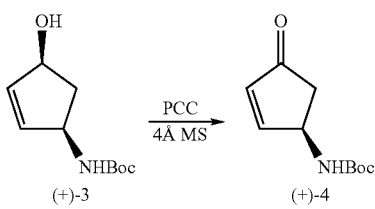

4Å powdered, activated, molecular sieves (0.5 g) and pyridinium chlorochromate (0.65 g, 3.02 mmol) were successively added to a solution of the optically active alcohol (+)-3 (0.50 g, 2.54 mmol) in anhydrous dichloromethane (20 cm³). The suspension was stirred for 1.5 hours at room temperature. Upon completion of reaction, the mixture was filtered over a short silica gel column (50% ethyl acetate in petrol) to give the optically active cyclopentenone (+)-4 (0.40 g, 2.03 mmol, 80%) as a white solid; e.e.=92% (determined by chiral GC); $[\alpha]_D$=+71.0 (c 1.0, CHCl₃); $\delta_H$ (400 MHz, CDCl₃) 7.51 (1H, m, CH=CHC=O), 6.21 (1H, dd, J 5.7 & 0.7 Hz, CH=CHC=O), 4.94 (2H, m, NH+CHNH), 2.83 (1H, m, CHH), 2.17 (1H, m, CHH), 1.45 (9H, s, CO₂C(CH₃)₃); $\delta_H$ (100 MHz, CDCl₃) 206.9 (s), 162.6 (d), 155.5 (s), 135.5 (d), 80.6 (s), 51.5 (d), 42.7 (t), 28.7 (q); m/z (EI) Found [M]⁺ 197.1057 ([M]⁺ C₁₀H₁₅NO₃ requires 197.1052).

Example 9

Preparation of (2S)-(5-iso-Butylidene-4-oxocyclopent-2-enyl)-carbamic acid tert-butyl ester ((+)-5) (CTC-199)

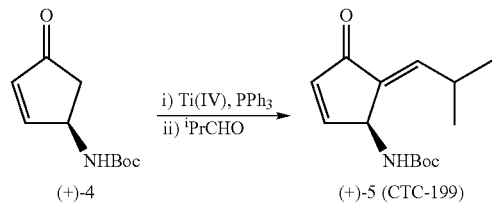

Triphenylphosphine (525 mg, 2.00 mmol) was added to a solution of the enone (+)-4 (395 mg, 2.00 mmol) in anhydrous dichloromethane (8 cm³). The solution was cooled to −50° C., then titanium (IV) isopropoxide (295 μL, 1.00 mmol) and titanium (IV) chloride (110 μL, 1.00 mmol) were successively added to the mixture. After 15 minutes stirring at −50° C., isobutyraldehyde (545 μL, 6.00 mmol) was added and the mixture was allowed to warm up to room temperature, then stirred for 17 hours at room temperature. Upon completion of reaction, the mixture was quenched with potassium carbonate (10% aq. soln., 20 cm³) and extracted with diethyl ether (5×50 cm³). The combined organic layers were dried over anhydrous magnesium sulfate, filtered and evaporated to give a red residue. Flash chromatography (SiO₂, 20% ethyl acetate in petrol) gave the starting enone (+)-4 (110 mg, 0.56 mmol, 28% recovery) as a white solid, after giving the less polar dieneone (+)-5 (220 mg, 0.88 mmol, 44% (61% based on recovery)) also as a white solid; $[\alpha]_D$=+56.0 (c 1.0, CHCl$_3$); $\delta_H$ (400 MHz, CDCl$_3$) 7.40 (1H, ddd, J 6.0, 2.5 & 0.8 Hz, CH=CHC=O), 6.48 (1H, d, J 10.7 Hz, C=CB), 6.38 (1H, dd, J 6.0 & 1.7 Hz, CH=CHC=O), 5.47 (1H, m, NH), 4.65 (1H, m, CHNH), 2.75 (1H, m, CH(CH$_3$)$_2$), 1.47 (9H, s, CO$_2$C(CH$_3$)$_3$), 1.06 (6H, m, CH(CH$_3$)$_2$); $\delta_C$ (100 MHz, CDCl$_3$) 195.7 (s), 157.4 (d), 155.3 (s), 145.7 (d), 136.6 (d), 133.3 (s), 80.7 (s), 51.9 (d), 28.9 (d), 28.7 (q), 22.4 (q), 22.3 (q); m/z (CI) Found [MH]$^+$ 252.1596 ([MH]$^+$ C$_{14}$H$_{22}$NO$_3$ requires 252.1600).

Example 10

Preparation of (2R,4S)-Acetic acid 4-tert-butoxycarbonylaminocyclopent-2-enyl ester ((−)-6)

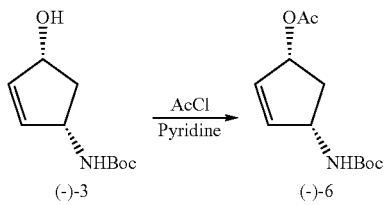

A solution of acetyl chloride (0.53 cm$^3$, 7.45 mmol) in anhydrous dichloromethane (10 cm$^3$) was added slowly to a solution of the enriched alcohol (−)-3 (1.13 g, 5.68 mmol) in a mixture of pyridine (10 cm$^3$) and anhydrous dichloromethane (10 cm$^3$), cooled to 0° C. The mixture was stirred overnight at 0° C. Upon completion of reaction, the mixture was evaporated and diluted with ethyl acetate (200 cm$^3$), then washed with citric acid (10% aq. soln., 200 cm$^3$). The aqueous layer was then extracted with ethyl acetate (150 cm$^3$). The combined organic layers were washed with brine (200 cm$^3$), dried over anhydrous magnesium sulfate, filtered and evaporated to give a yellow oil. Flash chromatography (SiO$_2$, 50% ethyl acetate in petrol) gave the optically enriched acetate (−)-6 (1.15 g, 4.77 mmol, 84%) as a yellow oil, which showed identical spectroscopic data to its enantiomer (+)-6.

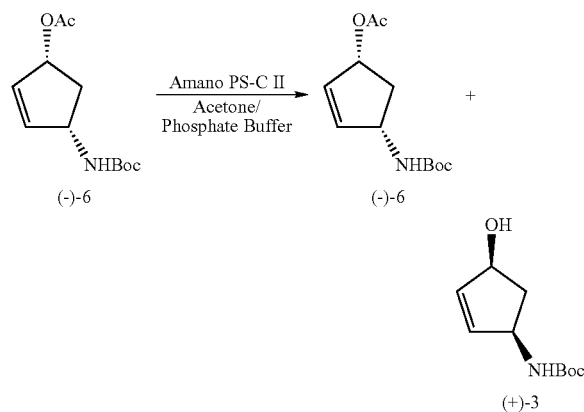

PS Amano lipase (1.15 g) was added to an emulsion of the enriched acetate (−)-6 (1.15 g, 4.77 mmol) in a mixture of acetone (20 cm$^3$) and phosphate buffer (c=0.1M, pH=7.4, 20 cm$^3$). The slurry was stirred for 54 hours at 35° C. The mixture was filtered and evaporated to dryness to give a yellow oil. Flash chromatography (SiO$_2$, 50% ethyl acetate in petrol) gave in the order of elution, the optically active acetate (−)-6 (0.84 g, 3.49 mmol, 73% recovery), and the optically enriched alcohol (+)-3 (0.19 g, 0.95 mmol, 20%).

Example 11

Preparation of (2S,4R)-(4-Hydroxycyclopent-2-enyl)-carbamic acid tert-butyl ester ((−)-3)

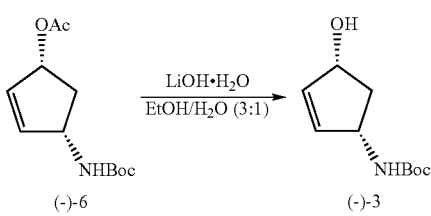

Lithium hydroxide monohydrate (0.22 g, 5.24 mmol) was added to a solution of the optically active acetate (−)-6 (0.84 g, 3.49 mmol) in 75% aqueous ethanol (48 cm$^3$). The solution was stirred overnight at room temperature. Upon completion of reaction, the mixture was partitioned between water (50 cm$^3$) and ethyl acetate (50 cm$^3$), and the aqueous layer was further extracted with ethyl acetate (2×50 cm$^3$). The combined organic layers were washed successively with sodium hydrogen carbonate (sat'd. aq., 50 cm$^3$), water (50 cm$^3$) and brine (50 cm$^3$), then dried over anhydrous magnesium sulphate and evaporated to give the optically active alcohol (−)-6 (0.70 g, 100%) as a light yellow oil, which solidified upon standing at room temperature; $[\alpha]_D$=−67.0 (c 1.0, CHCl$_3$).

Example 12

Preparation of (2S)-(4-Oxocyclopent-2-enyl)-carbamic acid tert-butyl ester ((−)-4)

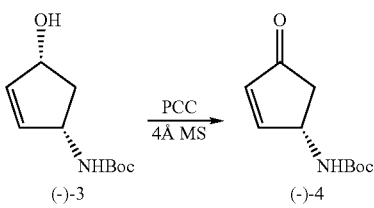

4 Å powdered, activated, molecular sieves (0.75 g) and pyridinium chlorochromate (0.91 g, 4.22 mmol) were successively added to a solution of the optically active alcohol (−)-3 (0.70 g, 3.52 mmol) in anhydrous dichloromethane (30 cm$^3$). The suspension was stirred for 1 hour at room temperature. Upon completion of reaction, the mixture was filtered over a short silica gel column (50% ethyl acetate in petrol) to give the optically active cyclopentenone (−)-4 (0.55 g, 2.79 mmol, 79%) as a white solid; e.e.=99% (determined by chiral GC); $[\alpha]_D$=−72.0 (c 1.0, CHCl$_3$).

Example 13

Preparation of (2R)-(5-iso-Butylidene-4-oxocyclopent-2-enyl)-carbamic acid tert-butyl ester ((−)-5) (CTC-195)

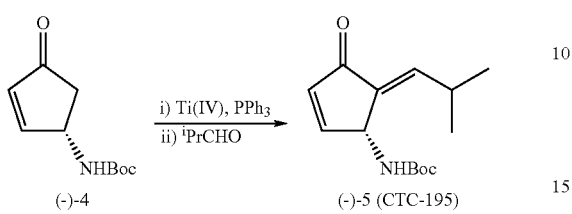

(−)-4      (−)-5 (CTC-195)

Triphenylphosphine (0.73 g, 2.78 mmol) was added to a solution of the optically active enone (−)-4 (0.55 g, 2.79 mmol) in anhydrous dichloromethane (12 cm$^3$). The solution was cooled to −50° C., then titanium (IV) isopropoxide (0.41 cm$^3$, 1.39 mmol) and titanium (IV) chloride (0.15 cm$^3$, 1.37 mmol) were successively added to the mixture. After 15 minutes stirring at −50° C., isobutyraldehyde (0.76 cm$^3$, 8.37 mmol) was added and the mixture was allowed to warm up to room temperature, then stirred for 17 hours at room temperature. Upon completion of reaction, the mixture was quenched with potassium carbonate (10% aq. soln., 20 cm$^3$) and extracted with diethyl ether (5×50 cm$^3$). The combined organic layers were dried over anhydrous magnesium sulphate, filtered and evaporated to dryness to give a red residue. Flash chromatography (SiO$_2$, 20% ethyl acetate in petrol) gave the starting enone (−)-4 (180 mg, 0.91 mmol, 33% recovery) as a white solid, after giving the less polar dieneone (−)-5 (335 mg, 1.33 mmol, 48% (71% based on recovery)) also as a white solid; $[\alpha]_D = -59.0$ (c 1.0, CHCl$_3$);

Example 14

Preparation of (2-Oxa-3-azabicyclo[2.2.1]hept-5-en-3-yl)-phenylmethanone (7)

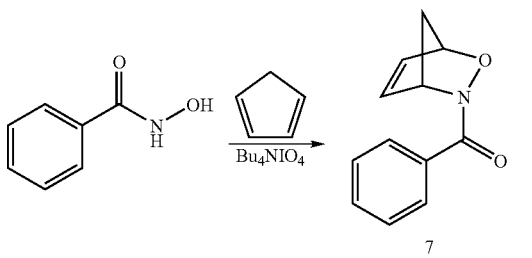

7

Tetra-n-butylammonium periodate (17.3 g, 39.9 mmol) was added to a solution of freshly cracked cyclopentadiene (4.00 g, 60.6 mmol) in dichloromethane (150 cm$^3$). Benzohydroxamic acid (5.50 g, 40.1 mmol) was then added portionwise over 5 minutes and the solution was stirred overnight at room temperature. Upon completion of reaction, the organic solution was washed successively with sodium thiosulfate (10% aq. soln., 2×400 cm$^3$) and sodium hydrogen carbonate (sat'd. aq., 500 cm$^3$), then dried over anhydrous magnesium sulfate, filtered and concentrated to give a crude black oil. Flash chromatography (SiO$_2$, 40% ethyl acetate in petrol) gave the bicyclic adduct 7 (6.23 g, 31.0 mmol, 78%) as a light brown oil, which solidified upon standing at room temperature; $\delta_H$ (250 MHz, CDCl$_3$) 7.75 (2H, m, ArH), 7.52–7.37 (3H, m, ArH), 6.50 (1H, m, CH═CH), 6.37 (1H, m, CH═CH), 5.35 (1H, m, CHNBz), 5.28 (1H, m, CHON), 2.13 (1H, dt, J 8.6 & 1.9 Hz, CHH), 1.84 (1H, m, CHH).

Example 15

Preparation of N-(4-Hydroxycyclopent-2-enyl)-benzamide (8)

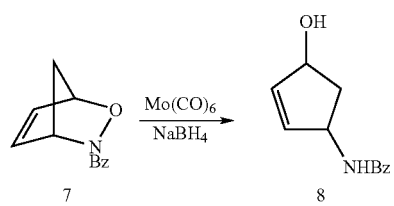

7      8

Molybdenum hexacarbonyl (12.1 g, 45.8 mmol) was added to a solution of the bicycle 7 (6.10 g, 30.3 mmol) in a 7:1 mixture of acetonitrile and water (280 cm$^3$). The suspension was stirred for 30 minutes at room temperature, then sodium borohydride (0.60 g, 15.9 mmol) was added and the suspension was heated under reflux for 4 hours. Upon completion of reaction, the mixture was allowed to cool to room temperature, filtered though a celite plug, and evaporated to dryness to give a brown solid. Flash chromatography (SiO$_2$, 80% ethyl acetate in petrol) gave the alcohol 8 (3.60 g, 17.7 mmol, 58%) as a light yellow solid; m/z (EI) Found [M]$^+$ 203.0945 ([M]$^+$ C$_{12}$H$_{13}$NO$_2$ requires 203.0946).

Example 16

Preparation of N-(4-Oxocyclopent-2-enyl)-benzamide (9) (CTC-171)

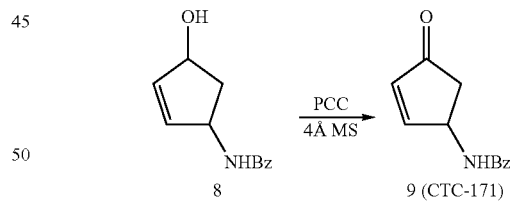

8      9 (CTC-171)

4 Å powdered, activated, molecular sieves (3.50 g) and pyridinium chlorochromate (4.20 g, 19.5 mmol) were successively added to a solution of the alcohol 8 (3.30 g, 16.3 mmol) in anhydrous dichloromethane (150 cm$^3$). The suspension was stirred for 2 hours at room temperature. Upon completion of reaction, the mixture was filtered over a short silica gel column (60% ethyl acetate in cyclohexane) to give the ketone 9 (2.60 g, 12.9 mmol, 80%) as a slightly yellow solid; $\delta_H$ (250 MHz, CDCl$_3$) 7.78 (2H, m, ArH), 7.63 (1H, dd, J 5.7 & 1.7 Hz, CH═CHC═O), 7.57–7.41 (3H, m, ArH), 6.56 (1H, m, NM), 6.29 (1H, dd, J 5.7 & 1.7 Hz, CH═CHC═O), 5.47 (1H, m, CHNH), 2.95 (1H, m, CHH), 2.28 (1H, m, CHH); m/z (EI) Found [M]$^+$ 201.0795 ([M]$^+$ C$_{12}$H$_{11}$NO$_2$ requires 201.0790).

Example 17

Preparation of N-(5-iso-Butylidene-4-oxocyclopent-2-enyl)-benzamide (10) (CTC-172)

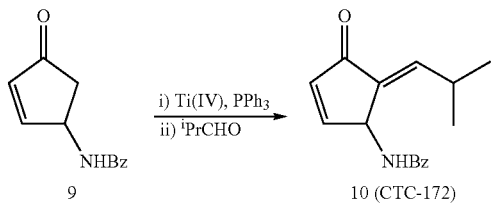

Triphenylphosphine (525 mg, 2.00 mmol) was added to a solution of the enone 9 (402 mg, 2.00 mmol) in anhydrous dichloromethane (12 cm³). The solution was cooled to −50° C., then titanium (IV) isopropoxide (0.30 cm³, 1.02 mmol) and titanium (IV) chloride (110 μL, 1.00 mmol) were successively added to the mixture. After 15 minutes stirring at −50° C., isobutyraldehyde (0.55 cm³, 6.06 mmol) was added and the mixture was allowed to warm up to room temperature, then stirred for 17 hours at room temperature. Upon completion of reaction, the mixture was quenched with potassium carbonate (10% aq. soln., 10 cm³) and extracted with diethyl ether (5×10 cm³). The combined organic layers were dried over anhydrous magnesium sulfate, filtered and evaporated to dryness to give a yellow oil. Flash chromatography (SiO$_2$, 50% ethyl acetate in petrol) gave the starting enone 9 (170 mg, 0.85 mmol, 42% recovery) as a white solid, after giving the less polar dieneone 10 (101 mg, 0.40 mmol, 20% (34% based on recovery)) also as a white solid; $\delta_H$ (400 MHz, CDCl$_3$) 7.88 (2H, m, ArH), 7.53 (1H, m, CH=CHC=O), 7.49 (3H, m, ArH), 6.81 (1H, d, J 8.9 Hz, NH), 6.48 (1H, d, J 10.8 Hz, C=CH), 6.38 (1H, dd, J 5.9 & 1.6 Hz, CH=CHC=O), 6.04 (1H, m, CHNH), 2.72 (1H, m, CH(CH$_3$)$_2$), 1.05 (6H, m, CH(CH$_3$)$_2$); $\delta_C$ (100 MHz, CDCl$_3$) 195.8 (s), 166.6 (s), 157.0 (d), 145.7 (d), 136.4 (d), 133.4 (s), 132.5 (s), 131.9 (d), 128.7 (d), 127.0 (d), 50.4 (d), 28.7 (d), 21.9 (q); m/z (EI) Found [M]$^+$ 255.1257 ([M]$^+$ C$_{16}$H$_{17}$NO$_2$ requires 255.1259).

Example 18

Preparation of 3-(4-Oxo-cyclopent-2-enyl)-4-Methylphenylsulfonyl carbamic acid (CTC-253)

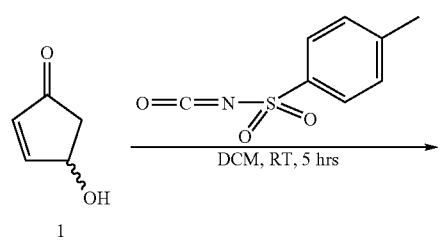

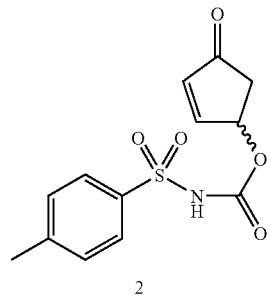

To a solution of the enone 1 (1.46 g, 14.90 mmol) in dry dichloromethane (10 cm³) was added p-tolyl sulfonyl isocyanate (2.94 g, 14.90 mmol) under nitrogen atmosphere and the reaction mixture was stirred at room temperature for 5 hours. The dichloromethane was removed in vacuo and the crude product was purified by flash chromatography over silica using ethyl acetate in hexane (2:3) as eluent to afford the title compound 2 (1.93 g, 6.54 mmol, 44%) as a light yellow solid; R$_f$ 0.25 (ethyl acetate/hexane, 1:1); $\delta_H$ (400 MHz, CDCl$_3$) 7.87–7.76 (2H, m, ArH), 7.39–7.32 (3H, m, HC=CH & ArH), 6.20 (1H, dd, J 5.6 & 1.8 Hz, HC=CH), 4.96 (1H, d, J 9.1 Hz, NH), 4.63 (1H, m, NCH), 2.58 (1H, dd, J 18.8 & 6.7 Hz, CHH), 2.45 (3H, s, CH$_3$), 1.98 (1H, dd, J 18.8 & 2.5 Hz, CHH); $\delta_C$ (100.6 MHz, CDCl$_3$) 205.3 (s), 160.9 (d), 145.7 (s), 144.3 (s), 137.2 (s), 136.0 (d), 130.1 (d), 127.2 (d), 53.6 (d), 42.1 (t), 21.6 (q).

Example 19

Preparation of 3-(4-Oxo-cyclopent-2-enyl)-cyclohexyl carbamic acid (CTC-305)

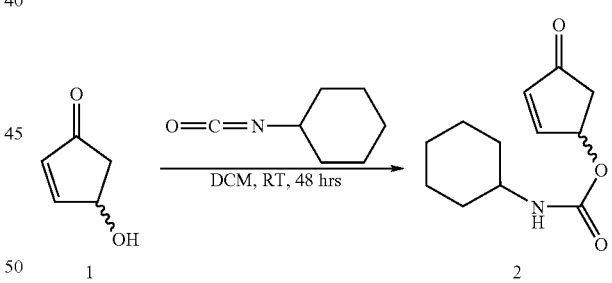

To a solution of the enone 1 (1.04 g, 0.01 mol) in dry dichloromethane (15 cm³) was added cyclohexane isocyanate (1.25 g, 0.01 mol) under nitrogen atmosphere and the reaction mixture was stirred at room temperature. After 48 hours, triethyl amine was added (1.01 g, 0.01 mol) and the reaction mixture was stirred for 24 hours more. The dichloromethane was removed in vacuo and the crude product was purified by flash chromatography over silica using ethyl acetate in hexane (2:3) as eluent to afford the title compound 2 (0.56 g, 2.51 mmol, 25%) as a solid; R$_f$ 0.7 (ethyl acetate/hexane, 3:2); $\delta_H$ (400 MHz, CDCl$_3$) 7.58 (1H, dd, J 5.5 & 2.2 Hz, HC=CH), 6.29 (1H, d, J 5.5 Hz, HC=CH), 5.80 (1H, d, J 4.6 Hz, NH), 4.65 (1H, br. s, OCH), 3.56–3.43 (1H, m, NCH), 2.81 (1H, dd, J 18.6 & 6.2 Hz, CHH), 2.36–2.28 (1H, m, CHH), 1.98–1.10 (10H, m, CH$_2$); $\delta_C$ (100.6 MHz, CDCl$_3$) 205.3 (s), 169.9 (d), 154.7 (s), 136.5 (d), 72.0 (d), 50.0 (d), 41.3 (t), 33.3 (t), 25.4 (t), 24.7 (t); m/z (CI) 241 [M+NH$_3$]$^+$, 12.3%), 224 ([M+H]$^+$, 100%), 223 (M+, 5.2%), 180 ([MH-CO$_2$]$^+$, 24.6%), Found [M+H]$^+$ 224.1286 ([M+H]$^+$ C$_{12}$H$_{18}$NO$_3$ requires 224.1287) (CTC-305).

Example 20

Preparation of 3-(4-Oxo-cyclopent-2-enyl)-carbamic acid phenyl ester (CTC-269)

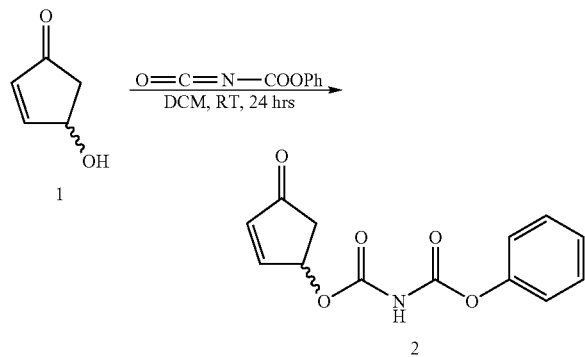

To a solution of the enone 1 (1.18 g, 12.00 mmol) in dry dichloromethane (15 cm$^3$) was added phenyl isocyanatoformate (2.00 g, 12.00 mmol) under nitrogen atmosphere and the reaction mixture was stirred at room temperature for 24 hours. The dichloromethane was removed in vacuo and the crude product was purified by flash chromatography over silica using ethyl acetate in hexane (1:4) as eluent to afford the title compound 2 (0.85 g, 3.26 mmol, 27%) as a white solid; R$_f$ 0.4 (ethyl acetate/hexane, 1:1); $\delta_H$ (400 MHz, CDCl$_3$) 7.60 (1H, dd, J 5.7 & 2.4 Hz, HC=CH), 7.38 (2H, t, J 7.9 Hz, ArH), 7.23 (1H, t, J 7.5 Hz, ArH), 7.14 (2H, m, ArH), 6.30 (1H, dd, J 5.7 & 1.7 Hz, HC=CH), 5.33 (1H, m, NH), 5.07 (1H, m, NCH), 2.93 (1H, dd, J 18.8 & 6.8 Hz, CHH), 2.28 (1H, dd, J 18.8 & 2.5 Hz, CHH); $\delta_C$ (100.6 MHz, CDCl$_3$) 205.8 (s), 161.2 (d), 154.0 (s), 150.7 (s), 135.8 (d), 129.4 (d), 125.7 (d), 121.4 (d), 120.5 (s), 51.6 (d), 42.0 (t).

Example 21

Preparation of 4-Phenylamino-cyclopent-2-one (CTC-252)

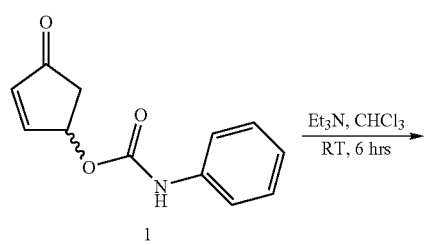

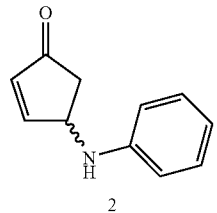

To a solution of the enone 1 (0.53 g, 2.44 mmol) in dry chloroform (20 cm$^3$) was added triethyl amine (0.31 g, 3.05 mmol) under nitrogen atmosphere and the reaction mixture was stirred at room temperature for 4 hours. The chloroform was removed in vacuo and the crude product was purified by flash chromatography over silica using ethyl acetate in hexane (1:6) as eluent to afford the title compound 2 (0.40 g, 2.31 mmol, 95%) as a yellow crystalline solid; R$_f$ 0.5 (ethyl acetate/hexane, 2:3); $\delta_H$ (400 MHz, CDCl$_3$) 7.67 (1H, dd, J 5.7 & 2.4 Hz, HC=CH), 7.26–7.19 (2H, m, ArH), 6.84–6.78 (1H, m, ArH), 6.71–6.65 (2H, m, ArH), 6.31 (1H, dd, J 5.7 & 1.8 Hz, HC=CH), 4.78 (1H, br. s, NH), 3.75 (1H, br. s, NCH), 2.91 (1H, dd, J 18.6 & 6.2 Hz, CHH), 2.23 (1H, dd, J 18.6 & 2.4 Hz, CHH); $\delta_C$ (100.6 MHz, CDCl$_3$) 206.7 (s), 162.2 (d), 146.4 (s), 135.5 (d), 129.6 (d), 118.8 (d), 113.6 (d), 54.0 (d), 43.0 (t); m/z (CI) 174 [M+H]$^+$, 100%), 173 (M+, 19%), Found [M+H]$^+$ 174.0925 ([M+H]$^{30}$ C$_{11}$H$_{12}$NO requires 174.0919).

Example 22

Preparation of 2-Chloro-N-(4-oxo-cyclopent-2-enyl)-acetamide (CTC-304)

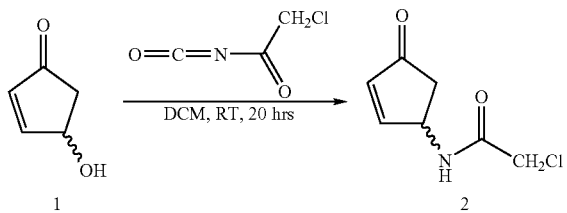

To a solution of the enone 1 (0.96 g, 9.80 mmol) in dry dichloromethane (10 cm$^3$) was added chloroacetyl isocyanate (1.17 g, 9.80 mmol) under nitrogen atmosphere and the reaction mixture was stirred at room temperature for 20 hours. The dichloromethane was removed in vacuo and the crude product was purified by flash chromatography over silica using ethyl acetate in hexane (1:4) as eluent to afford the title compound 2 (0.68 g, 3.18 mmol, 41%) as a white solid; R$_f$ 0.5 (ethyl acetate); $\delta_H$ (400 MHz, CDCl$_3$) 7.53 (1H, dd, J 5.6 & 2.4 Hz, HC=CH), 6.71 (1H, s, NH, 6.33 (1H, dd, J 5.6 & 1.8 Hz, HC=CH), 5.31–5.23 (1H, m, NCH), 4.09 (2H, s, ClCH$_2$), 2.91 (1H, dd, J 18.8 & 6.8 Hz, CHH), 2.22 (1H, dd, J 18.8 & 2.7 Hz, CHH); $\delta_C$ (100.6 MHz, CDCl$_3$) 205.5 (s), 165.8 (s), 160.6 (d), 136.2 (d), 50.0 (d), 42.4 (t), 41.7 (t); m/z (CI) 191 [M+NH$_3$]$^+$, 100%), 174 ([M+H]$^+$, 39.2%), 173 (M$^+$, 3.7%), 157 ([M+NH$_3$—Cl]$^+$, 52.5%), 140 ([M+H—Cl]$^+$, 69.7%), Found [M+H]$^+$ 174.0321 ([M+H]$^+$ C$_7$H$_9$NO$_2$Cl requires 174.0322) (CTC-304).

Example 23

Preparation of
N-(4-Oxocyclopent-2-enyl)-benzenesulfonamide
(CTC-299)

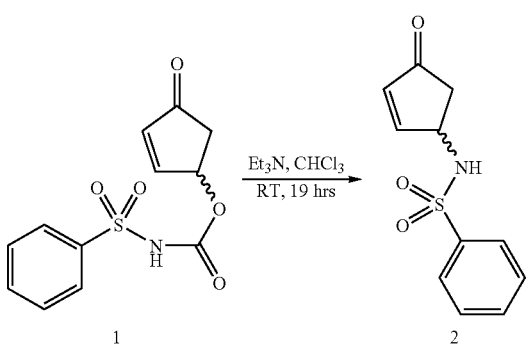

To a solution of the enone 1 (0.60 g, 2.10 mmol) in dry chloroform (10 cm³) was added triethyl amine (0.23 g, 2.30 mmol) and the reaction mixture was stirred at room temperature for 19 hours under nitrogen atmosphere. The chloroform was removed in vacuo and the crude product was purified by flash chromatography over silica using ethyl acetate in hexane (2:3) as eluent to afford the title compound 2 (0.22 g, 0.93 mmol, 43%) as a white crystalline solid; $R_f$ 0.4 (ethyl acetate/hexane, 3:2); $\delta_H$ (400 MHz, CDCl$_3$) 7.91–7.87 (2H, m, ArH, 7.65–7.60 (1H, m, ArH), 7.57–7.51 (2H, m, ArH), 7.35 (1H, dd, J 5.7 & 2.5 Hz, HC=CH), 6.17 (1H, dd, J 5.7 & 1.8 Hz, HC=CH), 5.64 (1H, d, J 8.9 Hz, NH), 4.63–4.57 (1H, m, NCH), 2.55 (1H, dd, J 18.8 & 6.8 Hz, CHH), 2.02 (1H, dd, J 18.8 & 2.7 Hz, CHH); $\delta_C$ (100.6 MHz, CDCl$_3$) 205.6 (s), 161.0 (d), 140.2 (s), 135.7 (d), 133.1 (d), 129.4 (d), 127.0 (d), 53.5 (d), 41.8 (t); m/z (CI) 255 ([M+NH$_3$]$^+$, 100%), 238 ([M+H]$^+$, 17%), 237 (M$^+$, 2.5%), 96 ([M-SO$_2$Ph]$^+$, 70.5%), Found [M+H]$^+$ 238.0534 ([M+H]$^+$ C$_{11}$H$_{12}$NO$_3$S requires 238.0538).

Example 24

Preparation of (4-Oxocyclopent-2-enyl)-carbamic acid phenyl ester (CTC-260)

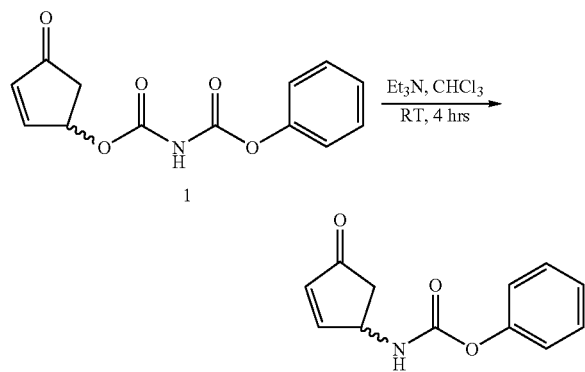

To a solution of the enone 1 (0.41 g, 1.57 mmol) in dry chloroform (10 cm³) was added triethyl amine (0.16 mg, 1.65 mmol) and the reaction mixture was stirred at room temperature for 4 hours under nitrogen atmosphere. The solvent was removed in vacuo to afford the title compound 2 (0.40 g, 1.84 mmol, 96%) as a copper coloured solid; $R_f$ 0.4 (ethyl acetate/hexane, 1:1); $\delta_H$ (400 MHz, CDCl$_3$) 7.58 (1H, dd, J 5.6 & 2.4 Hz, HC=CH), 7.40–7.33 (2H, m, ArH), 7.24–7.19 (1H, m, ArH), 7.15–7.10 (2H, m, ArH), 6.29 (1H, dd, J 5.6 & 1.8 Hz, HC=CH), 5.28 (1H, br.s, NH), 5.09–5.01 (1H, m, NCH), 2.91 (1H, dd, J 18.6 & 6.8 Hz, CHH), 2.27 (1H, dd, J 18.6 & 2.2 Hz, CHH); $\delta_C$ (100.6 MHz, CDCl$_3$) 205.7 (s), 161.1 (d), 153.9 (s), 150.7 (s), 135.8 (d), 129.4 (d), 125.7 (d), 121.4 (d), 51.6 (d), 42.0 (t)□ m/z ((CI)) 235 [M+NH$_3$]$^+$, 100%), 218 ([M+H]$^+$, 15.8%), 217 (M+, 0.3%), Found [M+H]$^+$ 218.0824 ([M+H]$^+$ C$_{12}$H$_{12}$NO$_3$ requires 218.0817).

Example 25

Preparation of (4-Oxocyclopent-2-enyl)-carbamic acid ethyl ester (CTC-271)

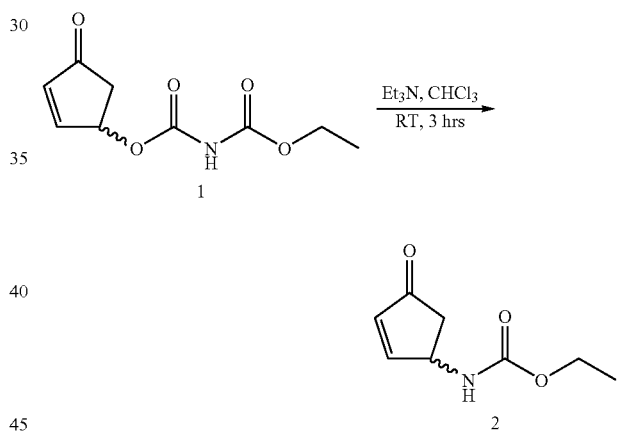

To a solution of the enone 1 (1.15 g, 5.40 mmol) in dry chloroform (20 cm³) was added triethyl amine (0.60 g, 5.90 mmol) under nitrogen atmosphere and the reaction mixture was stirred at room temperature for 3 hours. The chloroform was removed in vacuo and the crude product was purified by flash chromatography over silica using ethyl acetate in hexane (1:1) as eluent to afford the title compound 2 (0.95 g, 5.62 mmol, 85%) as a white crystalline solid; $R_f$ 0.3 (ethyl acetate/hexane, 1:1); $\delta_H$ (400 MHz, CDCl$_3$) 7.53 (1H, m, HC=CH$_3$, 6.25 (1H, m, HC=CH), 5.00 (1H, br. s, NH), 4.91 (1H, br. s, NCH), 4.15 (2H, q, J 7.1 Hz, CH$_3$CH$_2$), 2.86 (1H, dd, J 18.7 & 6.5 Hz, CHH), 2.18 (1H, dd, J 18.7 & 2.4 Hz, CHH), 1.26 (3H, t, J 7.1 Hz, CH$_2$CH$_3$); $\delta_C$ (100.6 MHz, CDCl$_3$) 206.2 (s), 161.7 (d), 155.9 (s), 135.4 (d), 61.4 (t), 51.4 (d), 42.3 (t), 14.5 (q); m/z (CI) 187 ([M+NH$_3$]$^+$, 100%), 170 ([M+H]$^+$, 91.6%), 169 (M+, 14%), Found [M+H]$^+$ 170.0814 ([M+H]$^+$ C$_8$H$_{12}$NO$_3$ requires 170.0817).

Example 26

Preparation of N-tert-Butoxycarbonyl-(4-Oxocyclopent-2-enyl)-carbamic acid ethyl ester (CTC-267)

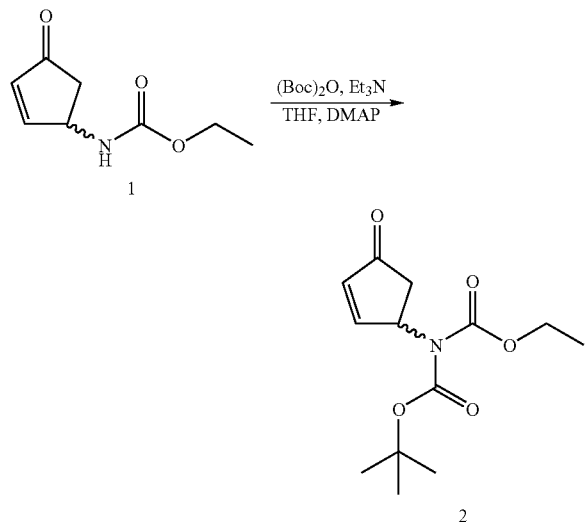

To a solution of the enone 1 (0.08 g, 0.46 mmol) and di-tert-butyl dicarbonate (0.12 g, 0.55 mmol) in dry THF (10 cm³) was added triethyl amine (0.52 g, 5.10 mmol) and a catalytic amount of 4-(dimethylamino) pyridine, the reaction mixture was stirred at room temperature for 20 hours under nitrogen atmosphere. The THF was removed in vacuo and the crude product was purified by flash chromatography over silica using ethyl acetate in hexane (1:1) as eluent to afford the title compound 2 (0.02 g, 0.07 mmol, 32%) as an oil; $R_f$ 0.6 (ethyl acetate/hexane, 1:1); $\delta_H$ (400 MHz, CDCl₃) δ 7.50 (1H, dd, J 5.7 & 2.4 Hz, HC=CH), 6.22 (1H, dd, J 5.7 & 2.4 Hz, HC=CH), 5.59 (1H, m, NCH), 4.25 (2H, q, J 7.2 Hz, CH₂CH₃), 2.73 (1H, dd, J 18.2 & 7.0 Hz, CHH), 2.55 (1H, dd, J 18.2 & 3.2 Hz, CHH), 1.48 (9H, s, C(CH₃)₃), 1.31 (3H, t, J 7.2 Hz, CH₂CH₃); $\delta_C$ (100.6 MHz, CDCl₃) 205.8 (s), 162.2 (d), 153.8 (s), 151.6 (s), 134.1 (d), 84.0 (s), 63.4 (t), 56.2 (d), 40.3 (t), 27.9 (q), 14.1(q); m/z (CI) 287 ([M+NH₃]⁺, 2.2%), 270 ([M+H]⁺, 1.8%), 187 ([1+NH₃]³⁰, 68.2%), 170 ([1+H]⁺, 100%), 169 (1⁺, 14%), Found [M+H]⁺ 270.1339 ([M+H]⁺C₁₃H₂₀NO₅ requires 270.1341).

Example 27

Preparation of {5-[1-(4-Fluorophenyl)-meth-(E)-ylidene]-4-oxocyclopent-2-enyl}-carbamic acid phenyl ester (CTC-261)

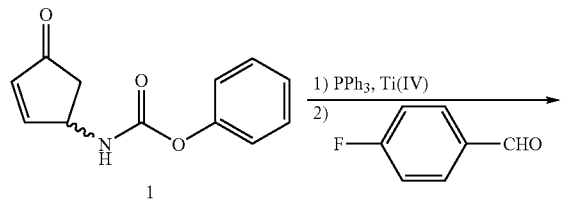

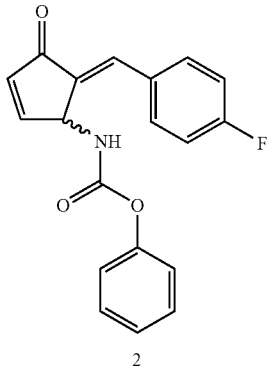

To a solution of the enone 1 (0.12 g, 0.56 mmol) and triphenyl phosphine (0.15 g, 0.56 mmol) in dry dichloromethane (20 cm³) was added titanium (IV) chloride (0.05 g, 0.28 mmol) and titanium (IV) isopropoxide (0.08 g, 0.28 mmol) at −50° C. under nitrogen atmosphere. After 15 minutes, the reaction mixture was treated with 4-fluorobenzaldehyde (0.21 g, 1.68 mM) and maintained at −50° C. for 3 hours then warmed to room temperature overnight. Potassium carbonate (10% aq. soln, 1.5 cm³) was added to the reaction mixture and then stirred for 15 minutes. The organic layer was extracted with dichloromethane (200 cm³), washed with citric acid (10%) (2×10 cm³), water (2×15 cm³), brine (2×15 cm³) and dried over magnesium sulfate. The solvent was removed in vacuo and the crude product was purified by flash chromatography over silica using ethyl acetate in hexane (1:4) as eluent to afford the title compound 2 (0.03 g, 0.09 mmol, 19%) as a white solid; $R_f$ 0.5 (ethyl acetate/hexane, 1:1); $\delta_H$ (400 MHz, CDCl₃) 7.67–7.58 (3H, m, ArH & HC=CH), 7.51 (1H, s, ArH), 7.38 (2H, t, J 7.9 Hz, ArH), 7.25–7.21 (1H, m, ArH), 7.18–7.12 (2H, m, ArH), 7.05–7.00 (2H, d, j 7.9 Hz, ArH), 6.58 (1H, dd, J 4.3 & 1.6 Hz, HC=CH), 5.89 (1H, dd, J 8.7 & 1.6 Hz, NH), 4.88 (1H, d, J 8.7 Hz, NCH); $\delta_C$ (100.6 MHz, CDCl₃) 194.6 (s), 164.9 (s), 162.4 (s), 156.4 (d), 154.2 (s), 150.5 (s), 136.0 (d), 133.3 (d), 133.1 (dd, J 8.5 Hz), 131.3 (s), 129.1 (d), 125.6 (d), 121.2 (d), 116.0 (dd, J 21.7 Hz), 52.4 (d); m/z (CI) 341 [M+NH₃]⁺, 25.8%), 324 [M+H]⁺, 14.2%), 247 ([M-OPh+NH₃]⁺, 38.6%), 230 [M-OPh]⁺, 100%), Found [M+H]⁺ 324.1024 ([M+H]⁺ C₁₉H₁₅FNO₃ requires 324.1036).

Example 28

Preparation of {4-Oxo-5-[1-phenyl-meth(E)-ylidene]-cyclopent-2-enyl}-carbamic acid phenyl ester (CTC-259)

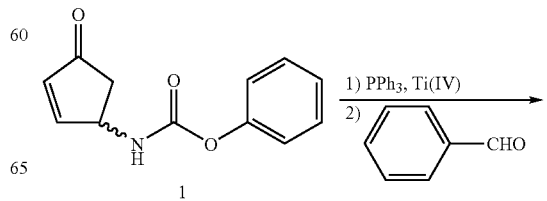

-continued

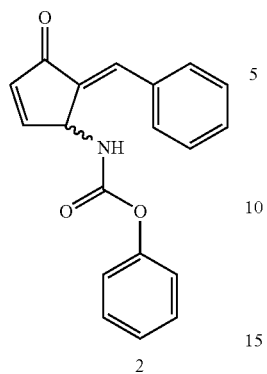

To a solution of the enone 1 (0.12 g, 0.56 mmol) and triphenyl phosphine (0.15 g, 0.56 mmol) in dry dichloromethane (20 cm³) was added titanium (IV) chloride (0.05 g, 0.28 mmol) and titanium (IV) isopropoxide (0.08 g, 0.28 mmol) at −50° C. under nitrogen atmosphere. After 15 minutes, the reaction mixture was treated with benzaldehyde (0.18 g, 1.68 mmol) and maintained at −50° C. for 3 hours then warmed to room temperature overnight. Potassium carbonate (10% aq. soln, 1.5 cm³) was added to the reaction mixture and then stirred for 15 minutes. The organic layer was extracted with dichloromethane (200 cm³), washed with citric acid (10%) (2×10, cm³), water (2×15 cm³), brine (2×15 cm³) and dried over sodium sulfate. The solvent was removed in vacuo and the crude product was purified by flash chromatography over silica using ethyl acetate in hexane (1:4) as eluent to afford the title compound 2 (0.03 g, 0.10 mmol, 21%) as a white crystalline solid; $R_f$ 0.4 (ethyl acetate/hexane, 1:1); $\delta_H$ (400 MHz, CDCl$_3$) 7.67 (1H, dd, J 5.8 & 1.9 Hz, HC=CH), 7.64–7.59 (2H, m, ArH), 7.56 (1H, s, ArH), 7.48–7.44 (2H, m, ArH), 7.36 (2H, t, J 7.8 Hz, ArH), 7.22 (1H, t, J 7.5 Hz, ArH), 7.02 (2H, d, J 7.8 Hz, ArH), 6.58 (1H, dd, J 5.8 & 1.4 Hz, HC=CH), 5.94–5.89 (1H, m, NH), 4.90 (1H, d, J 8.3 Hz, NCH); $\delta_C$ (100.6 MHz, CDCl$_3$) 195.0 (s), 156.8 (d), 154.4 (s), 150.8 (s), 136.2 (d), 134.8 (d), 133.1 (s), 131.8 (s), 131.2 (d), 130.5 (d), 129.4 (d), 128.9 (d), 125.7 (d), 121.5 (d), 52.8 (d); m/z (CI) 323 ([M+NH$_3$]$^+$, 4.4%), 306 ([M+H]$^+$, 6.7%), 229 ([M-OPh+NH$_3$]$^+$, 19.8%), 212 ([M-OPh]$^+$, 100%), Found [M+H]$^+$ 306.1138 ([M+H]$^+$ C$_{19}$H$_{16}$NO$_3$ requires 306.1130).

Example 29

Preparation of {5-[1-(4-Fluorophenyl)-meth-(E)-ylidene]-4-oxocyclopent-2-enyl}-carbamic acid ethyl ester (CTC-276)

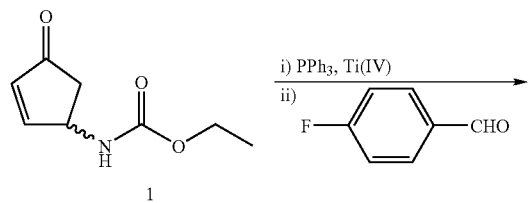

-continued

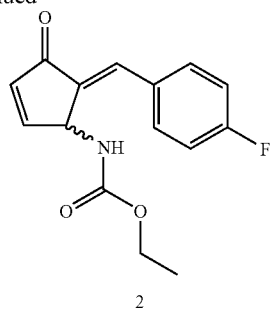

To a solution of the enone 1 (0.20 g, 1.18 mmol) and triphenyl phosphine (0.32 g, 1.22 mmol) in dry dichloromethane (20 cm³) was added titanium (IV) chloride (0.11 g, 0.59 mmol) and titanium (IV) isopropoxide (0.17 g, 0.59 mmol) at −50° C. under nitrogen atmosphere. After 15 minutes, the reaction mixture was treated with 4-fluorobenzaldehyde (0.44 g, 3.55 mmol) and maintained at −50° C. for 3 hours then warmed to room temperature overnight. Potassium carbonate (10% aq. soln, 2 cm³) was added to the reaction mixture and then stirred for 30 minutes. The organic layer was extracted with dichloromethane (100 cm³), washed with citric acid (10%) (2×10 cm³), water (2×10 cm³), brine (2×10 cm³) and dried over magnesium sulfate. The solvent was removed in vacuo and the crude product was purified by flash chromatography over silica using ethyl acetate in hexane (1:4) as eluent to afford the title compound 2 (0.06 g, 0.22 mmol, 18%) as a white crystalline solid; $R_f$ 0.7 (ethyl acetate/hexane, 3:2); $\delta_H$ (400 MHz, CDCl$_3$) 7.61–7.54 (3H, m, HC=CH & ArH), 7.45 (1H, br. s, C=CH), 7.14–7.07 (2H, m, ArH), 6.51 (1H, dd, J 5.9 & 1.6 Hz, HC=CH), 5.80 (1H, d, J 7.8 Hz, NH), 4.55 (1H, d, J 7.8 Hz, NCH), 4.22–4.11 (2H, m, CH$_2$CH$_3$), 1.24–1.19 (3H, t, J 6.8 Hz, CH$_2$CHH); $\delta_C$ (100.6 MHz, CDCl$_3$) 195.1 (s), 165.0 (s), 162.5 (s), 157.2 (d), 150.9 (s), 135.7 (d), 133.4 (dd, J 8.8 Hz), 133.2 (d), 129.3 (sd, J 3.2 Hz), 116.0 (dd, J 22.4 Hz), 61.6 (t), 52.4 (d), 14.6 (q); m/z (CI) 293 ([M+NH$_3$]$^+$, 24%), 276 ([M+H]$^+$, 100%), 275 (M+, 26%), Found [M+H]$^+$ 276.1044 ([M+H]$^+$ C$_{15}$H$_{15}$FNO$_3$ requires 276.1036).

Example 30

Preparation of {4-Oxo-5-[1-phenyl-meth-(E)-ylidene]-cyclopent-2-enyl}-carbamic acid ethyl ester (CTC-270)

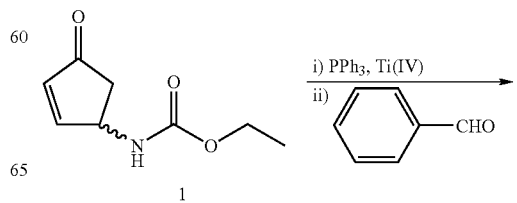

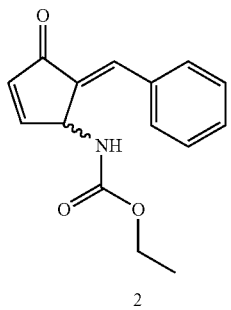

To a solution of the enone 1 (0.13 g, 0.80 mmol) and triphenyl phosphine (0.21 g, 0.81 mmol) in dry dichloromethane (20 cm³) was added titanium (IV) chloride (0.07 g, 0.40 mmol) and titanium (IV) isopropoxide (0.11 g, 0.40 mmol) at −50° C. under nitrogen atmosphere. After 15 minutes, the reaction mixture was treated with benzaldehyde (0.26 g, 2.40 mmol) and maintained at −50° C. for 3 hours then warmed to room temperature overnight. Potassium carbonate (10% aq. soln, 2 cm³) was added to the reaction mixture and then stirred for 15 minutes. The organic layer was extracted with dichloromethane (100 cm³), washed with citric acid (10%) (2×10 cm³), water (2×10 cm³), brine (2×10 cm³) and dried over magnesium sulfate. The solvent was removed in vacuo and the crude product was purified by flash chromatography over silica using ethyl acetate in hexane (1:4) as eluent to afford the title compound 2 (0.06 mg, 0.25 mmol, 32%) as a white crystalline solid; $R_f$ 0.4 (ethyl acetate/hexane, 2:3); $\delta_H$ (400 MHz, CDCl₃) 7.55–7.46 (3H, m, HC=CH & ArH), 7.45 (1H, br.s, C=CH, 7.35–7.30 (3H, m, ArH), 6.49 (1H, dd, J 5.9 & 1.6 Hz, HC=CH), 5.75 (1H, d, J 7.8 Hz, NH), 4.46 (1H, d, J 7.8 Hz, NCH), 4.11–4.00 (2H, m, CH₂CH₃), 1.15–1.08 (3H, t, J 6.5 Hz, CH₂CH₃); $\delta_C$ (100.6 MHz, CDCl₃) 195.1 (s), 161.7 (s), 157.4 (d), 135.6 (d), 134.5 (d), 133.0 (s), 132.1 (s), 131.3 (d), 130.2 (d), 128.8 (d), 61.5 (t), 52.6 (d), 14.6 (q); m/z (CI) 275 ([M+NH₃]⁺, 43.5%), 258 ([M+H]⁺, 100%), 257 (M+, 28.7%), Found [M+H]⁺ 258.1138 ([M+H]⁺ C₁₅H₁₆NO₃ requires 258.1130).

Example 31

Preparation of [(1R,2R)-2-(Naphthalen-2-ylsulfanyl)-4-oxocyclopentyl]-carbamic acid methyl ester; compound with benzene (CTM-238) & [(1R,2S)-2-(Naphthalen-2-ylsulfanyl)-4-oxocyclopentyl]-carbamic acid methyl ester; compound with benzene (CTM-237)

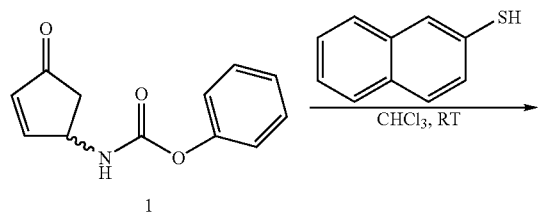

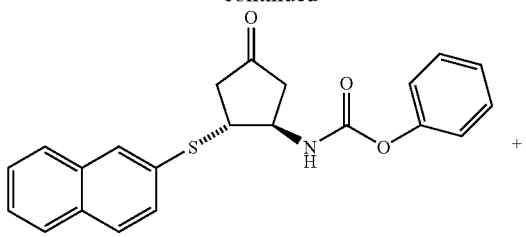

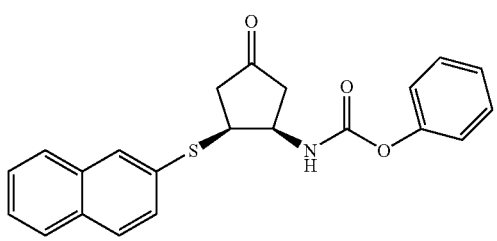

To a solution of the the enone 1 (89 mg, 0.41 mmol) and 2-Naphtalene thiol (73 mg, 0.45 mmol) in dry chloroform (5 cm³) was added a catalytic amount of triethyl amine at room temperature under nitrogen atmosphere and the reaction mixture was stirred for 1 hour. The chloroform was removed in vacuo and the crude product was purified by flash chromatography over silica using ethyl acetate in hexane (1:6) as eluent to afford the esters 2 (71 mg, 0.18 mmol) and 3 (12 mg, 0.03 mmol) with a ratio of 6:1 (53%) as white solids; $R_f$ 0.8 (2) & 0.7 (3) (ethyl acetate/hexane, 1:1); (2) $\delta_H$ (400 MHz, CDCl₃) 8.04 (1H, s, ArH), 7.86–7.77 (3H, m, ArH), 7.59–7.55 dd, J 8.4 & 1.6 Hz, ArH), 7.54–7.48 (2H, m, ArH), 7.39–7.32 (2H, m, ArH), 7.24–7.19 (1H, m, ArH), 7.08–7.03 (2H, d, J 8.0 Hz, ArH), 5.36–5.22 (1H, br. s, NH), 4.32–4.21 (1H, m, NCH), 4.04–3.92 (1H, in, SCH), 3.03–2.93 (1H, dd, J 18.6 & 7.3 Hz, CHH), 2.92–2.83 (1H, dd, J 18.6 & 7.8 Hz, CHH), 2.43–2.30 (2H, m, CH₂); $\delta_C$ (100.6 MHz, CDCl₃) 211.5 (s), 153.9 (s), 150.6 (s), 133.7 (s), 132.7 (s), 132.2 (d), 129.9 (d), 129.6 (s), 129.4 (d), 129.0 (d), 127.7 (d), 127.6 (d), 126.8 (d), 126.7 (d), 125.6 (d), 121.4 (d), 54.4 (d), 48.1 (d), 43.9 (t), 43.7 (t); m/z (ES+) Found [M+Na]⁺ 400.0994 ([M+Na]⁺ C₂₂H₁NO₃SNa requires 400.0983); Expt. No. MC1/51/A; (3) $\delta_H$ (400 MHz, CDCl₃) 7.96 (1H, s, ArH), 7.84–7.75 (3H, m, ArH), 7.54–7.48 (3H, m, ArH), 7.31–7.26 (2H, m, ArH), 7.19–7.12 (1H, m, ArH), 6.94–6.89 (2H, dc, J 8.0 Hz, ArH), 5.70–5.61 (1H, s, NH), 4.64–4.56 (1H, m, NCH), 4.39–4.31 (1H, m, SCH), 2.79–2.71 (1H, dd, J 18.9 & 7.5 Hz, CHH), 2.69–2.63 (2H, dd, J 7.8 & 2.7 Hz, CH2.61–2.53 (1H, dd, J 18.9 & 4.6 Hz, CHH); $\delta_C$ (100.6 MHz, CDCl₃) 211.3 (s), 154.1 (s), 150.7 (s), 133.8 (s), 132.7 (s), 130.9 (s), 129.4 (d), 129.3 (d), 129.2 (d), 128.9 (d), 127.8 (d), 127.5 (d), 127.0 (d), 126.7 (d), 125.5 (d), 121.4 (d), 51.7 (d), 48.5 (d), 44.6 (t), 42.7 (t); m/z (ES+) Found [M+Na]⁺ 400.0972 ([M+Na]⁺ C₂₂H₁₉NO₃SNa requires 400.0983); Expt. No. MC1/51/C.

Example 32

Preparation of (R)-2-tert-Butoxycarbonylamino-3-((1R,2R)-4-oxo-2-phenoxy-carbonyl-amino-cyclopentyl-sulfanyl)-propionic acid methyl ester (CTM-236)

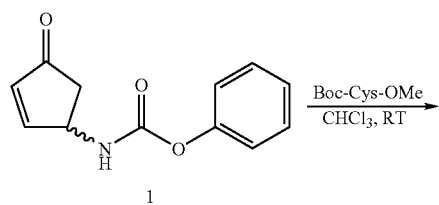

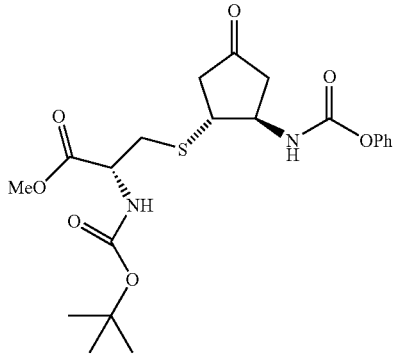

To a solution of the enone 1 (86 mg, 0.40 mmol) and Boc-Cys-OMe (0.14 g, 0.60 mmol) in dry chloroform (5 cm$^3$) was added a catalytic amount of triethyl amine at room temperature under nitrogen atmosphere and the reaction mixture was stirred for 4 hours. The chloroform was removed in vacuo and the crude product was purified by flash chromatography over silica using ethyl acetate in hexane (2:3) as eluent to afford the ester 2 (0.12 g, 0.27 mmol, 67%) as a white solid; R$_f$ 0.4 (ethyl acetate/hexane, 1:1); $\delta_H$ (400 MHz, CDCl$_3$) 7.39–7.33 (2H, m, ArH), 7.24–7.18 (1H, m, ArH), 7.17–7.12 (2H, m, ArH), 6.05 (1H, br.s, NM), 5.77 (1H, br.s, NH), 5.44–5.32 (1H, m, CH$_3$OCOCH), 4.66–4.56 (1H, m, NCH), 4.55–4.45 (1H, m, SCH), 3.78 (3H, s, OCH$_3$), 3.19–3.08 (1H, m, CHH), 3.05–2.96 (1H, m, CHH), 2.71–2.56 (3H, m, CHH & SCH$_2$), 2.47–2.35 (1H, m, CHH), 1.47–1.44 (9H, d, J 2.2 Hz, OC(CH$_3$)$_3$); $\delta_C$ (100.6 MHz, CDCl$_3$) 211.6 (s), 171.0 (s), 154.3 (s), 150.8 (s), 150.7(s), 129.3 (d), 125.6 (d), 121.5 (d), 80.6 (s), 52.8 (q) 51.4 (d), 51.0 (d), 45.9 (d), 44.8 (t), 44.1 (t), 34.1(t), 28.3 (q); m/z (ES+) Found [M+Na]$^+$ 475.1526 ([M+Na]$^+$ C$_{21}$H$_{28}$N$_2$O$_7$SNa requires 475.1515); Expt. No. MC1/52/B.

Example 33

General Scheme:

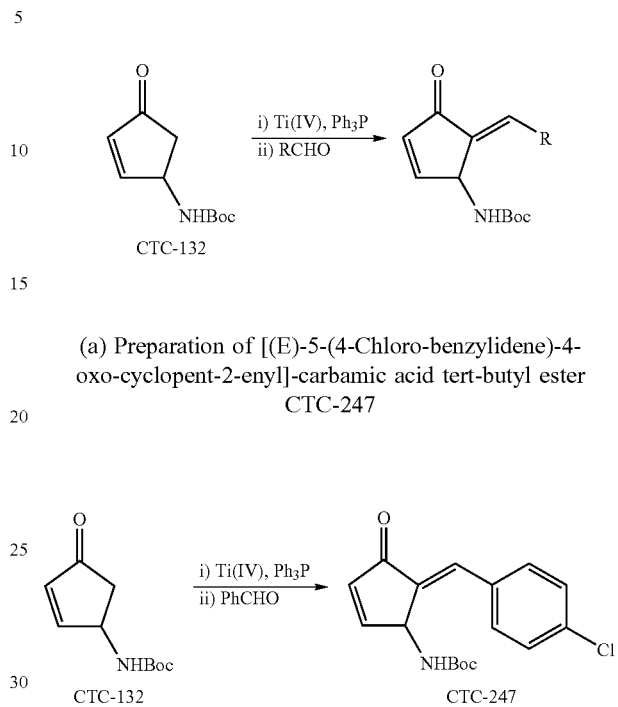

(a) Preparation of [(E)-5-(4-Chloro-benzylidene)-4-oxo-cyclopent-2-enyl]-carbamic acid tert-butyl ester CTC-247

Triphenyl phosphine (333 mg, 1.27 mmol) was added to a stirred solution of the enone CTC-132 (250 mg, 1.27 mmol) in dichloromethane (6 ml) at room temperature, under an atmosphere of argon. The resulting mixture was then cooled to −50° C. and titanium (IV) isopropoxide (0.19 ml, 0.64 mmol) and then titanium (IV) chloride (70 µl, 0.64 mmol) were added dropwise over 3 minutes each. The mixture was stirred at −50° C. for a further 15 minutes, then a solution of 4-chlorobenzaldehyde (535 mg, 3.81 mmol) in dichloromethane (1 ml) was added over 3 minutes. The reaction mixture was then allowed to warm to room temperature over 18 hours. An aqueous solution of potassium carbonate (10% aq., 6 ml) was then added, the biphasic mixture was stirred for 90 minutes and the mixture was extracted with diethyl ether (5×6 ml). The combined organic extracts were then dried over MgSO$_4$, and evaporated in vacuo. Flash chromatography (SiO$_2$, 20%, then 35% ethyl acetate in hexane) gave the starting enone CTC-132 (93 mg, 0.47 mmol, 37% recovery) as a white solid, after giving the less polar dieneone CTC-247 (210 mg, 0.66 mmol, 52% (82% based on recovery) also as a white solid; $\delta_H$ (400 MHz, CDCl$_3$) 7.58 (1H, ddd J 5.9, 2.4 & 0.7 Hz, CH=CHC=O), 7.51 (2H, dt J 8.6 & 1.9 Hz, ArH), 7.43 (1H, br. s, C=CHAr), 7.38 (2H, dt J 8.6 & 1.9 Hz, ArH), 6.51 (1H, dd J 5.9 & 1.7 Hz, CH=CHC=O), 5.79 (1H, br. d J 8.0 Hz, NH), 4.41 (1H, br. d J 8.0 Hz, CHNH), 1.45 (9H, s, CO$_2$C(CH$_3$)$_3$); $\delta_C$ (100 MHz, CDCl$_3$) 195.2 (s), 157.7 (d), 155.3 (s), 136.3 (s), 135.6 (s), 135.5 (d), 132.8 (d), 132.5 (d), 131.6 (s), 129.0 (d), 80.6 (s), 52.0 (d), 28.3 (q).

(b) Preparation of ((E)-5-Benzylidene-4-oxo-cyclopent-2-enyl)-carbamic acid tert-butyl ester CTC-248

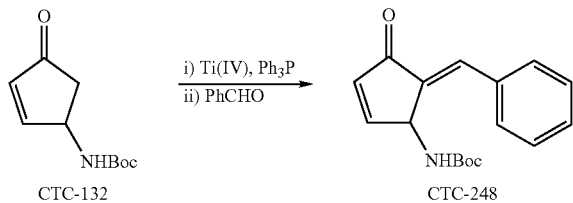

Triphenyl phosphine (333 mg, 1.27 mmol) was added to a stirred solution of the enone CTC-132 (250 mg, 1.27 mmol) in dichloromethane (6 ml) at room temperature, under an atmosphere of argon. The resulting mixture was then cooled to −50° C. and titanium (IV) isopropoxide (0.19 ml, 0.64 mmol) and then titanium (IV) chloride (70 μl, 0.64 mmol) were added dropwise over 3 minutes each. The mixture was stirred at −50° C. for a further 15 minutes, then benzaldehyde (0.39 ml, 3.84 mmol) was added over 3 minutes. The reaction mixture was then allowed to warm to room temperature over 16 hours. An aqueous solution of potassium carbonate (10% aq., 6 ml) was then added, the biphasic mixture was stirred for 90 minutes and the mixture was extracted with diethyl ether (5×6 ml). The combined organic extracts were then dried over MgSO$_4$, and evaporated in vacuo. Flash chromatography (SiO$_2$, 20%, then 35% ethyl acetate in hexane) gave the starting enone CTC-132 (98 mg, 0.50 mmol, 39% recovery) as a white solid, after giving the less polar dieneone CTC-248 (180 mg, 0.63 mmol, 50% (82% based on recovery) also as a white solid; $\delta_H$ (400 MHz, CDCl$_3$) 7.62–7.56 (3H, m, CH=CHC=O+ArH), 7.49 (1H, br. s, C=CHAr), 7.44–7.39 (3H, m, ArH), 6.50 (1H, dd J 5.9 & 1.6 Hz, CH=CHC=O), 5.81 (1H, br. d J 7.2 Hz, NH), 4.42 (1H, br. d J 7.2 Hz, CHNH), 1.44 (9H, s, CO$_2$C(CH$_3$)$_3$); $\delta_C$ (100 MHz, CDCl$_3$) 195.5 (s), 157.7 (d), 155.3 (s), 135.4 (d), 134.3 (d), 133.1 (s), 132.2 (s), 131.4 (d), 130.1 (d), 128.7 (d), 80.4 (s), 52.1 (d), 28.3 (q).

(c) Preparation of (1S)-[4-Oxo-(E)-5-(2,4,6-trimethyl-benzylidene)-cyclopent-2-enyl]-carbamic acid tert-butyl ester CTC-285

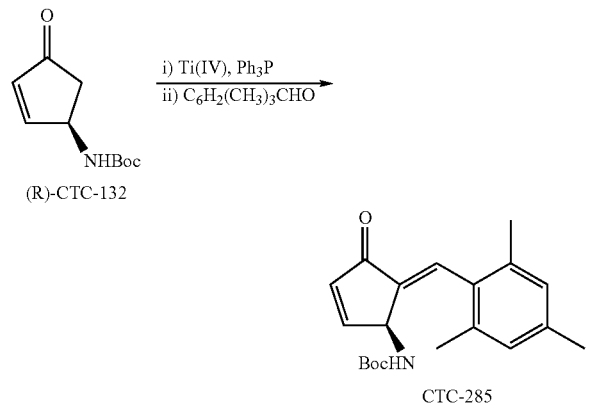

Triphenyl phosphine (267 mg, 1.02 mmol) was added to a stirred solution of the enone (R)-CTC-132 (201 mg, 1.02 mmol) in dichloromethane (5 ml) at room temperature, under an atmosphere of argon. The resulting mixture was then cooled to −50° C. and titanium (IV) isopropoxide (0.15 ml, 0.51 mmol) and then titanium (IV) chloride (56 μl, 0.51 mmol) were added dropwise over 3 minutes each. The mixture was stirred at −50° C. for a further 15 minutes, then mesitaldehyde (0.45 ml, 3.05 mmol) was added over 3 minutes. The reaction mixture was then allowed to warm to room temperature over 15 hours. An aqueous solution of potassium carbonate (10% aq., 6 ml) was then added and the biphasic mixture was stirred for 2 hours then filtered through a small pad of celite washing with dichloromethane (10 ml) and diethyl ether (10 ml). The organic phase of the filtrate was then separated and the aqueous phase was extracted with diethyl ether (4×5 ml). The combined organics were then dried over MgSO$_4$, and evaporated in vacuo. Flash chromatography (SiO$_2$, 20%, then 35% ethyl acetate in hexane) gave the starting enone (R)-CTC-132 (135 mg, 0.68 mmol, 67% recovery) as a white solid, after giving the less polar dieneone CTC-285 (80 mg, 0.24 mmol, 24% (73% based on recovery) also as a white solid; $\delta_H$ (400 MHz, CDCl$_3$) 7.57 (1H, s, C=CHAr), 7.44 (1H, dd J 6.3 & 2.2 Hz, CH=CHC=O), 6.87 (2H, s, ArH), 6.48 (1H, dd J 6.0 & 1.9 Hz, CH=CHC=O), 5.33 (1H, br. d J 5.6 Hz, NH), 4.10 (1H, br. d J 5.6 Hz, CHNH), 2.26 (3H, s, p-ArCH$_3$), 2.20 (6H, s, o-Ar(CH$_3$)$_2$), 1.22 (9H, s, CO$_2$C(CH$_3$)$_3$); $\delta_C$ (100 MHz, CDCl$_3$) 194.4 (s), 158.1 (d), 154.3 (s), 137.6 (s), 137.5 (s), 135.9 (d), 135.1 (s), 134.3 (d), 130.4 (s), 128.4 (d), 79.7 (s), 52.6 (d), 28.1 (q), 20.9 (q), 20.2 (q).

(d) Preparation of (1S)-[(E)-5-(2,5-Dimethoxy-benzylidene)-4-oxo-cyclopent-2-enyl]-carbamic acid tert-butyl ester CTC-286

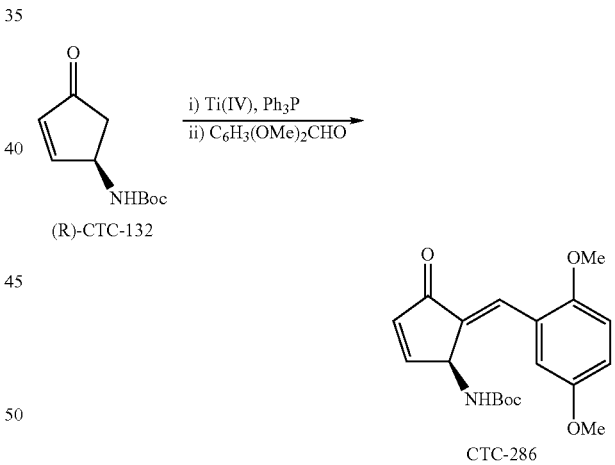

Triphenyl phosphine (267 mg, 1.02 mmol) was added to a stirred solution of the enone (R)-CTC-132 (201 mg, 1.02 mmol) in dichloromethane (5 ml) at room temperature, under an atmosphere of argon. The resulting mixture was then cooled to −50° C. and titanium (IV) isopropoxide (0.15 ml, 0.51 mmol) and then titanium (IV) chloride (56 μl, 0.51 mmol) were added dropwise over 3 minutes each. The mixture was stirred at −50° C. for a further 15 minutes, then a solution of 2,5-dimethoxybenzaldehyde (508 mg, 3.06 mmol) in dichloromethane (1 ml) was added over 3 minutes. The reaction mixture was then allowed to warm to room temperature over 18 hours. An aqueous solution of potassium carbonate (10% aq., 6 ml) was then added and the biphasic mixture was stirred for 2 hours then filtered through a small pad of celite washing with dichloromethane (10 ml) and diethyl ether (10 ml). The organic phase of the filtrate was then separated and the aqueous phase was extracted with diethyl ether (4×5 ml). The combined organics were then dried over MgSO$_4$, and evaporated in vacuo. Flash chromatography (SiO$_2$, 20%, then 35% ethyl acetate in hexane) gave the starting enone (R)-CTC-132 (51 mg, 0.26 mmol, 25% recovery) as a white solid, after giving the less polar dieneone CTC-286 (210 mg, 0.61 mmol, 60% (80% based on recovery) also as a yellow solid; $\delta_H$ (400 MHz, CDCl$_3$) 7.87 (1H, s, C=CHAr), 7.57 (1H, dd J 5.9 & 2.0 Hz, CH=CHC=O), 7.09 (1H, d J 2.9 Hz, o-ArH), 6.93 (1H, dd J 9.1 & 2.9 Hz, p-ArH), 6.86 (1H, d J 9.1 Hz, m-ArH), 6.49 (1H, dd J 5.9 & 1.6 Hz, CH=CHC=O), 5.77 (1H, br. d J 7.0 Hz, NH), 4.41 (1H, br. d J 7.0 Hz, CHNH), 3.85 (3H, s, OCH$_3$), 3.80 (3H, s, OCH$_3$), 1.38 (9H, s, CO$_2$C(CH$_3$)$_3$); $\delta_C$ (100 MHz, CDCl$_3$) 195.4 (s), 157.5 (d), 153.4 (s), 138.5 (s), 135.5 (d), 132.6 (s), 129.1 (d), 122.7 (d), 118.1 (s), 115.8 (s), 114.6 (d), 112.0 (d), 80.2 (s), 56.1 (q), 55.6 (9), 52.3 (d), 28.2 (q).

(e) Preparation of (2R)-3-((1R,2R)-(E)-3-Benzylidene-2-tert-butoxycarbonylamino-4-oxocyclopentylsulfanyl)-2-tert-butoxycarbonylaminopropionic acid CTM-228

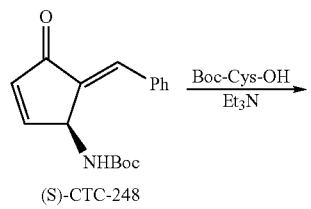

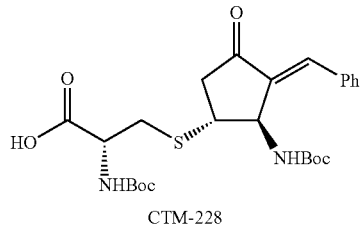

CTM-228

Boc-Cys-OH (3.68 g, 16.7 mmol) and triethylamine (2.4 ml, 17.5 mmol) were added successively to a stirred solution of dienone (S)-CTC-248 (5.00 g, 17.5 mmol) in chloroform (150 ml) at room temperature. The mixture was stirred at room temperature for 40 hours, then evaporated in vacuo. Recrystallisation from dichloromethane then gave the thiol adduct CTM-228 as a DCM solvate (1:1) as a white crystal suitable for X-ray structure determination. This was dissolved in TBME (100 ml), evaporated in vacuo, then dissolved in TBME (50 ml) and hexane (50 ml), and evaporated in vacuo again in order to give CTM-228 (3.82 g, 7.54 mmol, 45%) as a white solvent-free solid; $\delta_H$ (400 MHz, CDCl$_3$) 7.66 (1H, d J 1.4 Hz, C=CH), 7.59–7.55 (2H, m, ArH), 7.47–7.44 (3H, m, ArH), 5.73 (1H, br. s, NHBoc), 5.08 (1H, br. s, NHBoc), 4.89 (1H, br. s, CHNHBoc), 4.62 (1H, br. s, CHNHBoc), 3.73 (1H, d J 6.2 Hz, CHSR), 3.34 (1H, dd J 14.0 & 6.5 Hz, CHCHHSR), 3.15–3.06 (1H, m, CHCHHSR), 2.97 (1H, dd J 18.8 & 7.9 Hz, CHHCHSR), 2.35 (1H, d J 18.8 Hz, CHHCHSR), 1.49 (9H, s, CO$_2$C(CH$_3$)$_3$), 1.43 (9H, s, CO$_2$C(CH$_3$)$_3$); m/z (ES) 529.1979 ([MNa]$^+$ C$_{25}$H$_{34}$N$_2$O$_7$NaS requires 529.1984).

Example 34

General Preparation of —SR$^3$ Derivatives from Cyclopentenone Precursors:

(a) (R)-2-tert-Butoxycarbonylamino-3-[(1S,2S)-2-(tert-butyldimethylsilanyloxy)-4-oxo-cyclopentylsulfanyl]propionic acid methyl ester

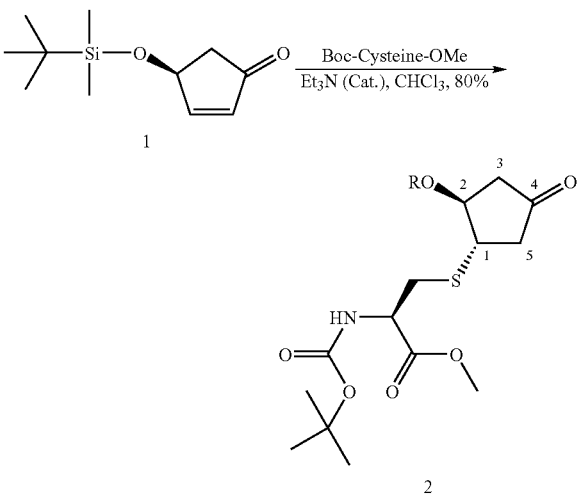

R = SiMe$_2^t$Bu

A solution of enone 1 (0.30 g, 1.41 mmol) in anhydrous chloroform (5 cm$^3$) was added to a solution of Boc-cysteine (0.33 g, 1.41 mmol) and a catalytic amount of triethylamine (3 drops) in anhydrous chloroform (5 cm$^3$). The reaction was stirred under N$_2$ for 16 hours until TLC analysis confirmed the disappearance of the enone. The solvent was removed under reduced pressure giving a pale yellow oil. Purification by flash column chromatography [R$_f$=0.25 (ethyl acetate-petroleum ether; 1:4)] gave the adduct 2 (0.50 g, 80% yield) as a colorless oil which solidified on standing at −2° C.; m.p. 52–53° C.; $\nu_{max}$ (film)/cm$^{-1}$ 3470, 3054, 2955, 2950, 2857, 1747, 1713; $[\alpha]_D^{22}$ −40.4 (c=0.52, MeOH); $\delta_H$ (400 MHz, CDCl$_3$) 0.09 (3H, s, CH$_3$), 0.12 (3H, s, CH$_3$), 0.88 (9H, s, CH$_3$), 1.45 (9H, s, CH$_3$), 2.14 (1H, dd, J 4.5 and 18.5 Hz, 5-CH$_A$H$_B$), 2.16 (1H, dd, J 2.5 and 18.0 Hz, 3-CH$_A$H$_B$), 2.68 (1H, dd, J 5.5 and 18.0 Hz, 3-CH$_A$H$_B$), 2.84 (1H, dd, J 7.5 and 18.5 Hz, 5-CH$_A$H$_B$), 2.99 (1H, dd, J 5.5 and 13.5 Hz, CH$_2$S), 3.13(1H, dd, J 5.0 and 13.5 Hz, CH$_2$S), 3.30–3.36 (1H, m, 1-CHS), 3.77 (3H, s, CH$_3$), 4.23–4.27 (1H, m, 2-CHO), 4.56–4.61 (1H, m, CH), 5.34 (1H, d, J 7.5 Hz, NH); $\delta_C$ (100 MHz; CDCl$_3$); −4.40, −4.39, 18.0, 26.0, 28.7, 34.5, 43.9, 46.4, 48.9, 53.0, 53.4, 75.1, 80.6, 155.4, 178.4, 214.4; m/z (CI) 465 ([M+NH$_4$]$^+$, 5%), 448 ([M+H]$^+$, 5%), 136 (100). 155 (54), 230 (46), Found: [M+H]$^{30}$, 448.21794, C$_{20}$H$_{37}$SiSO$_6$NH requires 448.21893; Found C, 53.78; H, 8.33; N, 3.00%, C$_{20}$H$_{37}$NO$_6$SSi requires C, 53.66; H, 8.33; N, 3.13%. For the general method adapted see: V. van Axel Castelli, A. Dalla Cort, L. Mandolini, *J. Am. Chem. Soc.*, 1998, 120, 12688–12689.

(b) (R)-2-tert-Butoxycarbonylamino-3-[(1R,2R)-2-(tert-butyldimethylsilanyloxy)-4-oxo-cyclopentylsulfanyl]propionic acid methyl ester

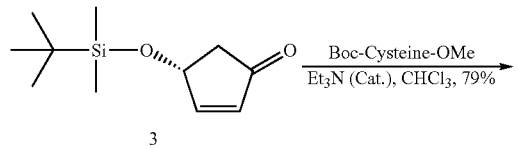

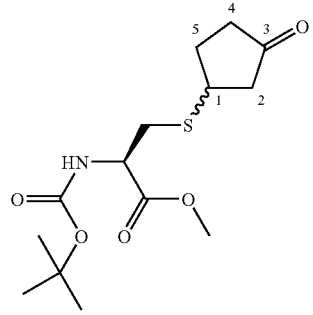

R = SiMe₂ᵗBu

The compound was prepared using the general procedure described previously. Purification by flash column chromatography [$R_f$=0.2 (ethyl acetate-petroleum ether; 1:4)] gave 4 as a colorless oil (79% yield); $v_{max}$ (film)/cm⁻¹ 3367, 2953, 2929, 2856, 1750, 1715; $[\alpha]_D^{19}$+18.5 (c=0.54, MeOH); $\delta_H$ (400 MHz, CDCl₃); 0.08 (3H, s, CH₃), 0.12 (3H, s, CH₃), 0.88, (9H, s, CH₃) 1.45 (9H, s, CH₃), 2.14 (1H, dd J 2.5 and 18.5 Hz, 5-CH$_A$CH$_B$), 2.16 (1H, dd, J 4.5 and 18.0 Hz, 3-CH$_A$H$_B$), 2.70 (1H, dd, J 5.5 and 18.5 Hz, 5-CH$_A$H$_B$), 2.77 (1H dd, J 7.5 and 18.0 Hz, 3-CH$_A$H$_B$), 3.05 (1H, dd, J 5.0 and 13.5 Hz, CH₂S), 3.09 (1H, dd, J 4.75 and 13.5 Hz, CH₂S), 3.34–3.39 (1H, m, 1-CHS), 3.78 (3H, s, OCH₃), 4.31–4.36 (1H, m, 2-CHO), 4.55–4.63 (1H, m, CH), 5.35 (1H, d, J 7.5 Hz, NH); $\delta_C$ (100 MHz; CDCl₃); −4.81, −4.79, 17.8, 25.6, 28.2, 33.9, 42.8, 45.0, 48.7, 52.6, 53.4, 74.6, 80.3, 155.0, 171.1, 214.1; m/z (CI) 465 ([M+NH₄]⁺, 10%), 448 ([M+H]⁺, 5%) 136 (100). 155 (35), 230 (54), Found: [M+H]⁺, 448.21794, C₂₀H₃₇SiSO₆N H requires [M+H]⁺, 448.21893.

(c) (R)-2-tert-Butoxycarbonylamino-3-(3-oxocyclopentylsulfanyl)propionic acid methyl ester

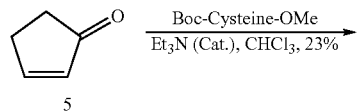

The compound was prepared using the general procedure described previously. Purification by flash column chromatography (ethyl acetate-petroleum ether; 1:2) gave 6 as a colorless waxy solid (23% yield) as a mixture of diastereomers. $R_f$=0.16 (ethyl acetate-petroleum ether; 1:2); $v_{max}$ (firm)/cm⁻¹ 3355, 2976, 2940, 1745, 1713, 1506, 1368, 1161; $\delta_H$ (400 MHz, CDCl₃); 1.45 (9H, s, CH₃), 1.89–2.00 (1H, m, CH₂, 2.14–2.24 (2H, m, CH₂), 2.32–2.49 (2H, m, CH₂), 2.58 (1H, dd, J 7.5 and 18.5 Hz, CH$_A$H$_B$), 2.93–3.13 (2H, m CH₂S), 3.47–3.55 (1H, m, 1-CHS), 3.77 (3H, s, OCH3), 4.55 (1H, m, CH), 5.36 (1H, s (br), NH); $\delta_C$ (100 MHz; CDCl₃) 28.3, 29.8 and 29.9, 33.5 and 33.7, 36.9, 40.8, 45.0 and 45.6, 52.6, 80.2, 155.1, 171.3, 214.8; m/z (CI) 335 ([M+NH₄]⁺, 25%), 318 ([M+H]⁺, 9%), 277 (30%), 218 (70%); (Found: [M+H]⁺, 318.13747, C₁₄H₂₃NO₅S H requires [M+H]⁺, 317.13754; Found C, 52.39; H, 7.19; N, 4.22%, C₁₄H₂₃NO₀S requires C, 52.96; H, 7.30; N, 4.43%.

Activity of Compounds in Accordance with the Invention

Preferred compounds of the present invention have activity in one or more of the assays described in Examples 3 to 8 below.

Certain compounds of the present invention may be advantageous in avoiding the affect of lowering blood pressure that is associated with various prostaglandins. An assay for this is set out in Example 8 below.

Example 35

(a) Effect of Inventive Compounds on the Reactivity of Transcription Factors HSF and NF-κB HeLa cell clone 13B, stably transfected with a luciferase reporter plasmid controlled by the human hsp70 promoter, and HeLa κB-transformed cells, stably transfected with a luciferase reporter plasmid controlled by a synthetic NF-κB-STM construct, were maintained in DMEM medium supplemented with 10% FBS, L-glutamine (2 mM) and G418 (250 μg/ml) at 37° C. in a 5% CO₂ humidified atmosphere.

Cells were seeded at a density of 4×10⁴ cells/well in 96-well plates. After 18–20 h, the medium was removed and cells were treated for 8 h with the test compounds (100 μl) at the appropriate dilutions in serum-free medium. For the NF-κB-dependent reporter gene assay, cells were stimulated with TPA (25 ng/ml) 2 h after exposure to the compounds.

After incubation, the medium was removed and cells were lysed in 10 μl of lysis buffer. The luciferase activity was determined by adding 100 μl of substrate and measuring the release of light using a Victor 1420 microplate reader (Wallac, Finland).

(b) Alamar Blue Cytotoxicity Assay

HeLa cells were plated in 96-well microtiter plates in 100 μl culture medium ($4\times10^4$/well). After 20 hours, the cells were exposed to the test compounds at different dilutions and incubated for the next 8 h at 37° C. in a 5% $CO_2$ humidified atmosphere. After 6 h incubation, the Alamar Blue was added in an amount equal to 10% of the culture volume (10 μl). Two hours after the addition of the Alamar Blue, the fluorescence was measured using a Victor 1420 microplate reader.

(c) Neutral Red Cytotoxicity Assay

This assay was carried out on HeLa cells using a technique analogous to that described below in Example 36(b) for Monkey Kidney 37RC cells.

(d) Production of HeLa cell clones stably transfected with NF-κB-LUC

The fragment Kpn I-BamH I from the pGL3 basic vector containing the luciferase gene (PROMEGA) was inserted in the pcDNA3 vector (INVITROGEN) digested with Bgl II-KpnI. (This digestion removes the CMV-promoter from pcDNA3.) The resulting new vector was digested with Kpn I-Hind III and a promoter containing a '5×NF-κB binding sites-TATA box' sequence was inserted upstream of the luciferase gene. This vector has been named STM.

To obtain stable HeLa cell lines expressing the luciferase gene under the control of NF-κB, HeLa cells were transfected (using lipofectamine plus GIBCO) with the STM-Pvu I linearized vector, and selected for 20 days with G418 (800 μg/ml). After selection, the resistant HeLa cell pool was controlled (in quadruplicate samples) for luciferase activity after stimulation with TNFα, IL-1 and TPA.

The respective luciferase activities were:
1) Control: 1369±149
2) TNFα: 6111±1231
3) IL-1: 11814±1151
4) TPA: 7181±444

Clones were selected.

Results

The results obtained from the assays described in parts (a) and (b) of this example for the following compounds in accordance with the invention were as follows:

| Compound | HSF AC$_{200}$/μM | NF-κB IC$_{50}$/μM | Toxicity Alamar Blue LC$_{50}$/μM | Toxicity Neutral Red LC$_{50}$/μM |
| --- | --- | --- | --- | --- |
| CTC-110 | 30 | 47 | >800 | n.d. |
| CTC-121 | 2.8 | 4.7 | >800 | n.d. |
| CTC-122 | 13 | 12 | 227 | n.d. |
| CTC-132 | 51 | 52 | >800 | n.d. |
| CTC-133 | 13 | 14 | >800 | n.d. |
| CTC-145 | 13 | 38 | 506 | n.d. |
| CTC-150 | 3 | 7 | 314 | n.d. |
| CTC-154 | 13 | 14 | >800 | n.d. |
| CTC-162 | <6.2 | <6.2 | 234 | n.d. |
| CTC-164 | >100 | 40 | >800 | n.d. |
| CTC-171 | 51 | 38 | >800 | n.d. |
| CTC-172 | <6.2 | <6.2 | 50 | n.d. |
| CTC-177 | 8 | 14 | 239 | n.d. |
| CTC-191 | 2 | 7 | >800 | n.d. |
| CTC-195 | 5 | 6.6 | >800 | n.d. |
| CTC-199 | 1.8 | 5 | >800 | n.d. |
| CTM-126 | 18 | 21 | >800 | n.d. |
| CTC-253 | 13 | 18 | >800 | n.d. |
| CTC-252 | 27 | 57 | >800 | n.d. |
| CTC-304 | <6.2 | <6.2 | n.d. | 79 |
| CTC-229 | 12 | 19 | n.d. | 98 |
| CTC-260 | 10 | 9 | n.d. | 74 |
| CTC-271 | 49 | 39 | n.d. | 104 |
| CTC-267 | 18 | 35 | n.d. | 233 |
| CTM-238 | 26 | 17 | n.d. | 113 |
| CTM-237 | 28 | 9 | n.d. | 183 |
| CTM-236 | 13 | 10 | n.d. | 76 |
| CTC-247 | 2 | 9 | >800 | 72 |
| CTC-248 | 1.8 | 4 | >800 | 33 |
| CTC-285 | <6.2 | 10 | n.d. | 25 |
| CTM-228 | <6.2 | <6.2 | n.d. | 25 |

The AC$_{200}$/μM for HSF is the concentration at which the tested compound doubled the HSF activity in this assay. The IC$_{50}$/μM for NF-κB is the concentration at which the tested compound halved the NF-κB activity in this assay. These results show the tested compounds to be powerful activators of HSF and powerful inhibitors of NF-κB. The LC$_{50}$/μM is the concentration at which the tested compound killed half the cells in each assay. These results show that the tested compounds do not become significantly cytotoxic to HeLa cells until their concentration has very considerably exceeded that at which they were shown to activate HSF and inhibit the activity of NF-κB. (n.d. means not done)

Example 36

(a) Effect of Inventive Compounds on the Replication of Sendai Virus

Monkey kidney 37RC cells were grown at 37° C. in RPMI medium supplemented with 5% foetal bovine serum (FBS), L-glutarine (2 mM) and antibiotics. Sendai virus was grown in the allantoic cavity of 10-day-old embryonated eggs. Viral titre was expressed in haemagglutinating units (HAU) per ml; haemagglutinin titration was done according to standard procedures, as described in C. Amici et al. (J. Virol. 68: 6890–6899, 1994). 37RC cells were seeded at density of $6\times10^4$ cells/well in 24-well plates and incubated for 24 h. Confluent 37RC monolayers were infected with Sendai Virus (5 HAU/ml) for 1 h at 37° C. After 1 hour incubation, viral inoculum was removed and cells were treated with the test compounds at different concentrations. Virus yields were determined 24 h post infection by haemagglutinin titration. Mock-infected cells were treated identically and processed for cytotoxicity assay (Neutral Red assay) at the same time (see below). The results were expressed as HAU/ml (each point represents the mean of duplicate samples).

(b) Neutral Red Assay

Cell viability was determined using the Neutral Red assay. 37RC cells were seeded at density of $6\times10^4$ cells/well in 24-well plates and incubated for 24 h. Confluent 37RC monolayers were treated with the test compounds at different dilutions for 24 h at 37° C. After incubation, the medium was removed and the cells were incubated with RPMI medium containing 40 μg/ml Neutral Red dye (500 μl/well). After 2 h at 37° C., the monolayers were washed with phosphate-buffered saline (PBS) and then with a solution containing 1% $CaCl_2$ and 0.5% formaldehyde. After washing, a solution containing 1% acetic acid/50% ethanol was added to the monolayers (250 μl/well). After 10 min at room temperature, the absorbance was determined with a microplate reader (Victor 1420, Wallac) at 540 nm.

Results

The $ID_{50}$ (the 50% inhibitory dose/concentration) values at 24 hours in the assay described in part (a) and the $TD_{100}$, (the dose or concentration at which the tested compound was 100% toxic to uninfected cells, determined visually by microscopy) for the tested compounds are given below, together with the $LC_{50}$ (the 50% lethal dose/concentration) values from the neutral red assay.

| Compound | $ID_{50}/\mu M$ | $TD_{100}/\mu M$ | $LC_{50}/\mu M$ |
|---|---|---|---|
| CTC-121 | 1 | 50 | 4 |
| CTC-122 | 0.3 | 50 | |
| CTC-145 | 0.3 | 10 | |
| CTC-150 | 0.9 | 50 | |
| CTC-132 | 20 | 100 | |
| CTC-199 | 1 | 50 | 4 |
| CTC-195 | 0.4 | 10 | 4 |
| CTC-171 | 20 | 100 | 59 |
| CTC-172 | 0.3 | 10 | 4 |
| CTC-247 | 0.6 | 10 | 3.4 |
| CTC-248 | 0.6 | 10 | 33 |

These latter results show that all of the compounds tested are inhibitors of Sendai virus replication at concentrations well below those at which they become toxic to uninfected 37RC cells.

Example 37

Effect of Inventive Compounds on Infection with Influenza Virus.

Human lung adenocarcinoma A549 cells are grown at 37° C. in RPMI-1640 medium, supplemented with 10% fetal calf serum (FCS, Gibco) and antibiotics. Influenza A virus A/WSN/33 (H1N1) (WSN virus) is grown in the allantoic cavity of 10-day-old embryonated eggs. Virus titers are determined by hemagglutinin titration, according to standard procedures (Pica F, Palamara A T, Rossi A, De Marco A, Amici C and Santoro M G: $\Delta^{12}$-Prostaglandin $J_2$ is a potent inhibitor of influenza A virus replication. *Antimicrob. Agents Chemother.*, 44: 200–204, 2000). Confluent A549 monolayers are infected with WSN virus (10 $HAU/10^5$ cells) for 1 h at 37° C. After this time, viral inoculum is removed and cells are treated with different concentrations of inventive compound or ethanol-diluent. Viral yields are determined 24 and 48 h post infection (p.i.) and expressed as HAU/ml.

Example 38

MTT Assay

Cell viability is determined by the 3-(4,5-dimethylthiazol-2-yl)-2,5-diphenyltetrazolium bromide (MTT) assay. Uninfected A549 ($7.5 \times 10^4$ cells/well in 96 well plates) or 37RC cells ($2.5 \times 10^4$ cells/well in 96 well plates) are treated with different concentrations of inventive compound or ethanol diluent for 24 hours. After this time, 10 ml of a 0.5% MTT solution in PBS is added to the monolayers and the mixture is incubated for 2 h at 37° C. Reduced MTT (formazan) is extracted from cells by adding 100 μl of acidic isopropanol containing 10% Triton X-100, and formazan absorbance is measured in an ELISA microplate reader at two different wavelengths (540 and 690 nm).

Example 39

Assaying for Anti-Inflammatory Effect

Immune cells such as neutrophils and macrophages are activated in response to injury and infection. When activated they produce nitric oxide and superoxide radicals to kill foreign cells and cancer cells. They also produce a variety of cytokines and chemokines to cause further recruitment of immune cells in a cascade leading to the cardinal symptoms of inflammation; heat, redness, swelling, pain, and loss of function.

A key signalling step in the activation of the immune cells is the transcription factor nuclear factor κ B (NF-κB) (16). NF-κB regulates the transcription of a spectrum of pro-inflammatory genes such as IL-1, IL-2, TNF-α, ICAM-1, VCAM-1, and E-selectin as well as the inducible form of nitric oxide synthase (iNOS) and cyclo-oxygenase II.

Thus the activation of NF-κB occupies a critical position in the inflammatory cascade. A test compound can be tested for its effects on the induction of iNOS in a mouse macrophage model.

Mouse macrophages of the cell line RA W264.7 can be stimulated with gamma interferon and 0.1 U/ml of bacterial lipopolysaccharide (LPS) in 96-well plates (17). The induction of INOS can be measured by determination of the levels of nitrite ($NO_2^-$) formed in the supernatant, using the Griess reagent.

It can be determined whether or not a test compound has an inhibitory effect on nitrite formation (preferably at sub-micromolar concentrations). The natural cyclopentenone prostaglandin PG-$J_2$ can be used for comparison. (IC50 values obtained for $PGJ_2$ and a test compound can be compared).

If the results of the experiment indicated that the induction of the pro-inflammatory iNOS genes by interferon gamma and LPS treatment is suppressed by a test compound, the most likely explanation is that the test compound is inhibiting the activation of the NF-κB pathway.

Example 40

Assaying to Determine Whether or not a Compound Lowers Blood Pressure

Most prostaglandins have strong effects on vascular smooth muscle, and will lower blood pressure in animals and humans. A compound can be tested for its effect on the blood pressure of the anaestheized rat. Prostaglandins $A_1$ and $E_1$ can be used for comparison.

Male Wistar rats were anaesthetized and test drugs can be infused intravenously. Blood pressure and heart rate can be recorded from the femoral artery.

Prostaglandins $A_1$ and $E_1$ cause dose-dependant falls in blood pressure in doses from 30 μg/kg/min. It can be determined whether or not a test compound affects blood pressure at various dosages. As a control, solvent alone can be used.

If a compound does not cause significant changes in blood pressure, it may be devoid of the generalised effects on smooth muscle characteristic of natural cyclopentenone prostaglandins.

GENERAL REMARKS

The foregoing description of the invention is merely illustrative thereof and it should therefore be appreciated that various variations and modifications can be made without departing from the spirit or scope of the invention as set forth in the accompanying claims.

Where preferred or optional features are described in connection with particular aspects of the present invention, they shall be deemed to apply mutatis mutandis to other aspects of the invention unless the context indicates otherwise.

All documents cited herein are hereby incorporated by reference, as are any citations referred to in said documents.

REFERENCES

1. Feige U, Morimoto R, Yahara I, Polia B S. *Stress-inducible Cellular Responses*. Birkhaüser Verlag, Basel Boston Berlin, 1996.
2. Marber M S, Walker J M, Latchman D S, 'Yellon D M. *J. Clin. Invest.* 93, 1087–1094, 1994.
3. Feinstein D L e al. *J. Biol. Chem.* 271, 17724–17732, 1996.
4. Amici C, Giorgi C, Rossi A, Santoro M G. *J. Virol* 68, 6890–6897, 1994.
5. Santoro M G, in *Stress-inducible Cellular Reponses*. (Fiege U et al. eds, Birkhaüser Verlag, Basel Boston Berlin) pp. 337–357, 1996.
6. Santoro M G, Garaci 9, Amici C. *P.N.A.S. USA* 86, 8407–8411, 1989.
7. Amici C, Sistonen L, Santoro M G, Morimoto R I. *P.N.A.S. USA* 89, 6227–6231, 1992.
8. Santoro M G, Benedetto A. Carruba G, Garaci E, Jaffe B. *Science* 209, 1032–1034, 1980.
9. Santoro M G, *Trends Microbiol.* 5, 276–281, 1997.
10. Rozera C, Carattoli A, De Marco A, Amici C, Giorgi C, Santoro M G *J. Clin. Invest.* 97; 1795–1803, 1996.
11. Rossi A, Elia G, Santoro M G. *P.N.A.S. USA* 94, 746–750, 1997.
12. Thanos D, Maniatis T. *Cell* 80, 529–532, 1995.
13. Rossi A, Elia G, Santoro M G. *J. Biol. Chem.* 271, 32192–32196, 1996.
14. Shield M J. *Pharmacol. Ther.* 65, 125–137, 1995.
15. Sinclair S B et al. *J. Clin. Invest.* 84, 1063–1067, 1989.
16. Baeuerle P A and Henkel T (1994). Function and Activation of NF-Kappa B in the Immune System. Annual Reviews of Immunology 12: 141–179.
17. Colville-Nash P R et al. (1998). Inhibition of Inducible Nitric Oxide Synthase by Peroxisome Proliferator-Activated Receptor Agonists: Correlation with Induction of Heme Oxygenase 1. Journal of Immunology 161, 978–984.
18. K. J. Stone, R. D. Little, JOC, 1984, 49, 1849–1853.
19. A. Kawamoto, H. Kosugi, H. Uda, Chem. Lett., 1972, 807–810.
20. Moriguchi I, Hirono S, Liu Q, Nakagome Y, and Matsushita Y, (1992) Simple method of calculating octanol/water partition coefficient. Chem. Pharm. Bull. 40, 127–130.
21. Lipinski C, Lombardo F, Dominy B, Feeney P, (1997) Experimental and computational approaches to estimate solubility and permeability in drug discovery and development settings. Advanced Drug Delivery Reviews 23 (1997) 3–25.
22. Kondo, M.; Oya-Ito, T.; Kumagai, T.; Osawa, T.; Uchida, K. *J. Biolog. Chem.* 2001, 296, 12076–12083.
23. Silverman, R. B., *In The Organic Chemistry of Drug Design and Drug Action*; Academic Press; A Harcourt Science and Technology Company: San Diego, 1992, 336–338.
24. R. J. Flanagan, *Chemistry in Britain*, 2002, 28.
25. Meister, A., Anderson, M., E., *Ann. Rev. Biochem.* 1983, 52, 711–760.

The invention claimed is:

1. A compound of formula I:

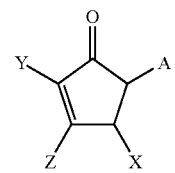

wherein:
A is hydrogen or $=CR^1R^2$;
Y and Z are each, independently, hydrogen or a halogen;
X is $-NR^4R^5$, or $R^7$;
when X is $-NR^4R^5$, A is $=CR^1R^2$;
$R^1$ is hydrogen, or a substituted or unsubstituted alkyl or alkenyl group containing 1–4 carbon atoms;
when X is $-NR^4R^5$, $R^2$ is a substituted or unsubstituted alkyl, alkenyl, alkynyl, aryl, aralkyl aralkenyl, or aralkynyl group, that optionally includes at least one heteroatom in its carbon skeleton and contains 1–12 carbon atoms;
when X is $R^7$, $R^2$ is an unsubstituted alkyl, alkenyl or alkynyl group, or a substituted or unsubstituted aryl, aralkyl aralkenyl, or aralkynyl group, that optionally includes at least one heteroatom in its carbon skeleton and contains 2–12 carbon atoms;
$R^4$ is hydrogen, a substituted or unsubstituted alkyl, alkenyl, alkynyl, aryl, aralkyl, aralkenyl, or aralkynyl group, that optionally includes at least one heteroatom in its carbon skeleton and contains 1–12 carbon atoms, $-COOR^8$, or $-COR^8$;
$R^5$ is hydrogen, or a substituted or unsubstituted alkyl or alkenyl group containing 1–5 carbon atoms;
$R^7$ is an unsubstituted alkyl, alkenyl, or alkynyl group, that contains 1–4 carbon atoms; and,
$R^8$ is an unsubstituted or halo-substituted alkyl, aryl, or aralkyl group, that contains 1–12 carbon atoms.

or a compound of formula II:

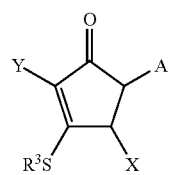

wherein:
A is hydrogen or $=CR^1R^2$;
Y is hydrogen or a halogen;
X is $-NR^4R^5$, or $R^7$;
$R^1$ is hydrogen, or a substituted or unsubstituted alkyl or alkenyl group containing 1–4 carbon atoms;
when X is $-NR^4R^{5,}$ $R^2$ is a substituted or unsubstituted alkyl, alkenyl, alkynyl, aryl, aralkyl, aralkenyl, or aralkynyl group, that optionally comprises at least one heteroatom in its carbon skeleton and contains 1–12 carbon atoms;

when X is $R^7$, $R^2$ is an unsubstituted alkyl, alkenyl or alkynyl group, or a substituted or unsubstituted aryl, aralkyl, aralkenyl, or aralkynyl group, that optionally comprises at least one heteroatom in its carbon skeleton and contains 1–12 carbon atoms;

$R^3$ is a substituted or unsubstituted alkyl, alkenyl, alkynyl, aryl, aralkyl, aralkenyl, or aralkynyl group, that optionally comprises at least one heteroatom in its carbon skeleton and contains 1–12 carbon atoms; or $R^3$ is an $R^xCH_2$— group, wherein $R^x$ is hydrogen or a substituted or unsubstituted alkyl, alkenyl, alkynyl, aryl, aralkyl, aralkenyl, or aralkynyl group, that optionally comprises at least one heteroatom in its carbon skeleton;

$R^4$ is hydrogen, a substituted or unsubstituted alkyl, alkenyl, alkynyl, aryl, aralkyl, aralkenyl, or aralkynyl group, that optionally comprises at least one heteroatom in its carbon skeleton and contains 1–12 carbon atoms, $-COOR^8$, or $-COR^8$;

$R^5$ is hydrogen, or a substituted or unsubstituted alkyl or alkenyl group containing 1–5 carbon atoms;

$R^7$ is an unsubstituted alkyl, alkenyl, or alkynyl group, that contains 1–4 carbon atoms; and, $R^8$ is an unsubstituted or halo-substituted alkyl, aryl, or aralkyl group, that contains 1–12 carbon atoms.

2. A compound as in claim 1 wherein A is $=CR^1R^2$ and the inventive compounds are of the formulae Ia and IIa:

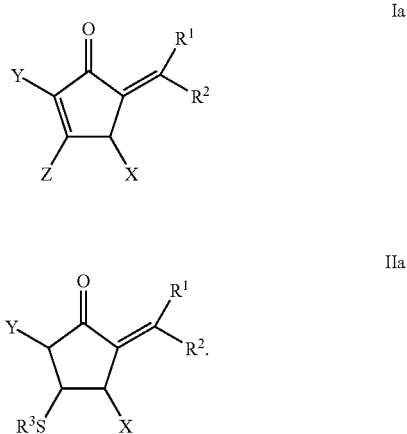

3. A compound as in claim 1 or 2, wherein $R^1$ is hydrogen or an alkyl group containing 1, 2, 3 or 4 carbon atoms.

4. A compound as in claim 3, wherein $R^1$ is hydrogen.

5. A compound as in claim 1 or 2, wherein $R^2$ contains 1, 2, 3, 4, 5, 6, 7, 8, 9, 10 or 11 carbon atoms.

6. A compound as in claim 1 or 2, wherein $R^2$ is an unsubstituted alkyl, or a substituted or unsubstituted aryl or aralkyl group.

7. A compound as in claim 1 or 2, wherein $R^2$ is an alkyl group containing 3, 4, 5, or 6 carbon atoms or an, optionally substituted, phenyl group.

8. A compound as in claim 1 or 2, wherein $R^2$ is an isopropyl, cyclopropyl, 1,2-dimethylethyl, n-pentanyl, n-hexanyl, phenyl, 4-methoxyphenyl, 4-fluorophenyl, 4-chlorophenyl, 2,4,6-trimethylphenyl, 2,5-dimethoxyphenyl or 4-nitrophenyl group.

9. A compound as in claim 1 or 2, wherein $R^3$ is an $R^xCH_2$-group, and $R^x$ is hydrogen or a substituted or unsubstituted alkyl, alkenyl, alkynyl, aryl, aralkyl, aralkenyl, or aralkynyl group, that optionally comprises at least one heteroatom in its carbon skeleton.

10. A compound as in claim 9, wherein $R^3$ contains 1–12 carbon atoms.

11. A compound as in claim 1 or 2, wherein $R^3$ or $R^x$ comprises at least one hydrophilic group.

12. A compound as in claim 11, wherein said hydrophilic group is or comprises a hydroxyl, carbonyl, carboxyl, amino, amido, quaternary ammonium or thiolyl group.

13. A compound as in claim 12, wherein $R^3$ or $R^x$ provides the functionality of an amine, amide, peptide, ester, carboxylic acid, carboxylic acid salt, alcohol, aldehyde, ketone or thiol.

14. A compound as in claim 1 or 2, wherein the group or $R^x$ comprises at least one lipophilic group and/or is lipophilic.

15. A compound as in claim 14, wherein the lipophilic group comprises a substituted or unsubstituted alkyl, alkenyl, alkynyl, aryl, aralkyl, aralkenyl, or aralkynyl group that, optionally, comprises at least one heteroatom in its carbon skeleton.

16. A compound as in claim 1 or 2, wherein the group $-SR^3$ is an S-cysteinyl or a substituted S-cysteinyl group.

17. A compound as in claim 16, wherein the substituted S-cysteinyl group is a di- or tri-peptide group that comprises an S-cysteinyl moiety.

18. A compound as in claim 16, wherein the substituted S-cysteinyl group is an S-glutathionyl or S-cysteinyl ester group.

19. A compound as in claim 16, wherein the substituted S-cysteinyl group is a N-tert-butoxycarbonyl S-cysteinyl or N-tert-butoxycarbonyl S-cysteinyl ester group.

20. A compound as in claim 1 or 2, wherein Y and Z are independently chlorine or hydrogen.

21. A compound as in claim 1 or 2, wherein X is $-NR^4R^5$.

22. A compound as in claim 1 or 2, wherein $R^4$ is a phenyl group, $-COOR^8$ or $-COR^8$.

23. A compound as in claim 1 or 2, wherein $R^5$ is hydrogen or a COO-alkyl group, wherein the alkyl group contains 1–4 carbon atoms.

24. A compound as in claim 1 or 2, wherein $R^7$ is an alkyl group containing 1, 2, 3, 4 or 5 carbon atoms.

25. A compound as in claim 1 or 2, wherein $R^8$ is an optionally halo-substituted alkyl group containing 1, 2, 3, 4 or 5 carbon atoms, or an aryl group.

26. A compound as in claim 25, wherein $R^8$ is a t-butyl, phenyl, chloromethyl or ethyl group.

27. A compound of formula II, as in claim 1, having a calculated or measured logP value that is at least 0.25, 0.5, 0.75, 1 or 1.25 higher or lower than the logP value for the equivalent compound of formula I, wherein the logP values for said compounds are calculated or measured using the same technique.

28. A compound as in claim 1 or 2, having activity in respect of one or more of the following:
(a) activating HSF
(b) inhibiting NF-κB
(c) inhibiting the replication of HSV-1
(d) inhibiting the replication of Sendai virus
(e) inhibiting influenza virus.

29. A pharmaceutical composition comprising a compound according to claim 1 or 2, and optionally a pharmaceutically acceptable carrier.

30. A food for an aquatic organism comprising a compound according to claim 1 or 2.

31. An aquatic environment comprising a compound according to claim 1 or 2.

32. A method of treating a viral-mediated disorder, a bacterial-mediated disorder, a disorder mediated by radiation, an inflammatory disorder, a disorder of the immune system, ischemia, arteriosclerosis, a disorder involving cell proliferation, cancer, high blood pressure, or a disorder involving damage to cells or killing of cells, comprising administering a compound as in claim 1 or 2 to a subject suffering from one or more of said conditions, in an amount effective to at least ameliorate at least one of said conditions.

33. A method of decreasing or increasing the lipophilicity and/or increasing or decreasing the water solubility and/or the therapeutic index of a pharmaceutically active compound of formula I as defined in claim 1, said method comprising forming an adduct of said compound of formula I and a thiol of the formula $HSR^3$, wherein $R^3$ is a group as defined in claim 1 and the adduct is a compound of formula II as defined in claim 1.

34. A method as in claim 33, wherein the adduct is formed via a Michael reaction between the unsaturated second compound and the thiol.

35. A method as in claim 33 or 34, wherein a further $-SR^3$ group is added into a side chain bound to the cyclopentenone or cyclopentanone group in the adduct.

36. An adduct, prepared or preparable by a method as in claim 33.

37. A compound as in claim 19, wherein the substituted S-cysteinyl group is a N-tert-butoxycarbonyl S-cysteinyl methyl or ethyl ester group.

38. A method as in claim 32, wherein the disorder of the immune system is psoriasis.

39. A method of treating a viral-mediated disorder, an inflammatory disorder, a disorder of the immune system or high blood pressure, comprising administering a compound as in claim 1 or 2 to a subject suffering from one or more of said conditions, in an amount effective to at least ameliorate at least one of said conditions.

* * * * *

UNITED STATES PATENT AND TRADEMARK OFFICE
CERTIFICATE OF CORRECTION

PATENT NO. : 7,183,440 B2  Page 1 of 1
APPLICATION NO. : 11/059086
DATED : February 27, 2007
INVENTOR(S) : Roberts et al.

It is certified that error appears in the above-identified patent and that said Letters Patent is hereby corrected as shown below:

At Claim 1, column 60, line 55, please replace the structure:

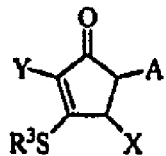

with the structure:

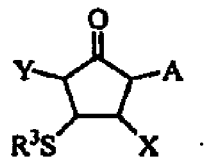

Signed and Sealed this

Twenty-ninth Day of May, 2007

JON W. DUDAS
*Director of the United States Patent and Trademark Office*